(12) United States Patent
Kim et al.

(10) Patent No.: US 8,080,568 B1
(45) Date of Patent: Dec. 20, 2011

(54) 2-PYRIDYL SUBSTITUTED IMIDAZOLES AS THERAPEUTIC ALK5 AND/OR ALK4 INHIBITORS

(75) Inventors: Dae-Kee Kim, Seoul (KR); Yhun Yhong Sheen, Seoul (KR); Chenghua Jin, Seoul (KR); Chul-Yong Park, Seoul (KR); Sreenu Domalapally, Seoul (KR); Sudhakar Rao Kota, Seoul (KR); Krishnaiah Maddeboina, Seoul (KR); Subrahmanyam Vura Bala, Seoul (KR)

(73) Assignee: EWHA University - Industry Collaboration Foundation, Seoul (KR)

( * ) Notice: Subject to any disclaimer, the term of this patent is extended or adjusted under 35 U.S.C. 154(b) by 0 days.

(21) Appl. No.: 12/826,338

(22) Filed: Jun. 29, 2010

(51) Int. Cl.
*A61K 31/44* (2006.01)
*C07D 401/14* (2006.01)

(52) U.S. Cl. ..................... 514/357; 546/272.4
(58) Field of Classification Search ............... 546/272.4; 514/357
See application file for complete search history.

(56) References Cited

U.S. PATENT DOCUMENTS

| 7,407,958 B2 | 8/2008 | Kim et al. |
| 2003/0149277 A1 | 8/2003 | Gaster et al. |
| 2008/0319012 A1 | 12/2008 | Kim et al. |

FOREIGN PATENT DOCUMENTS

| WO | WO 00/61576 A | 10/2000 |
| WO | WO 01/62756 A | 8/2001 |
| WO | WO 02/055077 A | 7/2002 |
| WO | WO 03/087304 A | 10/2003 |
| WO | WO 2005/103028 A | 11/2005 |

OTHER PUBLICATIONS

Jordan, V. C. Nature Reviews: Drug Discovery, 2, 2003, 205.*
Dorwald, F. Zaragoza. Side Reactions in Organic Synthesis: A guide to Successful Synthesis Design, Weinheim; WILEY-VCH Verlag GmbH & Co. KGaA, 2005, Preface.*
Vippagunta, et al., Advanced Drug Delivery Reviews, 48, 2001, 18.*
Wang, Qingjian et al.: "Reduction of bleomycin induced lung fibrosis by transforming growth factorβ soluble receptor in hamsters", *Thorax*, 1999; 54, pp. 805-812.
Wahab, Nadia Abdel et al.: "Expression of extracellular matrix molecules in human mesangial cells in response to prolonged hyperglycaemia", *Biochem J.*, (1996), 316, pp. 985-992.
Shah, Mamta et al.: "Neutralisation of TGF-β$_1$ and TGF-β$_2$ or exogenous addition of TGF-β$_3$ to cutaneous rat wounds reduces scarring", *Journal of Cell Science*, 108, 1995, pp. 985-1002.
Sanderson, Nancy et al.: "Hepatic expression of mature transforming growth factor β1 in transgenic mice results in multiple tissue lesions", *Proc. Natl. Acad. Sci. USA*, vol. 92, Mar. 1995, pp. 2572-2576.
Ryu, Md, Ji-Kan et al.: "IN-1130, a Novel Transforming Growth Factor-β Type I Receptor Kinase (Activin Receptor-like Kinase 5) Inhibitor, Promotes Regression of Fibrotic Plaque and Corrects Penile Curvature in a Rat Model of Peyronie's Disease",*J Sex Med*, 2009;6, pp. 1284-1296.

Rosendahl, Alexander et al.: "Activation of the TGF-β/Activin-Smad2 Pathway during Allergic Airway Inflammation", *Am J. Respir. Cell Mol. Biol.*, vol. 25, 2001, pp. 60-68.
Pawlowski, John E. et al.: "Stimulation of Activin A Expresssion in Rat Aortic Smooth Muscle Cells by Thrombin and Angiotensin II Correlates with Neointimal Formation in Vivo", *J. Clin. Invest.*, vol. 100, No. 3, Aug. 1997, pp. 639-648.
Munz, Barbara et al.: "Overexpression of activin A in the skin oftransgenic mice reveals new activites of activin in epidermal morphogenesis, dermal fibrosis and wound repair", *The EMBO Journal*, vol. 18, No. 19, 1999, pp. 5205-5215.
Moon, J-A et al.: "IN-1130, a novel transforming growth factor-β type I receptor kinase (ALK5) inhibitor, suppresses renal fibrosis in obstructive nephropathy", *Kidney International*, 2006, 70, pp. 1234-1243.
McCaffrey, Timothy A. et al.: "Decreased Type II/Type I TGF-β Receptor Ratio in Cells Derived from Human Atherosclerotic Lesions", *J. Clin. Invest.*, vol. 96, Dec. 1995, pp. 2667-2675.
Matzuk, M.M. et al.: "Development of cancer cachexia-like syndrome and adrenal tumors in inhibin-deficient mice", *Proc. Natl. Acad. Sci. USA*, vol. 91, Sep. 1994, pp. 8817-8821.
Kim, MD, Jin Hyoung et al.: "IN-1233, an ALK-5 Inhibitor. Prevention of Granulation Tissue Formation after Bare Metallic Stent Placement in a Rat Urethal Model", *Radiology*, vol. 255; No. 1, Apr. 2010, pp. 75-82.
Luo, Jian et al.: "Glia-dependent TGF-β signaling, acting independently of the TH17 pathway, is critical for initiation of murine autoimmune encephalomyelitis", *The Journal of Clinical Investigation*, vol. 117, No. 11, Nov. 2007, pp. 3306-3315.
Long, MD, Phd, Lu et al.: "Altered Bone Morphogenetic Protein and Transforming Growth Factor-β Signaling in Rat Models of Pulmonary Hypertension", *Circulation*, Feb. 3, 2009, pp. 566-576.
Lee, Geun Taek et al.: "Effect of IN-1130, a Small Molecule Inhibitor of Transforming Growth Factor-β Type I Receptor/Activin Receptor-Like Kinase-5, on Prostate Cancer Cells", *The Journal of Urology*, vol. 180, Dec. 2008, pp. 2660-2667.
Jagirdar, Jaishree et al.: "Immunohistochemical Localization of Transforming Growth Factor Beta Isoforms in Asbestos-Related Diseases", *Environmental Health Perspectives 105*, Supplement 5, Sep. 1997, 11 pages.
Hojo, Minoru et al.: "Cyclosporine induces cancer progression by a cell-autonomous mechanism", *Nature*, vol. 397, Feb. 11, 1999, pp. 530-534.
Dahly, Annette J et al.: "Antihypertensive effects of chronic anti-TGF-β antibody therapy in Dahl S rats",*Am. J. Physiol. Regul. Integr. Comp. Physiol.*, 283: 2002, pp. R757-R767.
Cipriano, Sherry C. et al.: "Follistatin Is a Modulator of Gonadal Tumor Progression and the Activin-Induced Wasting Syndrome in Inhibin-Deficient Mice", *Endocrinology*, vol. 141, No. 7, 2000, pp. 2319-2327.
Broekelmann, Thomas J. et al.: "Transforming growth factor β$_1$ is present at sites of extracellular matrix gene expression in human pulmonary fibrosis", *Proc. Natl. Acad. Sci. USA*, vol. 88, Aug. 1991, pp. 6642-6646.

* cited by examiner

*Primary Examiner* — Rebecca Anderson

(74) *Attorney, Agent, or Firm* — Frommer, Lawrence & Haug LLP; Ronald R Santucci

(57) ABSTRACT

This invention relates to 2-pyridyl substituted imidazoles which are inhibitors of the transforming growth factor-β (TGF-β) type I receptor (ALK5) and/or the activin type I receptor (ALK4), methods for their preparation, and their use in medicine, specifically in the treatment and prevention of a disease state mediated by these receptors.

3 Claims, 8 Drawing Sheets

2-PYRIDYL SUBSTITUTED IMIDAZOLES AS THERAPEUTIC ALK5 AND/OR ALK4 INHIBITORS

This work was supported by National Research Foundation grant funded by the Korean government (M10870050001-08N7005-00110).

TECHNICAL FIELD OF THE INVENTION

This invention relates to 2-pyridyl substituted imidazoles which are inhibitors of the transforming growth factor-β (TGF-β) type I receptor (ALK5) and/or the activin type I receptor (ALK4), methods for their preparation, and their use in medicine, specifically in the treatment and prevention of a disease state mediated by these receptors.

BACKGROUND OF THE INVENTION

TGF-β denotes a family of proteins, TGF-β1, TGF-β2 and TGF-β3, which are pleiotropic modulators of cell proliferation and differentiation, wound healing, extracellular matrix production and immunosuppression. Other members of this superfamily include activins, inhibins, bone morphogenetic proteins, growth and differentiation factors and Müllerian inhibiting substance.

TGF-β1 transduces signals through two highly conserved single transmembrane serine/threonine kinases, the type I (ALK5) and type II TGF-β receptors. Upon ligand induced oligomerization, the type II receptor hyperphosphorylates serine/threonine residues in the GS region of the ALK5, which leads to activation of the ALK5 by creating a binding site for Smad proteins. The activated ALK5 in turn phosphorylates Smad2 and Smad3 proteins at the C-terminal SSXS-motif thereby causing their dissociation from the receptor and heteromeric complex formation with Smad4. Smad complexes translocate to the nucleus, assemble with specific DNA-binding co-factors and co-modulators to finally activate transcription of extracellular matrix components and inhibitors of matrix-degrading proteases.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Numerous experimental animal studies demonstrate an association between glomerular expression of TGF-β and fibrosis, including the Thy-1 rat model of proliferative glomerulonephritis, anti-GBM glomerulonephritis in rabbits, and the 5/6 nephrectomy rat model of focal segmental glomerulosclerosis, as has been reviewed recently (e.g., Bitzer, M. et al., *Kidney Blood Press. Res.* 21: 1-12 (1998)). Neutralizing antibody to TGF-β improves glomerular histology in the Thy-1 nephritis model (e.g., Border, W. A. et al., *Nature* 346: 371-374 (1990)).

Hyperglycemic conditions increase TGF-β mRNA and protein synthesis in both murine proximal tubule cells and human mesangial cells (e.g., Wahab, N. A. et al., *Biochem. J.* 316: 985-992 (1996); Rocco, M. V. et al., *Kidney Int.* 41: 107-114 (1992)). Diabetic patients with early kidney disease show increased accumulation of TGF-β mRNA and protein within the glomerulus (e.g., Yoshioka, K. et al., *Lab. Invest.* 68: 154-163 (1993)). In kidneys with chronic renal interstitial fibrosis, the hallmarks are thickened tubular basement membranes and an expanded interstitial compartment, with interstitial fibrosis characterized by an increase in collagens I, III, V, VII, and fibronectin (e.g., Eddy, A. A., *J. Am. Soc. Nephrol.* 7: 2495-2508 (1996)).

TGF-β gene expression and protein production are increased in a variety of animal models of pulmonary fibrosis including bleomycin, silica, asbestos, and radiation (e.g., Phan, S. H. and Kunkel, S. L., *Exp. Lung Res.* 18: 29-43 (1992); Williams, A. O. et al., *Am. J. Pathol.* 142: 1831-1840 (1993); Rube, C. E. et al., *Int. J. Radiat. Oncol. Biol. Phys.* 47: 1033-1042 (2000)). Coincident increase in TGF-β1 protein and collagen gene expression in adjacent tissue slices from idiopathic pulmonary fibrosis is observed in human pulmonary fibrotic disease (e.g., Broekelmann, T. J. et al., *Proc. Natl. Acad. Sci. USA* 88: 6642-6646 (1991)). Increased TGF-β production has been documented in patients with sarcoidosis, pneumoconiosis, asbestosis, and radiation-induced fibrosis (e.g., Khalil, N. et al., *Am. J. Respir. Cell. Mol. Biol.* 14: 131-138 (1996); Jagirdar, J. et al., *Environ. Health Perspect.* 105: 1197-1203 (1997)). Anti-TGF-β antibodies and TGF-β-soluble receptors could partially inhibit fibrosis in bleomycin-induced lung fibrosis rodent models (e.g., Giri, S, N. et al., *Thorax* 48: 959-966 (1993); Wang, Q. et al., *Thorax* 54: 805-812 (1999)). Tobacco smoke has been implicated as one of the most important factors that can cause small airway disease followed by chronic obstructive pulmonary disease (COPD) (e.g., Wright, J. M. et al., *Am. Rev. Respir. Dis.* 146: 240-262 (1992)). COPD is a slowly progressive and irreversible disorder characterized by the functional abnormality of airway obstruction. TGF-β has been hypothesized to be involved in airway remodeling found in chronic airway inflammatory disorders such as COPD (e.g., Takizawa, H. *Int. J. Mol. Med.* 1: 367-378 (1998); Ning, W. et al., *Proc. Natl. Acad. Sci. USA* 101: 14895-14900 (2004)).

Hepatic stellate cells (HSC) are the major source of extracellular matrix proteins in hepatic fibrosis. Extracellular matrix production by activated hepatic stellate cells is markedly increased through the action of TGF-β1 (e.g., Friedman, S. L., *Prog. Liver Dis.* 14: 101-130 (1996); Pietrangelo, A., *Semin. Liver Dis.* 16: 13-30 (1996)). Transgenic mice that overexpress TGF-β1 in the liver develop hepatic fibrosis as well as extrahepatic pathologies such as renal fibrosis (e.g., Sanderson, N. et al., *Proc. Natl. Acad. Sci. USA* 92: 2572-2576 (1995)).

TGF-β1 and its receptors are overexpressed in injured blood vessels and in fibroproliferative vascular lesions leading to overproduction of extracellular matrix (e.g., Saltis, J. et al., *Clin. Exp. Pharmacol. Physiol.* 23: 193-200 (1996); McCaffrey, T. A. et al., *J. Clin. Invest.* 96: 2667-2675 (1995)).

Anti-TGF-β antibodies reduce scar formation and improve the cytoarchitecture of the neodermis in rats (e.g., Shah, M., *J. Cell. Sci.* 108: 985-1002 (1995)), improve healing of corneal wounds in rabbits (e.g., Moller-Pedersen, T., *Curr. Eye Res.* 17: 736-747 (1998)), and accelerate wound healing of gastric ulcers in rats (e.g., Ernst, H., *Gut* 39: 172-175 (1996)).

Radiation fibrosis is a frequent sequel of therapeutic or accidental radiation overexposure in normal human tissues. TGF-β1 plays a central role in the initiation, development, and persistence of radiation fibrosis, as has been reviewed recently (e.g., Martin, M. et al., *Int. J. Radiat. Oncol. Biol. Phys.* 47: 277-290 (2000)).

Organ transplantation is complicated in many instances by chronic rejection and for some organs such as the kidney, it is the major forms of graft loss. In human patients, chronic rejection of lung and kidney transplants is associated with increased expression of TGF-β within the tissue (e.g., El- Gamel, A. et al., *Eur J. Cardiothorac. Surg.* 13: 424-430 (1998); Shihab, F. S. et al., *J. Am. Soc. Nephrol.* 6: 286-294 (1995)).

TGF-β is implicated in peritoneal adhesions (e.g., Saed, G M. et al., *Wound Repair Regeneration* 7: 504-510 (1999)). The peritoneal and sub-dermal fibrotic adhesions could be prevented by inhibitors of ALK5 and/or ALK4.

The tumor cells and the stromal cells within the tumors in late stages of various cancers generally overexpress TGF-β. This leads to stimulation of angiogenesis and cell motility, suppression of the immune system, and increased interaction of tumor cells with the extracellular matrix (e.g., Hojo, M. et al., *Nature* 397: 530-534 (1999)). Consequently, the tumor cells become more invasive and metastasize to distant organs (e.g., Maehara, Y. et al., *J. Clin. Oncol.* 17: 607-614 (1999); Picon, A. et al., *Cancer Epidemiol. Biomarkers Prev.* 7: 497-504 (1998)).

Plasminogen activator inhibitor-1 (PAI-1) is the major physiological inhibitor of both tissue-type plasminogen activator and urokinase-type plasminogen activator. Elevated levels of PAI-1 are associated with thrombosis and vascular disease, suggesting that high plasma PAI-1 may promote a hypercoagulable state by disrupting the natural balance between fibrinolysis and coagulation (e.g., Vaughan, D. E., *J. Invest. Med.* 46: 370-376 (1998)). It is known that TGF-β stimulates the expression of PAI-1 (e.g., Dennler, S. et al., *EMBO J.* 17: 3091-3100 (1998)). Accordingly, inhibition of the production of PAI-1 with an inhibitor of the TGF-β signaling pathway could produce a novel fibrinolytic therapy.

Activin signaling and overexpression of activin is linked to pathological disorders that involve extracellular matrix accumulation and fibrosis (e.g., Matsuse, T. et al., *Am. J. Respir. Cell Mol. Biol.* 13: 17-24 (1995); Inoue, S. et al., *Biochem. Biophys. Res. Comm.* 205: 441-448 (1994); Matsuse, T. et al., *Am. J. Pathol.* 148: 707-713 (1996); De Bleser et al., *Hepatology* 26: 905-912 (1997); Pawlowski, J. E., et al., *J. Clin. Invest.* 100: 639-648 (1997); Sugiyama, M. et al., *Gastroenterology* 114: 550-558 (1998); Munz, B. et al., *EMBO J.* 18: 5205-5215 (1999)), inflammatory responses (e.g., Rosendahl, A. et al., *Am. J. Respir. Cell Mol. Biol.* 25: 60-68 (2001), cachexia or wasting (Matzuk, M. M. et al., *Proc. Natl. Acd. Sci. USA* 91: 8817-8821 (1994); Coerver, K. A. et al., *Mol. Endocrinol.* 10: 534-543 (1996); Cipriano, S. C. et al., *Endocrinology* 141: 2319-2327 (2000)), diseases or pathological responses in the central nervous system (e.g., Logan, A. et al., *Eur. J. Neurosci.* 11: 2367-2374 (1999); Logan, A. et al., *Exp. Neurol.* 159: 504-510 (1999); Masliah, E. et al., *Neurochem. Int.* 39: 393-400 (2001); De Groot, C. J. A. et al., *J. Neuropathol. Exp. Neurol.* 58: 174-187 (1999); John, G R. et al., *Nat. Med.* 8: 1115-1121 (2002)) and hypertension (e.g., Dahly, A. J. et al., *Am. J. Physiol. Regul. Integr. Comp. Physiol.* 283: R757—767 (2002)). Studies have shown that TGF-β and activin can act synergistically to induce extracellular matrix production (e.g., Sugiyama, M. et al., *Gastroenterology* 114; 550-558 (1998)).

Therefore, it becomes evident that inhibition of ALK5 and/or ALK4 phosphorylation of Smad2 and Smad3 by the preferred compounds of this invention could treat and prevent disorders involving these signaling pathways.

WO 00/61576 and US 2003/0149277 A1 disclose triarylimidazole derivatives and their use as ALK5 inhibitors. WO 01/62756 A1 discloses pyridinylimidazole derivatives and their use as ALK5 inhibitors. WO 02/055077 A1 discloses use of imidazolyl cyclic acetal derivatives as ALK5 inhibitors. WO 03/087304 A2 discloses tri-substituted heteroaryls and their use as ALK5 and/or ALK4 inhibitors. WO 2005/103028 A1 and U.S. Pat. No. 7,407,958 B2 disclose 2-pyridyl substituted imidazoles as ALK5 and/or ALK4 inhibitors. Especially, one of the representative compounds claimed in WO 2005/103028 A1 and U.S. Pat. No. 7,407,958 B2, IN-1130, demonstrated its use in several animal models as ALK5 and/or ALK4 inhibitors. IN-1130 effectively suppressed renal fibrosis induced by unilateral ureteral obstruction (UUO) in rats (Moon, J.-A. et al., *Kidney Int.* 70: 1234-1243 (2006)), ameliorated experimental autoimmune encephalomyelitis (EAE) in SBE-luc and GFAP-luc mice immunized with $MOG_{35-55}$ (Luo, J. et al., *J. Clin. Invest.* 117: 3306-3315 (2007)), lessened tunical fibrosis and corrected penile curvature in rats (Ryu, J.-K. et al., *J. Sex. Med.* 6: 1284-1296 (2009)), and dramatically reduced tumor volume with an enhanced immune response in mice treated with murine prostate cancer cell line Tramp C2 (Lee, G. T. et al., *J. Urol.* 180: 2660-2667 (2008)). And, also, US 2008/0319012 A1 discloses 2-pyridyl substituted imidazoles as ALK5 and/or ALK4 inhibitors. Especially, one of the representative compounds claimed in US 2008/0319012 A1, IN-1233, demonstrated its use in several animal models as ALK5 and/or ALK4 inhibitors. IN-1233 effectively prevented the development and progression of pulmonary arterial hypertension in the monocrotaline rat model through the inhibition of TGF-β signaling (Long, L. et al., *Circulation* 119: 566-576 (2009)) and also prevented granulation tissue formation after bare metallic stent placement in a rat urethral model (Kim, J. H. et al., *Radiology* 255: 75-82 (2010)).

SUMMARY

Surprisingly, it has now been discovered that a class of 2-pyridyl substituted imidazoles function as potent and selective inhibitors of ALK5 and/or ALK4 and, therefore, have utility in the treatment and prevention of various disease states mediated by ALK5 and/or ALK4, such as glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, disorders of the biliary tree, pulmonary fibrosis, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, fibrotic cancers, tumor metastasis growth, radiation-induced fibrosis, and thrombosis.

BRIEF DESCRIPTION OF THE DRAWINGS

The aforementioned aspects and other features of the present invention will be explained in the following description, taken in conjunction with the accompanying drawings, wherein.

Figure 1:
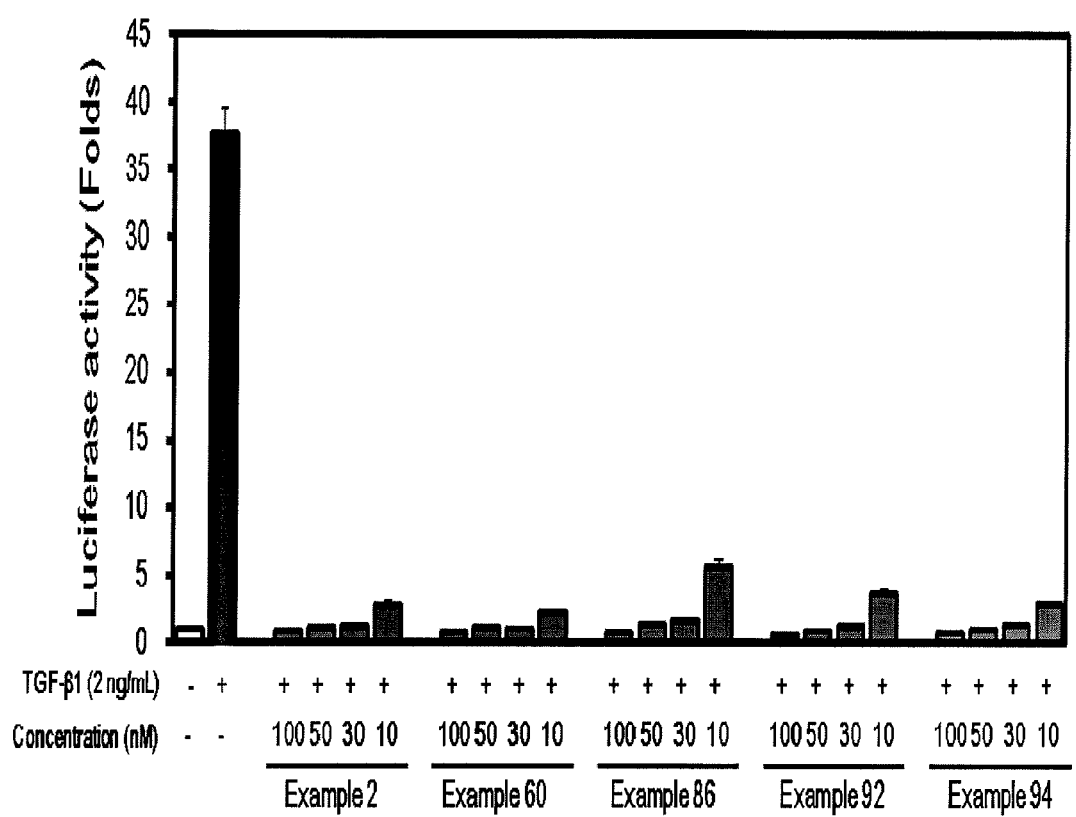
FIG. 1 shows effect of Examples 2, 60, 86, 92, and 94 on the TGF-β1-induced 3TP-Luc reporter activity in HaCaT-3TP-Luc cells.
Figure 2:
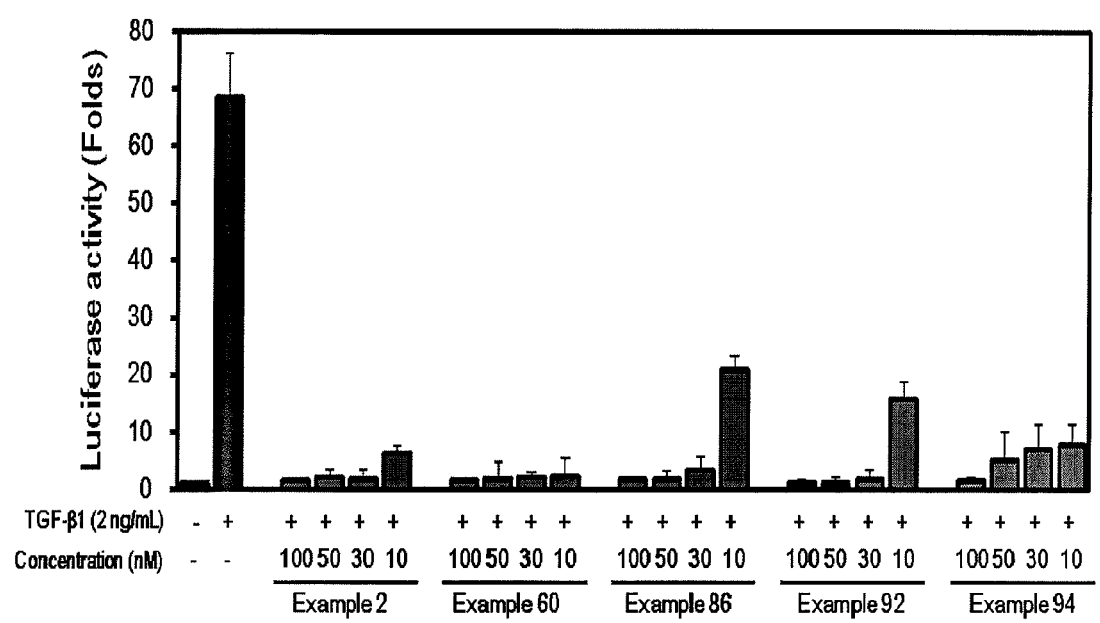
FIG. 2 shows effect of Examples 2, 60, 86, 92, and 94 on the TGF-β1-induced 3TP-Luc reporter activity in 4T1-3TP-Luc cells.
Figure 3A:
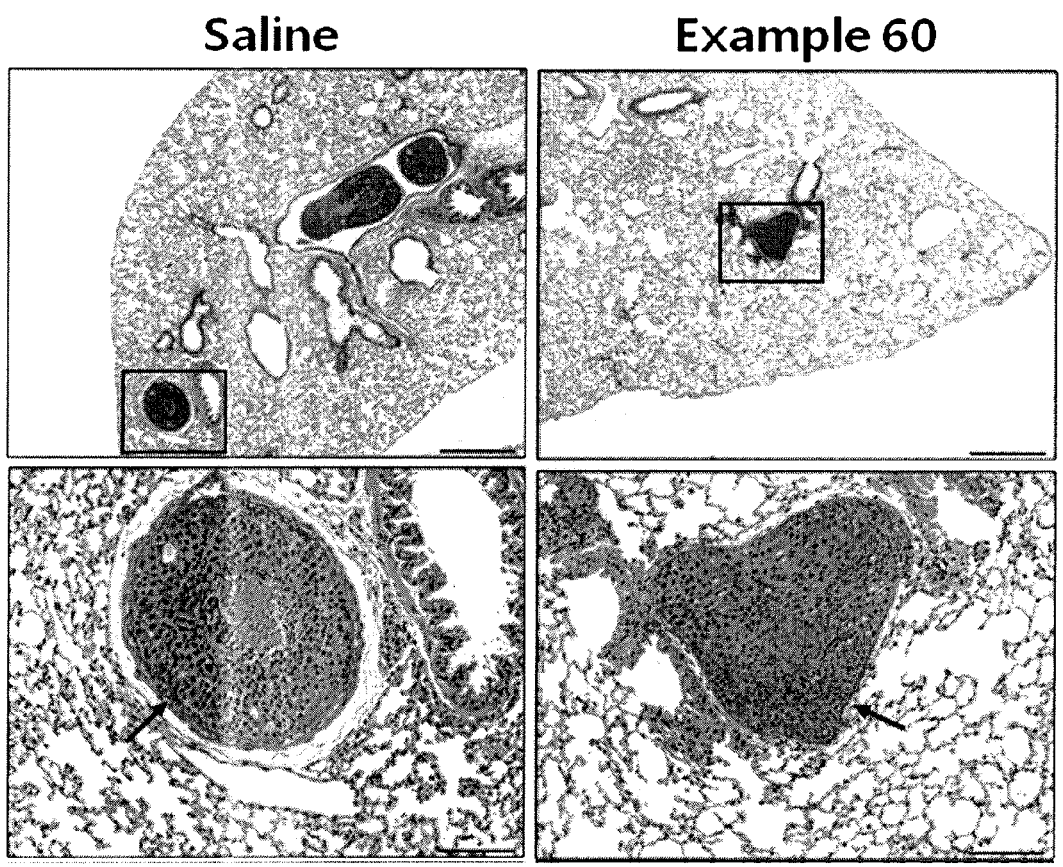
FIGS. 3A, 3B, 3C, and 3D show effect of Example 60 on the breast tumor metastasis to the lung in MMTV/c-Neu mice in vivo. Tumor-bearing MMTV/c-Neu mice were treated intraperitoneally with either saline (vehicle) or Example 60 (40 mg/kg) every other day for 3 weeks. (3A). Hematoxylin and eosin (H & E) staining of mammary tumor and lung tissues. (3B). Number of histologically detectable metastastic lesions in the lung. Data represents the mean±SD (n=2 per groups). (3C). Volume of mammary tumor. (3D). β-Casein mRNA level.
Figure 3B:
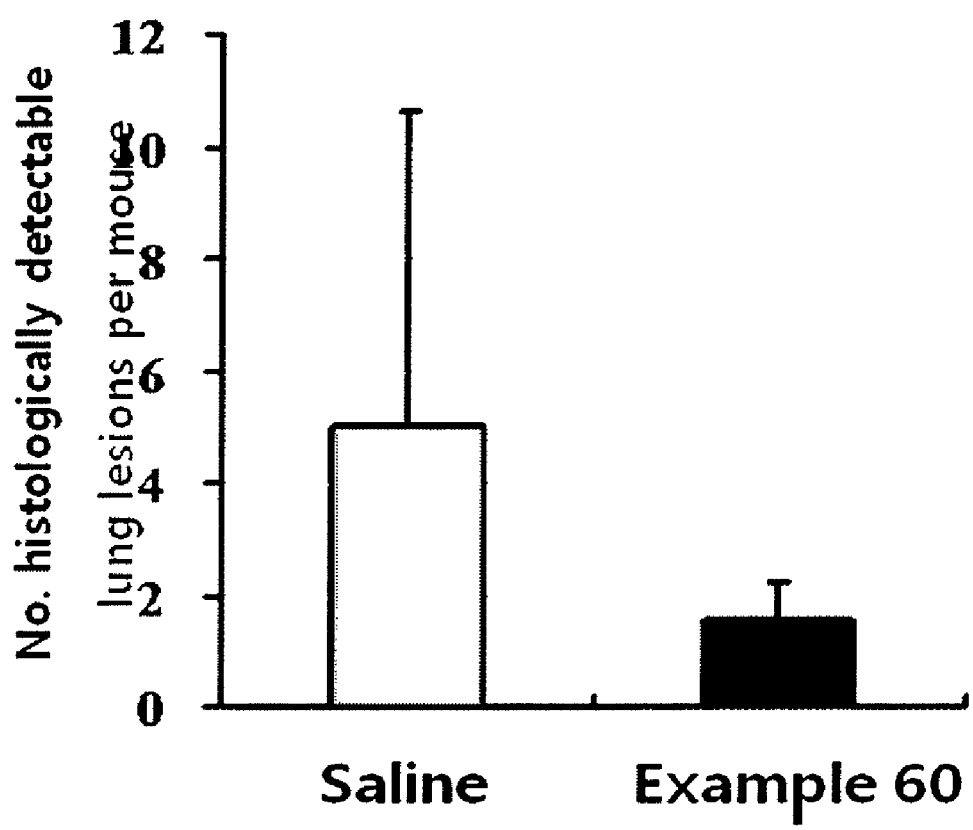
Figure 3C:
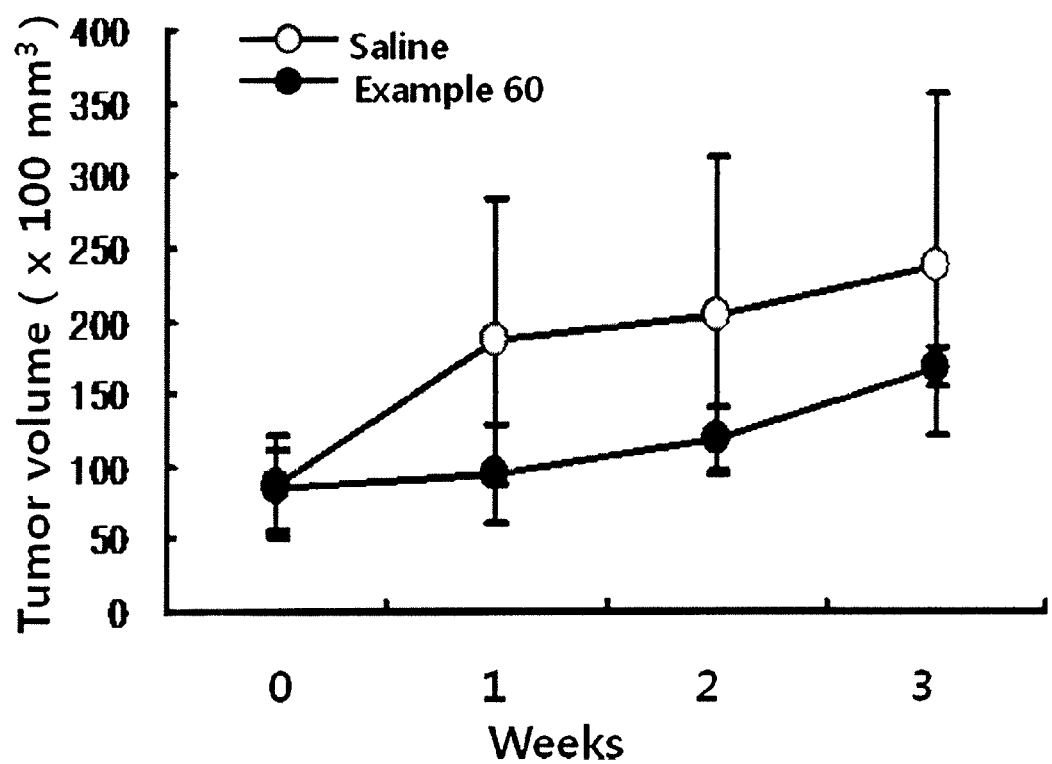
Figure 3D:
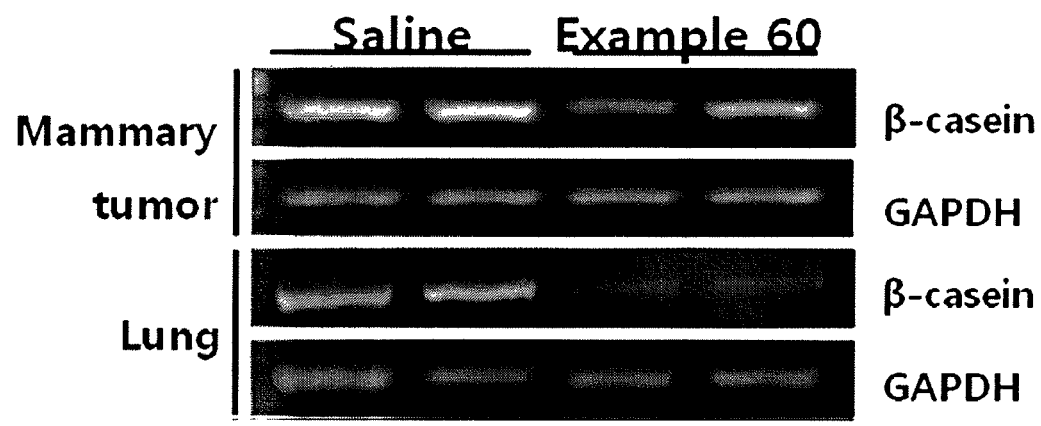
Figure 3D:
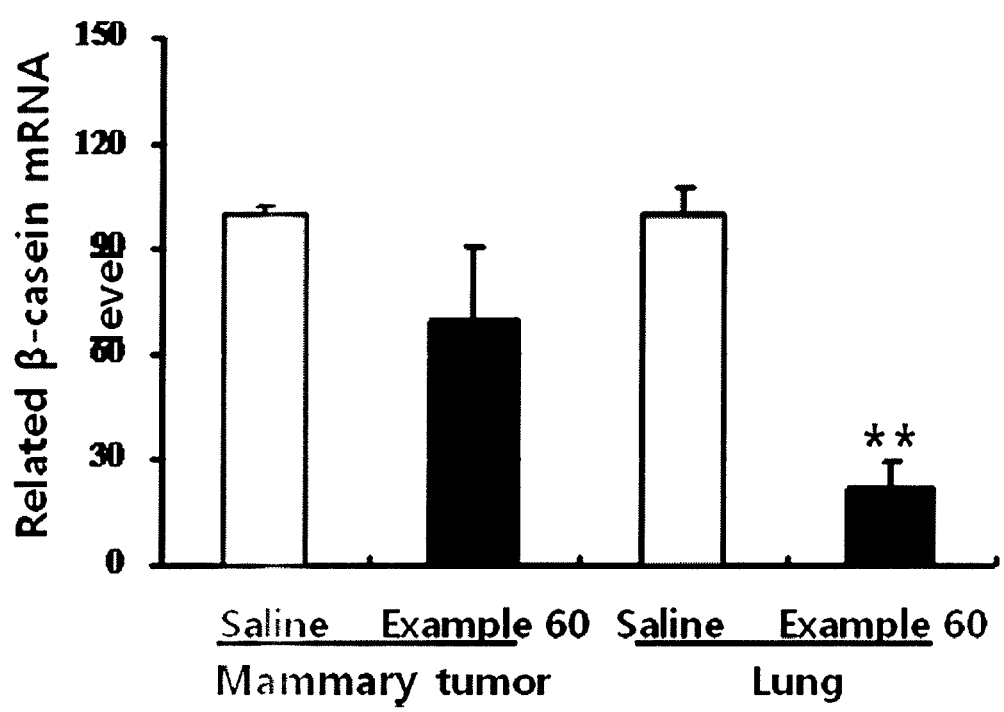
Figure 4A:
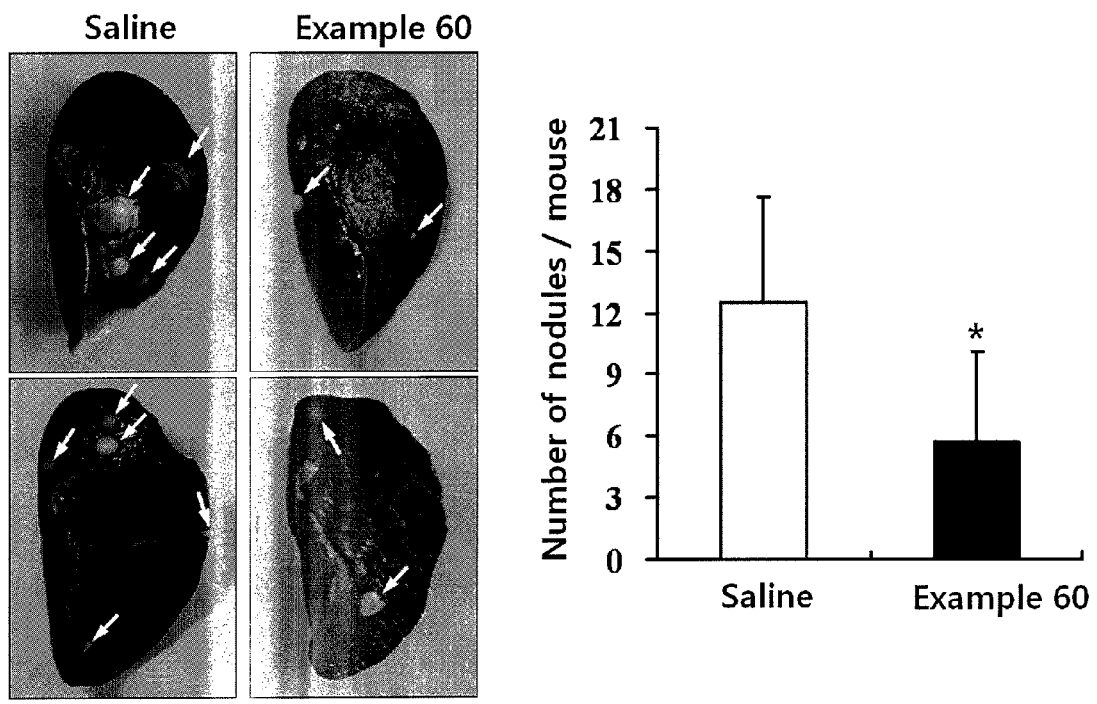
FIGS. 4A and 4B show effect of Example 60 on the breast tumor metastasis to the lung in the Balb/c xenograft mice in vivo. Tumor-bearing Balb/c xenograft mice were treated intraperitoneally with either saline (vehicle) or Example 60 (40 mg/kg) every other day for 2.5 weeks. (4A). Number of metastastic nodules on lung surface (white arrows, left panel). (4B). Volume of primary tumor.
Figure 4B:
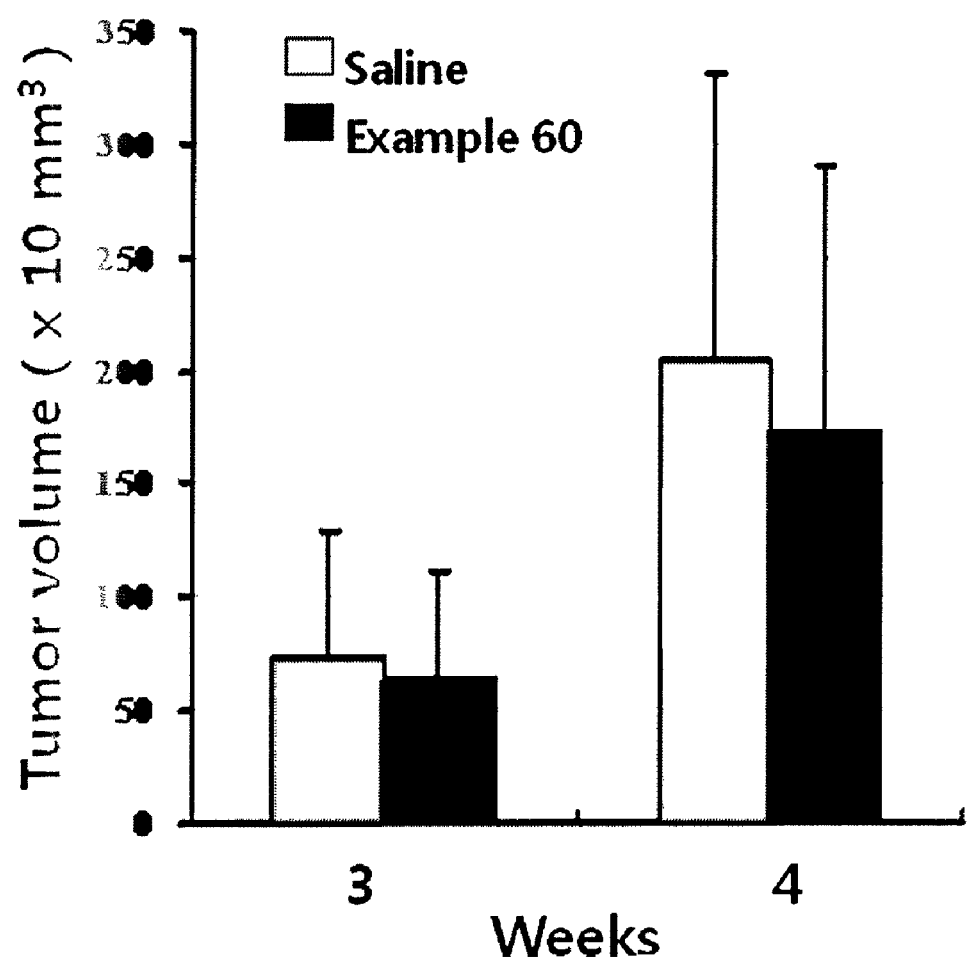

Table 1 shows structures and $^1$H NMR and MS spectral data of Examples 1-139, and Table 2 shows structures and $^1$H NMR and MS spectral data of Examples 140-153.

DETAILED DESCRIPTION OF PREFERRED EMBODIMENTS

In an embodiment of the present invention, there is provided a compound of formula (I) or a pharmaceutically acceptable salt thereof:

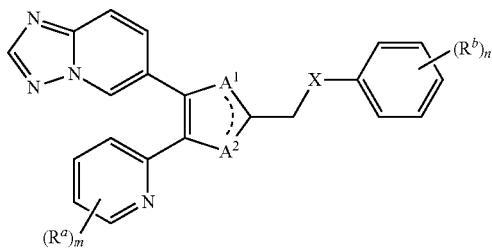

(I)

wherein each $R^a$ is independently H, halo, $C_{1-6}$alkyl, $C_{1-6}$haloalkyl, $C_{3-6}$cycloalkyl, OH, —O—$C_{1-6}$alkyl, —O—$C_{3-6}$cycloalkyl, $NH_2$, —NH—$C_{1-6}$alkyl, —NH—$C_{1-6}$haloalkyl, —NH—$C_{3-6}$cycloalkyl, —S—$C_{1-6}$alkyl, —S—$C_{3-6}$cycloalkyl, CN, or $NO_2$;

m is 0, 1, 2, 3, or 4;

one of $A^1$ and $A^2$ is N and the other is $NR^1$, wherein $R^1$ is H, OH, $C_{1-6}$alkyl, $C_{1-6}$haloalkyl, or $C_{3-6}$cycloalkyl;

X is a bond, —$(CH_2)_p$—, —$NR^2$—, —O—, or —S—, wherein p is 0 or 1, and $R^2$ is H or $C_{1-3}$alkyl;

each $R^b$ is independently H, halo, $C_{1-6}$alkyl, $C_{1-6}$haloalkyl, $C_{3-6}$cycloalkyl, $C_{2-6}$alkenyl, $C_{2-6}$alkynyl, —$(CH_2)_q$—$OR^3$, —$(CH_2)_q$—$NR^3R^4$, —$(CH_2)_q$—$SR^3$, —$(CH_2)_q$—$NO_2$, —$(CH_2)_q$—CONHOH, —$(CH_2)_q$—CN, —$(CH_2)_q$—$COR^3$, —$(CH_2)_q$—$CO_2R^3$, —$(CH_2)_q$—$CONR^3R^4$, —$(CH_2)_q$-tetrazole, —$(CH_2)_q$—CH=CH—CN, —$(CH_2)_q$—CH=CH—$CO_2R^3$, —$(CH_2)_q$—CH=CH—$CONR^3R^4$, —$(CH_2)_q$—CH=CH-tetrazole, —$(CH_2)_q$—$NHCOR^3$, —$(CH_2)_q$—$NHCO_2R^3$, —$(CH_2)_q$—$CONHSO_2R^3$, —$(CH_2)_q$—$NHSO_2R^3$, —$(CH_2)_q$—C≡C—CN, —$(CH_2)_q$—C≡C—$CO_2R^3$, —$(CH_2)_q$—C≡C—$CONR^3R^4$, —$(CH_2)_q$—C≡C-tetrazole, —$(CH_2)_q$—$SOR^5$, —$(CH_2)_q$—$SO_2R^5$, or —$(CH_2)_r$—$(OR^3)_2$, wherein $R^3$ and $R^4$ are independently H, $C_{1-6}$alkyl, $C_{1-6}$haloalkyl, or $C_{3-6}$cycloalkyl; or taken together with the nitrogen atom to which they are attached form a mono-cyclic ring such as imidazole, pyrrolidine, piperidine, morpholine, piperazine and homopiperazine; $R^5$ is $C_{1-6}$alkyl, $C_{1-6}$haloalkyl, or $C_{3-6}$cycloalkyl; q is 0, 1, 2, 3, or 4; and r is 1, 2, 3, or 4;

n is 0, 1, 2, 3, 4, or 5.

As used herein, the double bond indicated by the dotted lines of formula (I), represent the possible tautomeric ring forms of the compounds falling within the scope of this invention, the double bond being to the unsubstituted nitrogen.

Preferably, $R^a$ is $C_{1-3}$alkyl or halo.

Preferably, m is 1 or 2.

Preferably, one of $A^1$ and $A^2$ is N and the other is $NR^1$, wherein $R^1$ is H.

Preferably, X is —$(CH_2)_p$— or —$NR^2$—, wherein p is 0 and $R^2$ is H.

Preferably, $R^b$ is halo, $C_{1-3}$alkyl, $C_{1-3}$haloalkyl, $C_{3-4}$cycloalkyl, $C_{2-4}$alkenyl, $C_{2-4}$alkynyl, —$(CH_2)_q$—$OR^3$, —$(CH_2)_q$—$NR^3R^4$, —$(CH_2)_q$—$SR^3$, —$(CH_2)_q$—CN, —$(CH_2)_q$—$COR^3$, —$(CH_2)_q$—$CO_2R^3$, —$(CH_2)_q$—$CONR^3R^4$, —$(CH_2)_q$—$NHCOR^3$, —$(CH_2)_q$—$NHSO_2R^3$, —$(CH_2)_q$—$SOR^5$, or —$(CH_2)_q$—$SO_2R^5$, wherein $R^3$ and $R^4$ are independently H, $C_{1-3}$alkyl, $C_{1-3}$haloalkyl, or $C_{3-4}$cycloalkyl; or taken together with the nitrogen atom to which they are attached form a mono-cyclic ring such as imidazole, pyrrolidine, piperidine, morpholine, piperazine and homopiperazine; $R^5$ is methyl; and q is 0, 1, or 2.

Preferably, n is 1, 2, or 3.

Specific compounds of the invention which may be mentioned include the following and pharmaceutically acceptable salts thereof:

N-((4-([1,2,4]triazolo[1,5-a]pyridin-6-yl)-5-(6-methylpyridin-2-yl)-1H-imidazol-2-yl) methyl)aniline;

N-((4-([1,2,4]triazolo[1,5-a]pyridin-6-yl)-5-(6-methylpyridin-2-yl)-1H-imidazol-2-yl)methyl)-2-fluoroaniline;

N-((4-([1,2,4]triazolo[1,5-a]pyridin-6-yl)-5-(6-methylpyridin-2-yl)-1H-imidazol-2-yl)methyl)-3-fluoroaniline;

N-((4-([1,2,4]triazolo[1,5-a]pyridin-6-yl)-5-(6-methylpyridin-2-yl)-1H-imidazol-2-yl)methyl)-4-fluoroaniline;

N-((4-([1,2,4]triazolo[1,5-a]pyridin-6-yl)-5-(6-methylpyridin-2-yl)-1H-imidazol-2-yl)methyl)-2,3-difluoroaniline;

N-((4-([1,2,4]triazolo[1,5-a]pyridin-6-yl)-5-(6-methylpyridin-2-yl)-1H-imidazol-2-yl)methyl)-3,4-difluoroaniline;

N-((4-([1,2,4]triazolo[1,5-a]pyridin-6-yl)-5-(6-methylpyridin-2-yl)-1H-imidazol-2-yl)methyl)-3,5-difluoroaniline;

N-((4-([1,2,4]triazolo[1,5-a]pyridin-6-yl)-5-(6-methylpyridin-2-yl)-1H-imidazol-2-yl)methyl)-2-chloroaniline;

N-((4-([1,2,4]triazolo[1,5-a]pyridin-6-yl)-5-(6-methylpyridin-2-yl)-1H-imidazol-2-yl)methyl)-3-chloroaniline;

N-((4-([1,2,4]triazolo[1,5-a]pyridin-6-yl)-5-(6-methylpyridin-2-yl)-1H-imidazol-2-yl)methyl)-4-chloroaniline;

N-((4-([1,2,4]triazolo[1,5-a]pyridin-6-yl)-5-(6-methylpyridin-2-yl)-1H-imidazol-2-yl)methyl)-2,3-dichloroaniline;

N-((4-([1,2,4]triazolo[1,5-a]pyridin-6-yl)-5-(6-methylpyridin-2-yl)-1H-imidazol-2-yl)methyl)-3,4-dichloroaniline;

N-((4-([1,2,4]triazolo[1,5-a]pyridin-6-yl)-5-(6-methylpyridin-2-yl)-1H-imidazol-2-yl)methyl)-3,5-dichloroaniline;

N-((4-([1,2,4]triazolo[1,5-a]pyridin-6-yl)-5-(6-methylpyridin-2-yl)-1H-imidazol-2-yl)methyl)-2-bromoaniline;

N-((4-([1,2,4]triazolo[1,5-a]pyridin-6-yl)-5-(6-methylpyridin-2-yl)-1H-imidazol-2-yl)methyl)-3-bromoaniline;

N-((4-([1,2,4]triazolo[1,5-a]pyridin-6-yl)-5-(6-methylpyridin-2-yl)-1H-imidazol-2-yl)methyl)-4-bromoaniline;

N-((4-([1,2,4]triazolo[1,5-a]pyridin-6-yl)-5-(6-methylpyridin-2-yl)-1H-imidazol-2-yl)methyl)-2-methylaniline;
N-((4-([1,2,4]triazolo[1,5-a]pyridin-6-yl)-5-(6-methylpyridin-2-yl)-1H-imidazol-2-yl)methyl)-3-methylaniline;
N-((4-([1,2,4]triazolo[1,5-a]pyridin-6-yl)-5-(6-methylpyridin-2-yl)-1H-imidazol-2-yl)methyl)-4-methylaniline;
N-((4-([1,2,4]triazolo[1,5-a]pyridin-6-yl)-5-(6-methylpyridin-2-yl)-1H-imidazol-2-yl)methyl)-2,3-dimethylaniline;
N-((4-([1,2,4]triazolo[1,5-a]pyridin-6-yl)-5-(6-methylpyridin-2-yl)-1H-imidazol-2-yl)methyl)-3,4-dimethylaniline;
N-((4-([1,2,4]triazolo[1,5-a]pyridin-6-yl)-5-(6-methylpyridin-2-yl)-1H-imidazol-2-yl)methyl)-3,5-dimethylaniline;
N-((4-([1,2,4]triazolo[1,5-a]pyridin-6-yl)-5-(6-methylpyridin-2-yl)-1H-imidazol-2-yl)methyl)-2-ethylaniline;
N-((4-([1,2,4]triazolo[1,5-a]pyridin-6-yl)-5-(6-methylpyridin-2-yl)-1H-imidazol-2-yl)methyl)-3-ethylaniline;
N-((4-([1,2,4]triazolo[1,5-a]pyridin-6-yl)-5-(6-methylpyridin-2-yl)-1H-imidazol-2-yl)methyl)-2-isopropylaniline;
N-((4-([1,2,4]triazolo[1,5-a]pyridin-6-yl)-5-(6-methylpyridin-2-yl)-1H-imidazol-2-yl)methyl)-3-isopropylaniline;
N-((4-([1,2,4]triazolo[1,5-a]pyridin-6-yl)-5-(6-methylpyridin-2-yl)-1H-imidazol-2-yl)methyl)-4-isopropylaniline;
N-((4-([1,2,4]triazolo[1,5-a]pyridin-6-yl)-5-(6-methylpyridin-2-yl)-1H-imidazol-2-yl)methyl)-2-vinylaniline;
N-((4-([1,2,4]triazolo[1,5-a]pyridin-6-yl)-5-(6-methylpyridin-2-yl)-1H-imidazol-2-yl)methyl)-3-vinylaniline;
N-((4-([1,2,4]triazolo[1,5-a]pyridin-6-yl)-5-(6-methylpyridin-2-yl)-1H-imidazol-2-yl)methyl)-4-vinylaniline;
N-((4-([1,2,4]triazolo[1,5-a]pyridin-6-yl)-5-(6-methylpyridin-2-yl)-1H-imidazol-2-yl)methyl)-3-ethynylaniline;
N-((4-([1,2,4]triazolo[1,5-a]pyridin-6-yl)-5-(6-methylpyridin-2-yl)-1H-imidazol-2-yl)methyl)-2-methoxyaniline;
N-((4-([1,2,4]triazolo[1,5-a]pyridin-6-yl)-5-(6-methylpyridin-2-yl)-1H-imidazol-2-yl)methyl)-3-methoxyaniline;
N-((4-([1,2,4]triazolo[1,5-a]pyridin-6-yl)-5-(6-methylpyridin-2-yl)-1H-imidazol-2-yl)methyl)-4-methoxyaniline;
N-((4-([1,2,4]triazolo[1,5-a]pyridin-6-yl)-5-(6-methylpyridin-2-yl)-1H-imidazol-2-yl)methyl)-2,3-dimethoxyaniline;
N-((4-([1,2,4]triazolo[1,5-a]pyridin-6-yl)-5-(6-methylpyridin-2-yl)-1H-imidazol-2-yl)methyl)-3,4-dimethoxyaniline;
N-((4-([1,2,4]triazolo[1,5-a]pyridin-6-yl)-5-(6-methylpyridin-2-yl)-1H-imidazol-2-yl)methyl)-3,5-dimethoxyaniline;
N-((4-([1,2,4]triazolo[1,5-a]pyridin-6-yl)-5-(6-methylpyridin-2-yl)-1H-imidazol-2-yl)methyl)-2-(methoxymethyl)aniline;
N-((4-([1,2,4]triazolo[1,5-a]pyridin-6-yl)-5-(6-methylpyridin-2-yl)-1H-imidazol-2-yl)methyl)-3-(methoxymethyl)aniline;
N-((4-([1,2,4]triazolo[1,5-a]pyridin-6-yl)-5-(6-methylpyridin-2-yl)-1H-imidazol-2-yl)methyl)-4-(methoxymethyl)aniline;
N-((4-([1,2,4]triazolo[1,5-a]pyridin-6-yl)-5-(6-methylpyridin-2-yl)-1H-imidazol-2-yl)methyl)-2-(trifluoromethoxy)aniline;
N-((4-([1,2,4]triazolo[1,5-a]pyridin-6-yl)-5-(6-methylpyridin-2-yl)-1H-imidazol-2-yl)methyl)-3-(trifluoromethoxy)aniline;
N-((4-([1,2,4]triazolo[1,5-a]pyridin-6-yl)-5-(6-methylpyridin-2-yl)-1H-imidazol-2-yl)methyl)-4-(trifluoromethoxy)aniline;
N-((4-([1,2,4]triazolo[1,5-a]pyridin-6-yl)-5-(6-methylpyridin-2-yl)-1H-imidazol-2-yl)methyl)-2-(methylthio)aniline;
N-((4-([1,2,4]triazolo[1,5-a]pyridin-6-yl)-5-(6-methylpyridin-2-yl)-1H-imidazol-2-yl)methyl)-3-(methylthio)aniline;
N-((4-([1,2,4]triazolo[1,5-a]pyridin-6-yl)-5-(6-methylpyridin-2-yl)-1H-imidazol-2-yl)methyl)-4-(methylthio)aniline;
2-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)benzonitrile;
4-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)phthalonitrile;
2-((4-([1,2,4]triazolo[1,5-a]pyridin-6-yl)-5-(6-methylpyridin-2-yl)-1H-imidazol-2-yl)methylamino)benzamide;
3-((4-([1,2,4]triazolo[1,5-a]pyridin-6-yl)-5-(6-methylpyridin-2-yl)-1H-imidazol-2-yl)methylamino)benzamide;
4-((4-([1,2,4]triazolo[1,5-a]pyridin-6-yl)-5-(6-methylpyridin-2-yl)-1H-imidazol-2-yl)methylamino)benzamide;
2-(3-((4-([1,2,4]triazolo[1,5-a]pyridin-6-yl)-5-(6-methylpyridin-2-yl)-1H-imidazol-2-yl)methylamino)phenyl)acetonitrile;
2-(4-((4-([1,2,4]triazolo[1,5-a]pyridin-6-yl)-5-(6-methylpyridin-2-yl)-1H-imidazol-2-yl)methylamino)phenyl)acetonitrile;
1-(3-((4-([1,2,4]triazolo[1,5-a]pyridin-6-yl)-5-(6-methylpyridin-2-yl)-1H-imidazol-2-yl)methylamino)phenyl)ethanone;
1-(4-((4-([1,2,4]triazolo[1,5-a]pyridin-6-yl)-5-(6-methylpyridin-2-yl)-1H-imidazol-2-yl)methylamino)phenyl)ethanone;
Methyl 3-((4-([1,2,4]triazolo[1,5-a]pyridin-6-yl)-5-(6-methylpyridin-2-yl)-1H-imidazol-2-yl)methylamino)benzoate;
Methyl 4-((4-([1,2,4]triazolo[1,5-a]pyridin-6-yl)-5-(6-methylpyridin-2-yl)-1H-imidazol-2-yl)methylamino)benzoate;
N-(2-((4-([1,2,4]triazolo[1,5-a]pyridin-6-yl)-5-(6-methylpyridin-2-yl)-1H-imidazol-2-yl)methylamino)phenyl)acetamide;
N-(3-((4-([1,2,4]triazolo[1,5-a]pyridin-6-yl)-5-(6-methylpyridin-2-yl)-1H-imidazol-2-yl)methylamino)phenyl)acetamide;
N-(4-((4-([1,2,4]triazolo[1,5-a]pyridin-6-yl)-5-(6-methylpyridin-2-yl)-1H-imidazol-2-yl)methylamino)phenyl)acetamide;
N-(2-((4-([1,2,4]triazolo[1,5-a]pyridin-6-yl)-5-(6-methylpyridin-2-yl)-1H-imidazol-2-yl)methylamino)phenyl)methanesulfonamide;
N-(3-((4-([1,2,4]triazolo[1,5-a]pyridin-6-yl)-5-(6-methylpyridin-2-yl)-1H-imidazol-2-yl)methyl amino)phenyl)methanesulfonamide;
N-(4-((4-([1,2,4]triazolo[1,5-a]pyridin-6-yl)-5-(6-methylpyridin-2-yl)-1H-imidazol-2-yl)methylamino)phenyl)methanesulfonamide;
$N^1$-((4-([1,2,4]triazolo[1,5-a]pyridin-6-yl)-5-(6-methylpyridin-2-yl)-1H-imidazol-2-yl)methyl)-$N^2,N^2$-dimethylbenzene-1,2-diamine;
$N^1$-((4-([1,2,4]triazolo[1,5-a]pyridin-6-yl)-5-(6-methylpyridin-2-yl)-1H-imidazol-2-yl)methyl)-$N^3,N^3$-dimethylbenzene-1,3-diamine;
N-((4-([1,2,4]triazolo[1,5-a]pyridin-6-yl)-5-(6-methylpyridin-2-yl)-1H-imidazol-2-yl)methyl)-2-(pyrrolidin-1-yl)aniline;

N-((4-([1,2,4]triazolo[1,5-a]pyridin-6-yl)-5-(6-methylpyridin-2-yl)-1H-imidazol-2-yl)methyl)-2-morpholinoaniline;
N-((4-([1,2,4]triazolo[1,5-a]pyridin-6-yl)-5-(6-methylpyridin-2-yl)-1H-imidazol-2-yl)methyl)-3-morpholinoaniline;
$N^3$-((4-([1,2,4]triazolo[1,5-a]pyridin-6-yl)-5-(6-methylpyridin-2-yl)-1H-imidazol-2-yl)methyl)-4-fluoro-$N^1$,$N^1$-dimethylbenzene-1,3-diamine;
3-((4-([1,2,4]triazolo[1,5-a]pyridin-6-yl)-5-(6-methylpyridin-2-yl)-1H-imidazol-2-yl)methylamino)-5-(dimethylamino)benzonitrile;
3-((4-([1,2,4]triazolo[1,5-a]pyridin-6-yl)-5-(6-methylpyridin-2-yl)-1H-imidazol-2-yl)methylamino)-4-(dimethylamino)benzonitrile;
N-((4-([1,2,4]triazolo[1,5-a]pyridin-6-yl)-5-(6-methylpyridin-2-yl)-1H-imidazol-2-yl)methyl)-2-((dimethylamino)methyl)aniline;
N-((4-([1,2,4]triazolo[1,5-a]pyridin-6-yl)-5-(6-methylpyridin-2-yl)-1H-imidazol-2-yl)methyl)-3-((dimethylamino)methyl)aniline;
N-((4-([1,2,4]triazolo[1,5-a]pyridin-6-yl)-5-(6-methylpyridin-2-yl)-1H-imidazol-2-yl)methyl)-2-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-(morpholinomethyl)aniline;
N-((4-([1,2,4]triazolo[1,5-a]pyridin-6-yl)-5-(6-methylpyridin-2-yl)-1H-imidazol-2-yl)methyl)-3-(morpholinomethyl)aniline;
N-((4-([1,2,4]triazolo[1,5-a]pyridin-6-yl)-5-(6-methylpyridin-2-yl)-1H-imidazol-2-yl)methyl)-5-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-3-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-fluoro-3-(morpholinomethyl)aniline;
3-((4-([1,2,4]triazolo[1,5-a]pyridin-6-yl)-5-(6-methylpyridin-2-yl)-1H-imidazol-2-yl)methylamino)-4-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-2-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-5-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-4-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-2-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-5-(pyrrolidin-1-ylmethyl)benzonitrile;
3-((4-([1,2,4]triazolo[1,5-a]pyridin-6-yl)-5-(6-methylpyridin-2-yl)-1H-imidazol-2-yl)methylamino)-4-(morpholinomethyl)benzonitrile;
3-((4-([1,2,4]triazolo[1,5-a]pyridin-6-yl)-5-(6-methylpyridin-2-yl)-1H-imidazol-2-yl)methylamino)-2-(morpholinomethyl)benzonitrile;
3-((4-([1,2,4]triazolo[1,5-a]pyridin-6-yl)-5-(6-methylpyridin-2-yl)-1H-imidazol-2-yl)methylamino)-5-(morpholinomethyl)benzonitrile;
N-((4-([1,2,4]triazolo[1,5-a]pyridin-6-yl)-5-(6-methylpyridin-2-yl)-1H-imidazol-2-yl)methyl)-2-(2-(dimethylamino)ethylaniline;
N-((4-([1,2,4]triazolo[1,5-a]pyridin-6-yl)-5-(6-methylpyridin-2-yl)-1H-imidazol-2-yl)methyl)-3-(2-(dimethylamino)ethylaniline;
3-((4-([1,2,4]triazolo[1,5-a]pyridin-6-yl)-5-(6-ethylpyridin-2-yl)-1H-imidazol-2-yl)methylamino)benzonitrile;
N-((4-([1,2,4]triazolo[1,5-a]pyridin-6-yl)-5-(6-ethylpyridin-2-yl)-1H-imidazol-2-yl)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-N-methylaniline;
3-((4-([1,2,4]triazolo[1,5-a]pyridin-6-yl)-5-(6-methylpyridin-2-yl)-1H-imidazol-2-yl)methyl)(methyl)amino)benzonitrile;
3-((4-([1,2,4]triazolo[1,5-a]pyridin-6-yl)-5-(6-methylpyridin-2-yl)-1H-imidazol-2-yl)methyl)(methyl)amino)benzamide;
6-(2-benzyl-5-(6-methylpyridin-2-yl)-1H-imidazol-4-yl)-[1,2,4]triazolo[1,5-a]pyridine;
6-(2-(2-fluorobenzyl)-5-(6-methylpyridin-2-yl)-1H-imidazol-4-yl)-[1,2,4]triazolo[1,5-a]pyridine;
3-((4-([1,2,4]triazolo[1,5-a]pyridin-6-yl)-5-(6-methylpyridin-2-yl)-1H-imidazol-2-yl)methyl)benzonitrile;
3-((4-([1,2,4]triazolo[1,5-a]pyridin-6-yl)-5-(6-methylpyridin-2-yl)-1H-imidazol-2-yl)methyl)benzamide;
6-(5-(6-methylpyridin-2-yl)-2-(phenoxymethyl)-1H-imidazol-4-yl)-[1,2,4]triazolo[1,5-a]pyridine;
6-(2-((2-fluorophenoxy)methyl)-5-(6-methylpyridin-2-yl)-1H-imidazol-4-yl)-[1,2,4]triazolo[1,5-a]pyridine;
3-((4-([1,2,4]triazolo[1,5-a]pyridin-6-yl)-5-(6-methylpyridin-2-yl)-1H-imidazol-2-yl)methoxy)benzonitrile;
3-((4-([1,2,4]triazolo[1,5-a]pyridin-6-yl)-5-(6-methylpyridin-2-yl)-1H-imidazol-2-yl)methoxy)benzamide;
6-(5-(6-methylpyridin-2-yl)-2-(phenylthiomethyl)-1H-imidazol-4-yl)-[1,2,4]triazolo[1,5-a]pyridine;
6-(2-((2-fluorophenylthio)methyl)-5-(6-methylpyridin-2-yl)-1H-imidazol-4-yl)-1H-imidazol-4-yl)-[1,2,4]triazolo[1,5-a]pyridine.

The compounds of the present invention typically are small organic molecules (non-peptide small molecules), generally less than about 1,000 daltons in size. Preferred non-peptide small molecules have molecular weights of less than about 750 daltons, more preferably less than about 500 daltons.

Compounds of formula (I) may also be supplied in the form of a "prodrug" which is designed to release compound of formula (I) when administered to a subject. Prodrug formed designs are well known in the art, and depend on the substituents contained in compound of formula (I). For example, a substituent containing hydroxyl could be coupled to a carrier which renders the compound biologically inactive until it is removed by endogenous enzymes or, for example, by enzymes targeted to a particular receptor or location in the subject.

A compound of formula (I) that is acidic in nature (e.g., having a carboxyl or phenolic hydroxyl group) can form a pharmaceutically acceptable salt such as a sodium, potassium, calcium, or gold salt. Also within the scope of the invention are salts formed with pharmaceutically acceptable amines such as ammonia, alkyl amines, hydroxyalkylamines, and N-methylglycamine. A compound of formula (I) can be treated with an acid to form acid addition salts. Examples of such acids include hydrochloric acid, hydrobromic acid, hydroiodic acid, sulfuric acid, methanesulfonic acid, phosphoric acid, p-bromophenylsulfonic acid, carbonic acid, succinic acid, citric acid, benzoic acid, oxalic acid, malonic acid, salicyclic acid, malic acid, fumaric acid, ascorbic acid, maleic acid, acetic acid, and other mineral and organic acids well known to those skilled in the art. The acid addition salts can be prepared by treating a compound of formula (I) in its free base form with a sufficient amount of an acid (e.g., hydrochloric acid) to produce an acid addition salt (e.g., a hydrochloride salt). The acid addition salt can be converted back to its free base form by treating the salt with a suitable dilute aqueous basic solution (e.g., sodium hydroxide, sodium bicarbonate, potassium carbonate, or ammonia). Some of the compounds of this invention may be crystallized or recrystallized from solvents such as aqueous and organic solvents. In such cases solvates may be formed. This invention includes within its scope stoichiometric solvates including hydrates as well as compounds containing variable amounts of water that may be produced by processes such as lyophilization.

Compounds of formula (I) may contain one or more asymmetric centers and thus can exist as enantiomers or diastereomers. It is to be understood that the invention includes both mixtures and separate individual isomers of compounds of the formula (I). Furthermore, certain compounds of formula (I) which contain alkenyl groups may exist as cis- or trans-isomers. In each instance, the invention includes both mixtures and separate individual isomers.

Compounds of formula (I) may also exist in tautomeric forms and the invention includes both mixtures and separate individual tautomers thereof.

Also included in the invention are radiolabelled derivatives of compounds of formula (I) which are suitable for biological studies.

As used herein, the term "alkyl" group refers to a saturated aliphatic hydrocarbon group containing 1-6 carbon atoms. An alkyl group can be straight or branched. Examples of an alkyl group include, but are not limited to, methyl, ethyl, propyl, isopropyl, butyl, isobutyl, sec-butyl, tert-butyl, n-pentyl, and n-hexyl. An alkyl group can be optionally substituted with one or more substituents such as alkoxy, cycloalkoxy, amino, nitro, carboxy, cyano, halo, hydroxyl, sulfo, or mercapto.

As used herein, the term "cycloalkyl" group refers to an aliphatic carbocyclic ring of 3-6 carbon atoms. Examples of cycloalkyl groups include cyclopropyl, cyclobutyl, cyclopentyl, and cyclohexyl.

As used herein, the term "haloalkyl" group refers to an alkyl group containing one or more halogen atoms. Examples of haloalkyl groups include fluoromethyl, chloromethyl, bromomethyl, and trifluoromethyl.

As used herein, the term "halo" group refers to fluorine, chlorine, bromine, or iodine.

As used herein, the term "alkenyl" group refers to an aliphatic carbon group that contains 2-6 carbon atoms and at least one double bond. Like an alkyl group, an alkenyl group can be straight or branched. Examples of an alkenyl group include, but are not limited to, vinyl, allyl, isoprenyl, 2-butenyl, and 2-hexenyl. An alkenyl group can be optionally substituted with one or more substituents such as alkoxy, cycloalkoxy, amino, nitro, carboxy, cyano, halo, hydroxyl, sulfo, or mercapto.

As used herein, the term "alkynyl" group refers to an aliphatic carbon group that contains 2-6 carbon atoms and has at least one triple bond. An alkynyl group can be straight or branched. Examples of an alkynyl group include, but are not limited to, ethynyl, propargyl, and butynyl. An alkynyl group can be optionally substituted with one or more substituents such as alkoxy, cycloalkoxy, amino, nitro, carboxy, cyano, halo, hydroxyl, sulfo, or mercapto.

As used herein, the term "ALK5 and/or ALK4 inhibitor" refers to a compound, other than inhibitory Smads, e.g. Smad6 and Smad7, which selectively inhibits the ALK5 and/or ALK4 receptors preferentially over p38 or type II receptors.

As used herein, the term "ALK5 and/or ALK4-mediated disease state" refers to any disease state which is mediated (or modulated) by ALK5 and/or ALK4, for example, a disease which is modulated by the inhibition of the phosphorylation of Smad2 and Smad3 in the TGF-β and/or activin signaling pathways.

As used herein, the term "ulcers" is used to include, but not to be limited to, diabetic ulcers, chronic ulcers, gastric ulcers, and duodenal ulcers.

Compounds of formula (I) may be prepared by a number of known methods from commercially available or known starting materials. If the starting materials are unavailable from a commercial source, they can be prepared by procedures known in the art.

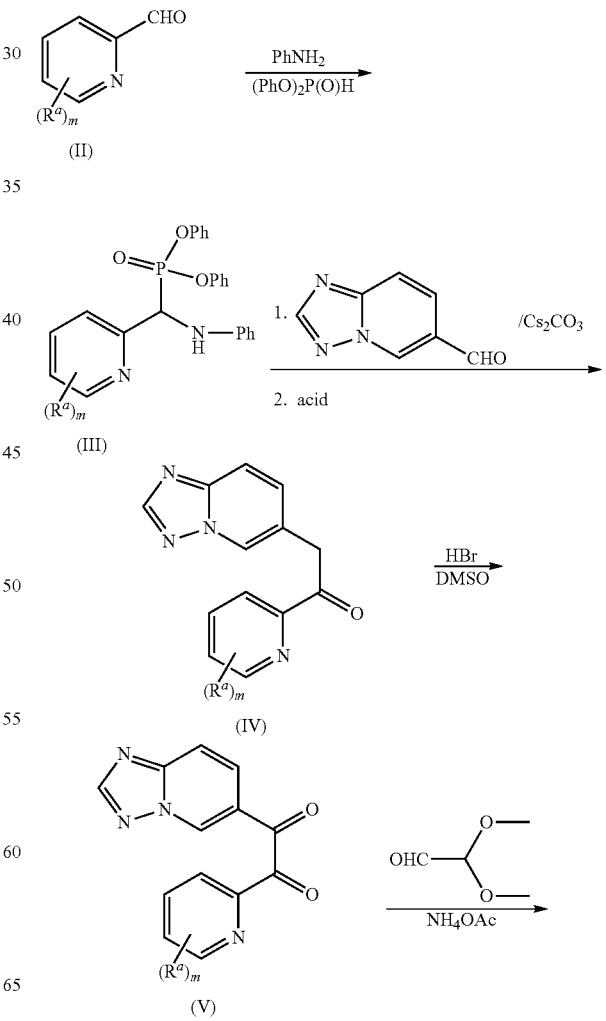

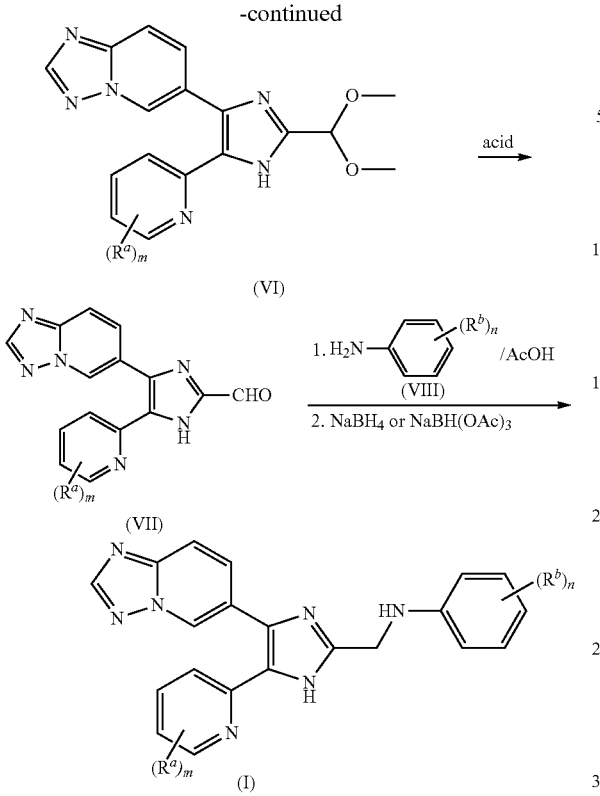

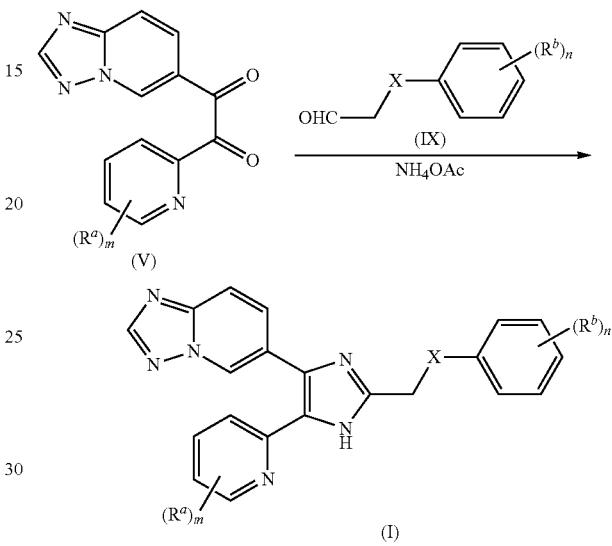

imidazole (VI), which can be hydrolyzed in acidic condition to produce an imidazole-2-carbaldehyde (VII). The imidazole-2-carbaldehyde (VII) can be coupled with $R^b$-substituted aniline (VIII) in the presence of an acid such as acetic acid to generate an immine, which can be further reduced with a reducing agent such as sodium borohydride or sodium triacetoxyborohydride to yield a compound of formula (I). $R^a$, $R^b$, m, and n have been defined as above.

In one method, compounds of formula (I) wherein $A^1$ is N and $A^2$ is NH, or $A^1$ is NH and $A^2$ is N, and X is —NH— are prepared according to Scheme 1. Specifically, $R^a$-substituted pyridine-2-carbaldehyde (II) is reacted with aniline and diphenyl phosphite to give N,P-acetal (III), which can be further coupled with [1,2,4]triazolo[1,5-a]pyridine-6-carbaldehyde followed by hydrolysis in acidic condition to produce a monoketone (IV). The monoketone (IV) may be oxidized to a diketone (V) with HBr in DMSO. This diketone (V) can then be condensed with 2,2-dimethoxyacetaldehyde in the presence of ammonium acetate to yield an acetal-protected In another method, compounds of formula (I) wherein $A^1$ is N and $A^2$ is NH, or $A^1$ is NH and $A^2$ is N, and X is —(CH$_2$)$_p$—, —NR$^2$—, —O—, or —S—, wherein p is 0 or 1, and $R^2$ is C$_{1-3}$alkyl, are prepared according to Scheme 2. The diketone (V) can be condensed with an appropriate $R^b$-substituted aldehyde (IX) in the presence of ammonium acetate to yield a compound of formula (I). $R^a$, $R^b$, m, and n have been defined as above.

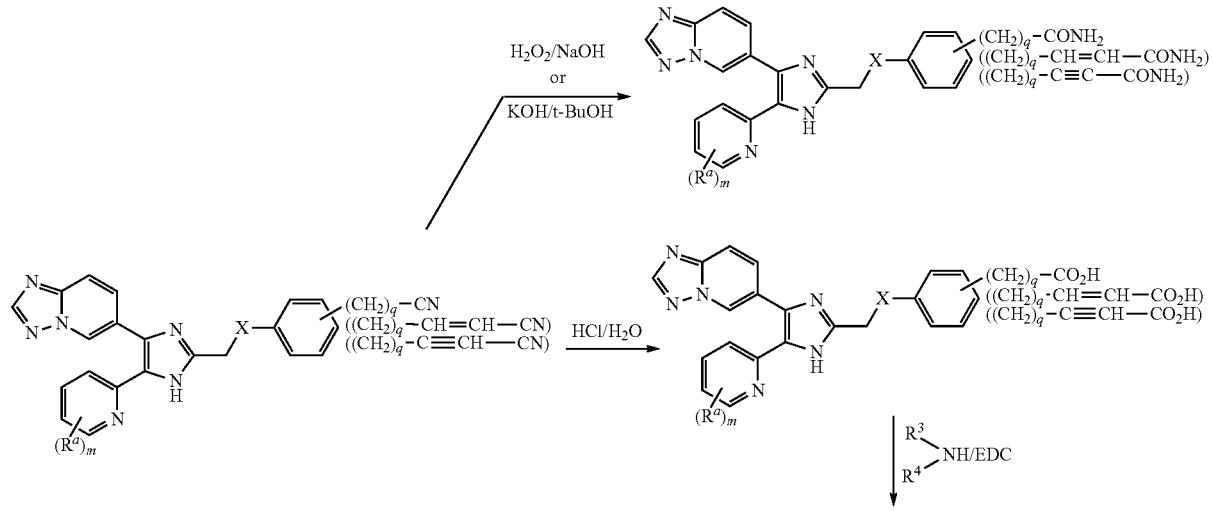

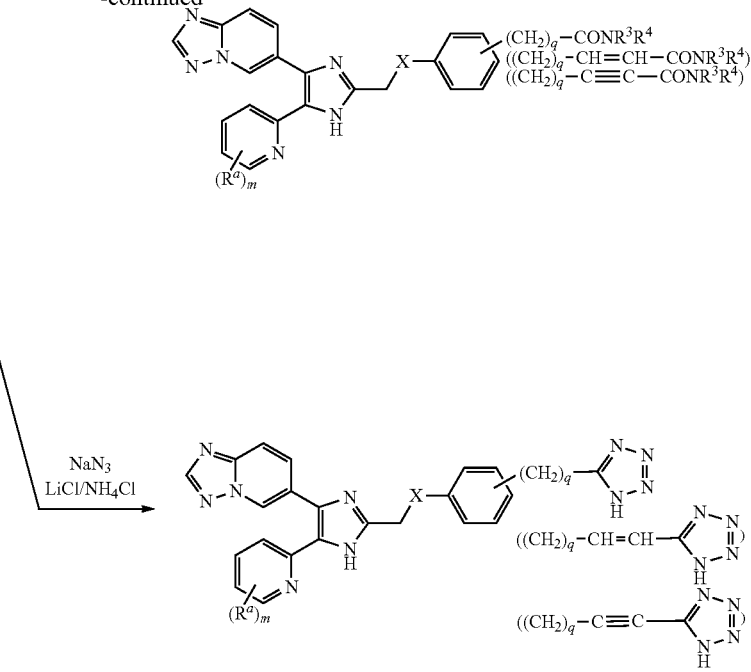

Alternatively, when $R^b$ compounds of formula (I) is $-(CH_2)_q-CN$, $-(CH_2)_q-CH=CH-CN$, or $-(CH_2)_q-C\equiv C-CN$, it can be further functionalized to form a compound of formula (I) as depicted in Scheme 3. $R^a$, $R^3$, $R^4$, X, m, and q have been defined as above.

The resulting compounds of this invention represented by the formula (I)-(IX) can be separated and purified by appropriate conventional methods such as column chromatography and recrystallization.

Compounds of the invention may be administered by any suitable route, for example by oral, buccal, sub-lingual, rectal, vaginal, nasal, topical or parenteral (including intravenous, intramuscular, subcutaneous and intracoronary) administration.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually, they will form up to about 80% of the formulation.

For administration to man in the curative or prophylactic treatment of the disorders identified above, oral, buccal or sub-lingual dosages of a compound of formula (I) will generally be in the range of from 50-5000 mg daily for an average adult patient (70 kg). Thus for a typical adult patient, individual tablets or capsules contain from 25-500 mg of active compound, in a suitable pharmaceutically acceptable vehicle or carrier, for administration in single or multiple doses, once or several times per day. Dosages for parenteral administration will typically be within the range of from 25-250 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, a compound of formula (I) can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavoring or coloring agents. Such liquid preparations may be prepared with pharmaceutically acceptable additives such as suspending agent (e.g. methylcellulose, a semi-synthetic glyceride such as witepsol or mixtures of glycerides such as a mixture of apricot kernel oil and PEG-6 esters or mixtures of PEG-8 and caprylic/capric glycerides). A compound may also be injected parenterally, for example intravenously, intramuscularly, subcutaneously or intracoronarily. For parenteral administration, the compound is best used in the form of a sterile aqueous solution which may contain other substances, for example, salts, or monosaccharides such as mannitol or glucose, to make the solution isotonic with blood.

Thus, the invention provides in a further aspect a pharmaceutical composition comprising a compound of formula (I), or a pharmaceutically acceptable salt or solvate thereof, together with a pharmaceutically acceptable diluent or carrier therefor.

The invention also provides a compound of formula (I), or a pharmaceutically acceptable salt or solvate thereof, or a pharmaceutical composition containing either entity, for use in therapy.

The invention further provides the use of a compound of formula (I), or a pharmaceutically acceptable salt or solvate thereof, or a pharmaceutical composition containing either entity, for the manufacture of a medicament for the treatment of a disease, mediated by the ALK5 and/or ALK4 receptors in mammals.

ALK5- and/or ALK4-mediated disease states include, but are not limited to, glomerulonephritis, diabetic nephropathy, lupus nephritis, hypertension-induced nephropathy, renal interstitial fibrosis, renal fibrosis resulting from complications of drug exposure, HIV-associated nephropathy, transplant nephropathy, liver fibrosis due to all etiologies, hepatic dysfunction attributable to infections, alcohol-induced hepatitis, disorders of the biliary tree, pulmonary fibrosis, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, hypertension-induced vascular remodeling, pulmonary arterial hypertension, coronary restenosis, peripheral restenosis, carotid restenosis, stent-induced restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub-dermal adhesion, scleroderma, fibrosclerosis, progressive systemic sclerosis, dermatomyositis, polymyositis, arthritis, osteoporosis, ulcers, impaired neurological function, male erectile dysfunction, Peyronie's disease, Dupuytren's contracture, Alzheimer's disease, Raynaud's syndrome, fibrotic cancers, tumor metastasis growth, radiation-induced fibrosis, and thrombosis.

The invention further provides a method of inhibiting the TGF-β and/or activin signaling pathways in human, for example, inhibiting the phosphorylation of Smad2 or Smad3 by ALK5 and/or ALK4.

The invention further provides a method of reducing the accumulation of excess extracellular matrix in human by inhibiting the TGF-β and/or activin signaling pathways, for example, inhibiting the phosphorylation of Smad2 or Smad3 by ALK5 and/or ALK4.

The invention further provides a method of inhibiting metastasis of tumor cells in human by inhibiting the TGF-β signaling pathway.

The invention further provides a method of treating carcinomas mediated by an overexpression of TGF-β in human by inhibiting the TGF-β signaling pathway.

The present invention is further illustrated in the following Examples, which should not be taken to limit the scope of the invention described in the claims. In the Examples, electrospray ionization mass spectra (ESI-MS) were obtained on a Q-Tof2 mass spectrometer (Micromass, Manchester, UK).

EXAMPLES

Preparative Example 1

Preparation of diphenyl (6-methylpyridin-2-yl)(phenylamino)methylphosphonate (a compound of the formula (III) wherein $R^a$=$CH_3$)

A mixture of 6-methylpyridine-2-carboxaldehyde (2.12 g, 17.50 mmol), aniline (1.63 g, 17.50 mmol), diphenyl phosphite (4.92 g, 21.00 mmol), and zirconyl chloride octahydrate (0.56 g, 1.75 mmol) was stirred at room temperature 1 h. The reaction mixture was extracted with $CH_2Cl_2$ (3×50 mL), and the $CH_2Cl_2$ solution was washed with water (2×20 mL), dried over anhydrous $Na_2SO_4$, filtered, and evaporated to dryness under reduced pressure. The residue was purified by MPLC on silica gel using a mixture of EtOAc and hexane as eluent to give the titled compound (6.96 g, 92%) as a white solid. $^1$H NMR (400 MHz, $CDCl_3$): δ 7.51 (t, 1H, J=7.8 Hz), 7.38 (dd, 1H, J=7.6, 2.0 Hz), 7.27-7.22 (m, 4H), 7.19-7.15 (m, 2H), 7.14-7.07 (m, 4H), 7.05-7.02 (m, 3H), 6.80-6.74 (m, 3H), 5.53 (pseudo t, 1H, J=7.4 Hz), 5.36 (dd, 1H, J=21.0, 8.2 Hz), 2.54 (s, 3H).

Preparative Example 2

Preparation of diphenyl (6-ethylpyridin-2-yl)(phenylamino)methylphosphonate (a compound of the formula (III) wherein $R^a$=$CH_2CH_3$)

The titled compound was prepared as described in Preparative Example 1 by using 6-ethylpyridine-2-carboxaldehyde in place of 6-methylpyridine-2-carboxaldehyde. Yield: 81%; $^1$H NMR (400 MHz, $CDCl_3$): δ 7.55 (t, 1H, J=7.6 Hz), 7.38 (dd, 1H, J=7.6, 2.0 Hz), 7.26-7.09 (m, 8H), 7.07-7.00 (m, 5H), 5.59 (pseudo t, 1H, J=7.0 Hz), 5.34 (dd, 1H, J=20.8, 8.0 Hz), 2.82 (q, 2H, J=7.6 Hz), 1.28 (t, 3H, J=7.6 Hz).

Preparative Example 3

Preparation of 2-([1,2,4]triazolo[1,5-a]pyridin-6-yl)-1-(6-methylpyridin-2-yl)ethanone (a compound of the formula (IV) wherein $R^a$=$CH_3$)

To a stirred solution of [1,2,4]triazolo[1,5-a]pyridine-6-carbaldehyde (2.50 g, 17.01 mmol) (prepared according to the method described in WO 03/087304 A2) and diphenyl (6-methylpyridin-2-yl)(phenylamino)methylphosphonate (7.32 g, 17.01 mmol) in a mixture of THF (40 mL) and i-PrOH (10 mL) was added $Cs_2CO_3$ (7.20 g, 22.11 mmol), and the mixture was stirred at room temperature overnight. A solution of 3 N HCl (25 mL) was added dropwise to the reaction mixture, and the mixture was stirred for 1 h. It was then diluted with tert-butyl methyl ether (40 mL) and extracted with 1 N HCl (2×35 mL). The aqueous extracts were neutralized with 50% KOH until pH 7-8 was reached. The precipitates were collected by filtration, washed with water, and dried over $P_2O_5$ in vacuo to give the titled compound (3.41 g, 80%) as an off-white solid. $^1$H NMR (400 MHz, $CDCl_3$): δ 8.61 (d, 1H, J=0.8 Hz), 8.31 (s, 1H), 7.88 (dd, 1H, J=7.6, 1.6 Hz), 7.73 (t, 1H, overlapped, J=7.6 Hz), 7.71 (dd, 1H, overlapped, J=9.2, 0.8 Hz), 7.54 (dd, 1H, J=9.2, 1.6 Hz), 7.37 (dd, 1H, J=7.6, 1.6 Hz), 4.62 (s, 2H), 2.67 (s, 3H).

Preparative Example 4

Preparation of 2-([1,2,4]triazolo[1,5-a]pyridin-6-yl)-1-(6-ethylpyridin-2-yl)ethanone (a compound of the formula (IV) wherein $R^a$=$CH_2CH_3$)

The titled compound was prepared as described in Preparative Example 3 by using diphenyl (6-ethylpyridin-2-yl)(phenylamino)methylphosphonate in place of diphenyl (6-methylpyridin-2-yl)(phenylamino)methylphosphonate. Yield: 78%; $^1$H NMR (400 MHz, $CDCl_3$): δ 8.61 (dd, 1H, J=1.6, 0.8 Hz), 8.29 (s, 1H), 7.88 (br d, 1H, J=7.6 Hz), 7.74 (t, 1H, J=7.6 Hz), 7.70 (dd, 1 H, J=9.2, 0.8 Hz), 7.54 (dd, 1H, J=9.2, 1.6 Hz), 7.37 (dd, 1H, J=7.6, 0.8 Hz), 4.62 (s, 2H), 2.93 (q, 2H, J=7.6 Hz), 1.39 (t, 3H, J=7.6 Hz).

Preparative Example 5

Preparation of 1-([1,2,4]triazolo[1,5-a]pyridin-6-yl)-2-(6-methylpyridin-2-yl)ethane-1,2-dione (a compound of the formula (V) wherein $R^a$=CH$_3$)

To a stirred suspension of 2-([1,2,4]triazolo[1,5-a]pyridin-6-yl)-1-(6-methylpyridin-2-yl)ethanone (6.20 g, 24.57 mmol) in DMSO (48 mL) was added dropwise HBr (48 wt. % in water, 5.96 g, 12.4 mL) at 0° C., and the mixture was heated at 60-70° C. After 2 h, the reaction mixture was cooled to 0° C., poured onto ice water (20 mL), and basified to pH 10 with solid K$_2$CO$_3$. The mixture was extracted with CHCl$_3$ (2×250 mL), and the organic phase was washed with water (2×100 mL), dried over anhydrous Na$_2$SO$_4$, filtered, and evaporated to dryness under reduced pressure. The residue was purified by MPLC on silica gel using a mixture of MeOH and CH$_2$Cl$_2$ as eluent to give the titled compound (6.02 g, 92%) as a light yellow solid. $^1$H NMR (400 MHz, CDCl$_3$): δ 9.11 (dd, 1H, J=1.6, 1.2 Hz), 8.47 (s, 1H), 8.14 (dd, 1H, J=9.2, 1.6 Hz), 8.04 (br d, 1H, J=7.6 Hz), 7.88 (dd, 1H, J=9.2, 1.2 Hz), 7.84 (t, 1H, J=7.8 Hz), 7.42 (br d, 1H, J=8.0 Hz), 2.49 (s, 3H).

Preparative Example 6

Preparation of 1-([1,2,4]triazolo[1,5-a]pyridin-6-yl)-2-(6-ethylpyridin-2-yl)ethane-1,2-dione (a compound the of formula (V) wherein $R^a$=CH$_2$CH$_3$)

The titled compound was prepared as described in Preparative Example 5 by using 2-([1,2,4]triazolo[1,5-a]pyridin-6-yl)-1-(6-ethylpyridin-2-yl)ethanone in place of 2-([1,2,4]triazolo[1,5-a]pyridin-6-yl)-1-(6-methylpyridin-2-yl)ethanone. Yield: 79%; $^1$H NMR (400 MHz, CDCl$_3$): δ 9.11 (dd, 1H, J=1.6, 0.8 Hz), 8.42 (s, 1H), 8.08 (dd, 1H, J=9.2, 1.6 Hz), 7.98 (br d, 1H, J=7.6 Hz), 7.83 (dd, 1H, overlapped, J=9.2, 0.8 Hz), 7.82 (t, 1H, overlapped, J=7.6 Hz), 7.38 (br d, 1H, J=7.6 Hz), 2.71 (q, 2H, J=7.6 Hz), 1.08 (t, 3H, J=7.6 Hz).

Preparative Example 7

Preparation of 6-(2-(dimethoxymethyl)-5-(6-methylpyridin-2-yl)-1H-imidazol-4-yl)-[1,2,4]triazolo[1,5-a]pyridine (a compound of the formula (VI) wherein $R^a$=CH$_3$)

A stirred solution of 1-([1,2,4]triazolo[1,5-a]pyridin-6-yl)-2-(6-methylpyridin-2-yl)ethane-1,2-dione (6.00 g, 22.49 mmol) in tert-butyl methyl ether (120 mL) was treated with glyoxal dimethyl acetal (60 wt. % solution in water, 7.8 mL, 44.98 mmol). NH$_4$OAc (4.33 g, 56.2 mmol) in MeOH (60 mL) was added to it, and the resulting mixture was stirred at room temperature for 3 h. The pH of the reaction was adjusted to 8 with saturated aqueous NaHCO$_3$ solution. The reaction mixture was extracted with CHCl$_3$ (2×150 mL), and the CHCl$_3$ solution was washed with water (100 mL), dried over anhydrous Na$_2$SO$_4$, filtered, and evaporated to dryness under reduced pressure. The residue was purified by MPLC on silica gel using a mixture of MeOH and CH$_2$Cl$_2$ as eluent to give the titled compound (6.13 g, 78%) as a light yellow foam. $^1$H NMR (400 MHz, CDCl$_3$): δ 10.54 (br s, 1H), 8.96 (s, 1H), 8.36 (s, 1H), 7.82 (dd, 1H, J=9.2, 1.6 Hz), 7.77 (dd, 1H, J=9.2, 0.8 Hz), 7.47 (t, 1H, J=7.8 Hz), 7.23 (d, 1H, J=7.6 Hz), 7.04 (d, 1 H, J=8.0 Hz), 5.57 (s, 1H), 3.48 (s, 6H), 2.58 (s, 3H).

Preparative Example 8

Preparation of 6-(2-(dimethoxymethyl)-5-(6-ethylpyridin-2-yl)-1H-imidazol-4-yl)-[1,2,4]triazolo[1,5-a]pyridine (a compound of the formula (VI) wherein $R^a$=CH$_2$CH$_3$)

The titled compound was prepared as described in Preparative Example 7 by using 1-([1,2,4]triazolo[1,5-a]pyridin-6-yl)-2-(6-ethylpyridin-2-yl)ethane-1,2-dione in place of 1-([1,2,4]triazolo[1,5-a]pyridin-6-yl)-2-(6-methylpyridin-2-yl)ethane-1,2-dione. Yield: 68%; $^1$H NMR (400 MHz, CDCl$_3$): δ 10.67 (br s, 1H), 8.97 (br s, 1H), 8.35 (s, 1H), 7.83 (dd, 1H, J=9.2, 1.6 Hz), 7.76 (dd, 1H, J=9.2, 0.8 Hz), 7.50 (t, 1H, J=7.8 Hz), 7.25 (br d, 1H, J=7.6 Hz), 7.05 (d, 1H, J=8.0 Hz), 5.56 (s, 1H), 3.46 (s, 6H), 2.83 (q, 2H, J=7.6 Hz), 1.31 (t, 3H, J=7.6 Hz).

Preparative Example 9

Preparation of 4-([1,2,4]triazolo[1,5-a]pyridin-6-yl)-5-(6-methylpyridin-2-yl)-1H-imidazole-2-carbaldehyde (a compound of the formula (VII) wherein $R^a$=CH$_3$)

6-(2-(Dimethoxymethyl)-5-(6-methylpyridin-2-yl)-1H-imidazol-4-yl)-[1,2,4]triazolo[1,5-a]pyridine (6.00 g, 17.12 mmol) was dissolved in 1 N HCl (120 mL), and the mixture was heated at 70° C. for 3 h. The reaction mixture was allowed to cool to 0° C., and then it was neutralized with saturated aqueous NaHCO$_3$ solution. The mixture was extracted with 10% MeOH in CHCl$_3$ (3×200 mL), and the organic phase was dried over anhydrous Na$_2$SO$_4$, filtered, and evaporated to dryness under reduced pressure to give the titled compound (4.69 g, 90%) as a light yellow solid. $^1$H NMR (400 MHz, CDCl$_3$): δ 9.82 (s, 1H), 9.01 (br s, 1H), 8.41 (s, 1H), 7.85 (dd, 1H, J=9.2, 0.8 Hz), 7.82 (dd, 1H, J=9.2, 1.6 Hz), 7.55 (t, 1H, J=7.8 Hz), 7.33 (br s, 1H), 7.16 (d, 1H, J=8.0 Hz), 2.60 (s, 3H).

Preparative Example 10

Preparation of 4-([1,2,4]triazolo[1,5-a]pyridin-6-yl)-5-(6-ethylpyridin-2-yl)-1H-imidazole-2-carbaldehyde (a compound of the formula (VII) wherein $R^a$=CH$_2$CH$_3$)

The titled compound was prepared as described in Preparative Example 9 by using 6-(2-(dimethoxymethyl)-5-(6-ethylpyridin-2-yl)-1H-imidazol-4-yl)-[1,2,4]triazolo[1,5-a]pyridine in place of 6-(2-(dimethoxymethyl)-5-(6-methylpyridin-2-yl)-1H-imidazol-4-yl)-[1,2,4]triazolo[1,5-a]pyridine. Yield: 99%; $^1$H NMR (400 MHz, DMSO-d$_6$) δ 9.86 (t, 1H, J=1.2 Hz), 9.59 (s, 1H), 8.43 (s, 1H), 8.21 (dd, 1H, J=9.2, 1.6 Hz), 7.82 (br d, 1H, J=8.0 Hz), 7.73 (dd, 1H, J=9.2, 0.8 Hz), 7.69 (t, 1H, J=7.8 Hz), 7.08 (br d, 1H, J=7.6 Hz), 2.71 (q, 2H, J=7.6 Hz), 1.16 (t, 3H, J=7.6 Hz).

Preparative Example 11

Preparation of 3-amino-5-(dimethylamino)benzonitrile (a compound of the formula (VIII) wherein $R^b$=3-cyano-5-dimethylamino). This compound was prepared by the following 2 steps.

3-Bromo-N,N-dimethyl-5-nitroaniline (1.73 g, 7.06 mmol) (prepared according to the method described in *J. Org. Chem.* 60: 5091-5103 (2003)), pyridine (24 mL), and CuCN (1.26 g, 2.14 mmol) were added to a dry sealed tube. The mixture was heated at 220° C. with stirring for 3.5 h. The reaction mixture was allowed to cool to 100° C., poured into a flask containing a mixture of aqueous ammonia (100 mL) and water (100 mL), and extracted with EtOAc (2×100 mL). The EtOAc solution was washed with diluted ammonia solution (100 mL), water (100 mL) and brine (100 mL) successively, dried over anhydrous $Na_2SO_4$, filtered, and evaporated to dryness under reduced pressure. The residue was purified by MPLC on silica gel using a mixture of EtOAc and hexane as eluent to give 3-(dimethylamino)-5-nitrobenzonitrile (0.44 g, 33%) as an orange solid. $^1$H NMR (400 MHz, $CDCl_3$): δ 7.74 (dd, 1H, J=2.0, 1.2 Hz), 7.65 (t, 1H, J=2.2 Hz), 7.11 (dd, 1H, J=2.4, 1.2 Hz), 3.10 (s, 6H).

The above nitro compound, 3-(dimethylamino)-5-nitrobenzonitrile (0.42 g, 2.22 mmol) in methanol (80 mL) was hydrogenated in the presence of 10% Pd/C (0.04 g) under a hydrogen gas atmosphere overnight. The reaction mixture was filtered through a Celite pad, and the filtrate was evaporated to dryness under reduced pressure. The residue was purified by MPLC on silica gel using a mixture of EtOAc and hexane as eluent to give the titled compound (0.29 g, 80%) as a brown viscous liquid. $^1$H NMR (400 MHz, $CDCl_3$): δ 6.35 (dd, 1H, J=2.4, 1.6 Hz), 6.28 (dd, 1H, J=2.0, 1.6 Hz), 6.14 (t, 1H, J=2.2 Hz), 3.76 (br s, 2H), 2.92 (s, 6H).

Preparative Example 12

Preparation of 3-((dimethylamino)methyl)-2-fluoroaniline (a compound of the formula (VIII) wherein $R^b$=3-(dimethylamino)methyl-2-fluoro). This compound was prepared by the following 3 steps started with commercially available 2-fluoro-1-methyl-3-nitrobenzene.

A stirred solution of 2-fluoro-1-methyl-3-nitrobenzene (15.80 g, 101.94 mmol) and N-bromosuccinimide (18.14 g, 101.94 mmol) in $CCl_4$ (400 mL) was treated with benzoyl peroxide (0.37 g, 1.52 mmol). The mixture was heated at reflux temperature overnight and then cooled to room temperature. The reaction mixture was filtered, and the filtrate was evaporated to dryness under reduced pressure. The residue was dissolved in $CH_2Cl_2$ (100 mL) and filtered again. The filtrate was evaporated to dryness under reduced pressure, and the residue was purified by MPLC on silica gel using a mixture of EtOAc and hexane as eluent to give 1-(bromomethyl)-2-fluoro-3-nitrobenzene (8.11 g, 34%) as an off-white solid. $^1$H NMR (400 MHz, $CDCl_3$): δ 8.02 (m, 1H), 7.71 (m, 1H), 7.30 (td, 1H, J=8.4, 1.6 Hz), 4.55 (d, 2H, J=1.6 Hz).

To a stirred mixture of 1-(bromomethyl)-2-fluoro-3-nitrobenzene (0.70 g, 2.99 mmol) and dimethylamine hydrochloride (0.48 g, 5.98 mmol) in $CH_2Cl_2$ (10 mL) was added triethylamine (0.91 g, 8.97 mmol) dropwise. The mixture was stirred at room temperature for 3 h and evaporated to dryness under reduced pressure. The residue was diluted with water (10 mL) and extracted with EtOAc (2×25 mL). The EtOAc solution was washed with water (20 mL), dried over anhydrous $Na_2SO_4$, filtered, and evaporated to dryness under reduced pressure. The residue was purified by MPLC on silica gel using a mixture of EtOAc and hexane as eluent to give 1-(2-fluoro-3-nitrophenyl)-N,N-dimethylmethanamine (0.45 g, 76%) as a yellow viscous liquid. $^1$H NMR (400 MHz, $CD_3OD$): δ 8.04-7.99 (m, 1H), 7.78-7.73 (m, 1H), 7.37 (td, 1H, J=8.0, 1.0 Hz), 3.64 (d, 2H, J=2.0 Hz), 2.29 (d, 6H, J=0.8 Hz).

A mixture of the above nitro compound, 1-(2-fluoro-3-nitrophenyl)-N,N-dimethylmethanamine (0.45 g, 1.93 mmol), iron powder (1.35 g, 2.41 mmol), 2 N HCl (1 mL), and ethanol (5 mL) was heated at reflux temperature with stirring for 2 h. After cooling to room temperature, the mixture was filtered through a Celite pad. The filtrate was evaporated to dryness under reduced pressure, and the residue was diluted with water (10 mL) and basified with solid $K_2CO_3$ to pH 10. The aqueous mixture was extracted with EtOAc (2×25 mL), and the EtOAc solution was dried over anhydrous $Na_2SO_4$, filtered, and evaporated to dryness under reduced pressure. The residue was purified by MPLC on silica gel using a mixture of EtOAc and hexane as eluent to give the titled compound (0.35 g, 91%) as a white solid. $^1$H NMR (400 MHz, $CDCl_3$): δ 6.88 (td, 1H, J=7.8, 1.0 Hz), 6.72-6.67 (m, 2H), 3.71 (br s, 2H), 3.47 (d, 2H, J=1.6 Hz), 2.27 (s, 6H).

Preparative Example 13

Preparation of 2-fluoro-3-(pyrrolidin-1-ylmethyl) aniline (a compound of the formula (VIII) wherein $R^b$=2-fluoro-3-(pyrrolidin-1-ylmethyl))

To a stirred solution of 1-(bromomethyl)-2-fluoro-3-nitrobenzene (2.00 g, 8.54 mmol) and pyrrolidine (0.91 g, 12.82 mmol) in $CH_2Cl_2$ (15 mL) was added triethylamine (1.72 g, 17.08 mmol) dropwise at 0° C. The mixture was stirred at room temperature overnight and then evaporated to dryness under reduced pressure. The residue was diluted with water (15 mL) and extracted with EtOAc (2×30 mL). The EtOAc solution was washed with brine (20 mL), dried over anhydrous $Na_2SO_4$, filtered, and evaporated to dryness under reduced pressure. The residue was purified by MPLC on silica gel using a mixture of EtOAc and hexane as eluent to give 1-(2-fluoro-3-nitrobenzyl)pyrrolidine (1.20 g, 63%) as a viscous oil. $^1$H NMR (400 MHz, $CD_3OD$): δ 8.02-7.97 (m, 1H), 7.81-7.76 (m, 1H), 7.36 (td, 1H, J=8.0, 1.2 Hz), 3.81 (d, 1H, J=2.0 Hz), 2.62-2.58 (m, 4H), 1.84-1.80 (m, 4H).

The titled compound was prepared as described in Preparative Example 12 by using 1-(2-fluoro-3-nitrobenzyl)pyrrolidine in place of 1-(2-fluoro-3-nitrophenyl)-N,N-dimethylmethanamine. Yield: 80%; $^1$H NMR (400 MHz, $CD_3OD$): δ 6.87 (td, 1H, J=8.0, 0.8 Hz), 6.77 (td, 1H, J=8.0, 2.0 Hz), 6.68-6.64 (m, 1H), 3.67 (d, 2H, J=1.6 Hz), 2.60-2.57 (m, 4H), 1.82-1.78 (m, 4H).

Preparative Example 14

Preparation of 2-fluoro-3-(morpholinomethyl)aniline (a compound of the formula (VIII) wherein $R^b$=2-fluoro-3-(morpholinomethyl))

A stirred solution of 1-(bromomethyl)-2-fluoro-3-nitrobenzene (2.50 g, 10.6 mmol) and morpholine (2.78 g, 32.0 mmol) in toluene (24 mL) was heated at reflux temperature for 2.5 h. The reaction mixture was allowed to cool to room temperature and then washed with 1 N NaOH (2×20 mL). The aqueous layer was extracted with EtOAc (2×25 mL), and the combined toluene solution and EtOAc extracts were dried over anhydrous $Na_2SO_4$, filtered, and evaporated to dryness under reduced pressure. The residue was purified by MPLC on silica gel using a mixture of EtOAc and hexane as eluent to give 4-(2-fluoro-3-nitrobenzyl)morpholine (1.95 g, 89%) as a light yellow solid. $^1$H NMR (400 MHz, $CD_3OD$): δ 8.02-7.97 (m, 1H), 7.83-7.78 (m, 1H), 7.36 (td, 1H, J=8.0, 1.0 Hz), 3.70-3.67 (m, 6H), 2.51 (br t, 4H, J=4.6 Hz).

The titled compound was prepared as described in Preparative Example 12 by using (4-(2-fluoro-3-nitrobenzyl)morpholine) in place of 1-(2-fluoro-3-nitrophenyl)-N,N-dimethylmethanamine. Yield: 90%; $^1$H NMR (400 MHz, $CD_3OD$): δ 6.87 (td, 1H, J=8.0, 0.8 Hz), 6.77 (td, 1H, J=8.0, 2.0 Hz), 6.68-6.64 (m, 1H), 3.68 (br t, 4H, J=4.8 Hz), 3.55 (d, 2H, J=1.6 Hz), 2.49 (br t, 4H, J=4.8 Hz).

Preparative Example 15

Preparation of 3-amino-4-((dimethylamino)methyl) benzonitrile (a compound of the formula (VIII) wherein $R^b$=5-cyano-2-(dimethylamino)methyl)

To a stirred mixture of 4-(bromomethyl)-3-nitrobenzonitrile (5.00 g, 20.74 mmol) (prepared according to the method described in WO 07/024,945 A1) and dimethylamine hydrochloride (2.03 g, 24.89 mmol) in $CH_2Cl_2$ (70 mL) was added triethylamine (6.30 g, 62.23 mmol) dropwise at 0° C., and the mixture was stirred at room temperature overnight. The reaction mixture was evaporated to dryness under reduced pressure, and the residue was diluted with water (20 mL) and extracted with $CH_2Cl_2$ (3×100 mL). The $CH_2Cl_2$ solution was dried over anhydrous $Na_2SO_4$, filtered, and evaporated to dryness under reduced pressure. The residue was purified by MPLC on silica gel using a mixture of EtOAc and hexane as eluent to give 4-((dimethylamino)methyl)-3-nitrobenzene (3.58 g, 84%) as an orange solid. $^1$H NMR (400 MHz, $CDCl_3$): δ 8.15 (br s, 1H), 7.92 (br s, 1H), 7.85 (br d, 1H, J=7.2 Hz), 3.80 (s, 2H), 2.27 (s, 6 H).

The titled compound was prepared as described in Preparative Example 11 by using 4-((dimethylamino)methyl)-3-nitrobenzonitrile in place of 3-(dimethylamino)-5-nitrobenzonitrile. Yield: 91%; $^1$H NMR (400 MHz, $CDCl_3$): δ 7.02 (dd, 1H, J=7.6, 0.4 Hz), 6.91 (dd, 1H, J=7.6, 1.6 Hz), 6.84 (d, 1H, J=1.6 Hz), 5.05 (br s, 2H), 3.43 (s, 2H), 2.18 (s, 6H).

Preparative Example 16

Preparation of 3-amino-2-((dimethylamino)methyl) benzonitrile (a compound of the formula (VIII) wherein $R^b$=3-cyano-2-(dimethyamino)methyl)

To a stirred mixture of 2-(bromomethyl)-3-nitrobenzonitrile (1.10 g, 4.56 mmol) (prepared according to the method described in Tetrahedron 40: 1863-1868 (1984)) and dimethylamine hydrochloride (0.74 g, 9.13 mmol) in $CH_2Cl_2$ (15 mL) was added triethylamine (1.85 g, 18.25 mmol) dropwise at 0° C. The resulting mixture was stirred at room temperature for 2 h and evaporated to dryness under reduced pressure. The residue was diluted with water (10 mL) and extracted with EtOAc (3×50 mL). The EtOAc solution was dried over anhydrous $Na_2SO_4$, filtered, and evaporated to dryness under reduced pressure. The residue was purified by MPLC on silica gel using a mixture of EtOAc and hexane as eluent to give 2-((dimethylamino)methyl)-3-nitrobenzonitrile (0.75 g, 80%) as a yellow oil. $^1$H NMR (400 MHz, $CDCl_3$): δ 7.93 (br d, 1H, J=8.0 Hz), 7.85 (dd, 1H, J=8.0, 1.4 Hz), 7.55 (t, 1H, J=8.0 Hz), 3.94 (s, 2H), 2.24 (s, 6H).

The titled compound was prepared as described in Preparative Example 11 by using 2-((dimethylamino)methyl)-3-nitrobenzonitrile in place of 3-(dimethylamino)-5-nitrobenzonitrile. Yield: 93%; $^1$H NMR (400 MHz, $CDCl_3$): δ 7.15 (t, 1H, J=7.6 Hz), 7.00 (dd, 1H, J=7.6, 0.8 Hz), 6.83 (d, 1H, J=7.6 Hz), 5.06 (br s, 2H), 3.73 (s, 2H), 2.29 (s, 6H).

Preparative Example 17

Preparation of 3-amino-5-((dimethylamino)methyl) benzonitrile (a compound of the formula (VIII) wherein $R^b$=3-cyano-5-(dimethylamino)methyl)

To a stirred mixture of 3-(bromomethyl)-5-nitrobenzonitrile (1.50 g, 6.22 mmol) (prepared according to the method described in J. Org. Chem. 55: 1040-1043 (1990)) and dimethylamine hydrochloride (1.01 g, 12.44 mmol) in $CH_2Cl_2$ (15 mL) was added triethylamine (1.88 g, 18.66 mmol) dropwise at 0° C. The resulting mixture was stirred at room temperature for 3 h and evaporated to dryness under reduced pressure. The residue was diluted with water (15 mL) and extracted with EtOAc (3×50 mL). The EtOAc solution was dried over anhydrous $Na_2SO_4$, filtered, and evaporated to dryness under reduced pressure. The residue was purified by MPLC on silica gel using a mixture of EtOAc and hexane as eluent to give 3-((dimethylamino)methyl)-5-nitrobenzonitrile (1.10 g, 87%) as a viscous liquid. $^1$H NMR (400 MHz, $CDCl_3$): δ 8.45 (s, 1 H), 8.40 (d, 1H, J=1.6 Hz), 8.01 (s, 1H), 3.59 (s, 2H), 2.30 (s, 6H).

The titled compound was prepared as described in Preparative Example 11 by using 3-((dimethylamino)methyl)-5-nitrobenzonitrile in place of 3-(dimethylamino)-5-nitrobenzonitrile. Yield: 98%; $^1$H NMR (400 MHz, $CDCl_3$): δ 6.96 (m, 1H), 6.88 (br d, 1H, J=0.8 Hz), 6.80 (dd, 1H, J=2.4, 1.6 Hz), 3.86 (br s, 2H), 3.34 (s, 2H), 2.24 (s, 6H).

Preparative Example 18

Preparation of 3-amino-4-(pyrrolidin-1-ylmethyl) benzonitrile (a compound of the formula (VIII) wherein $R^b$=5-cyano-2-(pyrrolidin-1-ylmethyl))

To a stirred solution of 4-(bromomethyl)-3-nitrobenzonitrile (5.12 g, 21.57 mmol) and pyrrolidine (1.84 g, 25.88 mmol) in $CH_2Cl_2$ (72 mL) was added triethylamine (6.54 g, 64.71 mmol) dropwise at 0° C. The mixture was stirred at room temperature for 1.5 h and evaporated to dryness under reduced pressure. The residue was diluted with water (30 mL) and extracted with $CH_2Cl_2$ (3×100 mL). The $CH_2Cl_2$ solution was dried over anhydrous $Na_2SO_4$, filtered, and evaporated to dryness under reduced pressure. The residue was purified by MPLC on silica gel using a mixture of EtOAc and hexane as eluent to give 3-nitro-4-(pyrrolidin-1-ylmethyl)benzonitrile (2.24 g, 45%) as a yellow solid. $^1$H NMR (400 MHz, $CDCl_3$): δ 8.16 (d, 1 H, J=1.6 Hz), 7.94 (br d, 1H, J=8.0 Hz), 7.83 (dd, 1H, J=8.0, 1.6 Hz), 3.99 (s, 2H), 2.54 (br s, 4H), 1.79 (m, 4H).

The titled compound was prepared as described in Preparative Example 11 by using 3-nitro-4-(pyrrolidin-1-ylmethyl)benzonitrile in place of 3-(dimethylamino)-5-nitrobenzonitrile. Yield: 91%; $^1$H NMR (400 MHz, $CDCl_3$): δ 7.06 (d, 1H, J=7.6 Hz), 6.91 (dd, 1H, J=7.6, 1.6 Hz), 6.84 (d, 1H, J=1.6 Hz), 5.08 (br s, 2H), 3.64 (s, 2H), 2.47 (br s, 4H), 1.78 (br s, 4H).

Preparative Example 19

Preparation of 3-amino-2-(pyrrolidin-1-ylmethyl) benzonitrile (a compound of the formula (VIII) wherein $R^b$=3-cyano-2-(pyrrolidin-1-ylmethyl))

To a stirred solution of 2-(bromomethyl)-3-nitrobenzonitrile (1.10 g, 4.56 mmol) and pyrrolidine (0.65 g, 9.13 mmol) in $CH_2Cl_2$ (15 mL) was added triethylamine (1.85 g, 18.25 mmol) dropwise at 0° C. The mixture was stirred at room temperature for 2 h and evaporated to dryness under reduced pressure. The residue was diluted with water (10 mL) and extracted with $CH_2Cl_2$ (3×50 mL). The $CH_2Cl_2$ solution was dried over anhydrous $Na_2SO_4$, filtered, and evaporated to dryness under reduced pressure. The residue was purified by MPLC on silica gel using a mixture of EtOAc and hexane as eluent to give 3-nitro-2-(pyrrolidin-1-ylmethyl)benzonitrile (0.96 g, 91%) as a yellow solid. $^1$H NMR (400 MHz, $CDCl_3$):

δ 7.90 (d, 1 H, J=7.6 Hz), 7.83 (dd, 1H, J=7.6, 0.8 Hz), 7.52 (t, 1H, J=7.6 Hz), 4.14 (s, 2H), 2.52 (br s, 4H), 1.72 (br s, 4H).

The titled compound was prepared as described in Preparative Example 11 by using 3-nitro-2-(pyrrolidin-1-ylmethyl)benzonitrile in place of 3-(dimethylamino)-5-nitrobenzonitrile. Yield: 93%; $^1$H NMR (400 MHz, CDCl$_3$): δ 7.13 (t, 1H, J=7.8 Hz), 6.99 (dd, 1H, J=7.8, 1.2 Hz), 6.82 (d, 1H, J=8.0 Hz), 5.11 (br s, 2H), 3.91 (s, 2H), 2.58 (br s, 4H), 1.81 (br s, 4H).

Preparative Example 20

Preparation of 3-amino-5-(pyrrolidin-1-ylmethyl)benzonitrile (a compound of the formula (VIII) wherein $R^b$=3-cyano-5-(pyrrolidin-1-ylmethyl))

To a stirred solution of 3-(bromomethyl)-5-nitrobenzonitrile (1.50 g, 6.22 mmol) and pyrrolidine (0.53 g, 7.46 mmol) in CH$_2$Cl$_2$ (15 mL) was added triethylamine (1.88 g, 18.68 mmol) dropwise at 0° C., and the mixture was stirred at room temperature overnight. The reaction mixture was evaporated to dryness under reduced pressure, and the residue was diluted with water (15 mL) and extracted with EtOAc (3×50 mL). The EtOAc solution was dried over anhydrous Na$_2$SO$_4$, filtered, and evaporated to dryness under reduced pressure. The residue was purified by MPLC on silica gel using a mixture of EtOAc and hexane as eluent to give 3-nitro-5-(pyrrolidin-1-ylmethyl)benzonitrile (1.30 g, 90%) as a yellow solid. $^1$H NMR (400 MHz, CDCl$_3$): δ 8.45 (br s, 1H), 8.39 (br t, 1H, J=1.6 Hz), 8.02 (br s, 1H), 3.78 (s, 2H), 2.56 (br s, 4H), 1.84 (br s, 4H).

The titled compound was prepared as described in Preparative Example 11 by using 3-nitro-5-(pyrrolidin-1-ylmethyl)benzonitrile in place of 3-(dimethylamino)-5-nitrobenzonitrile. Yield: 85%; $^1$H NMR (400 MHz, CDCl$_3$): δ 6.99 (pseudo t, 1H, J=1.6 Hz), 6.94 (pseudo t, 1H, J=1.6 Hz), 6.79 (dd, 1H, J=2.4, 1.6 Hz), 3.87 (br s, 2H), 3.56 (s, 2H), 2.54 (m, 4H), 1.81 (m, 4 H).

Preparative Example 21

Preparation of 3-amino-4-(morpholinomethyl)benzonitrile (a compound of the formula (VIII) wherein $R^b$=5-cyano-2-(morpholinomethyl))

To a stirred solution of 4-(bromomethyl)-3-nitrobenzonitrile (7.12 g, 29.55 mmol) and morpholine (3.09 g, 35.45 mmol) in CH$_2$Cl$_2$ (98 mL) was added triethylamine (8.97 g, 88.64 mmol) dropwise at 0° C. The mixture was stirred at room temperature for 1.5 h and evaporated to dryness under reduced pressure. The residue was diluted with water (40 mL) and extracted with CH$_2$Cl$_2$ (3×100 mL). The CH$_2$Cl$_2$ solution was washed with water (50 mL), dried over anhydrous Na$_2$SO$_4$, filtered and evaporated to dryness under reduced pressure. The residue was purified by MPLC on silica gel using a mixture of EtOAc and hexane as eluent to give 4-(morpholinomethyl)-3-nitrobenzonitrile (5.84 g, 80%) as a yellow solid. $^1$H NMR (400 MHz, CDCl$_3$): δ 8.12 (s, 1H), 7.83 (br s, 2H), 3.84 (s, 2H), 3.67 (t, 4H, J=4.6 Hz), 2.45 (t, 4H, J=4.6 Hz).

The titled compound was prepared as described in Preparative Example 11 by using 4-(morpholinomethyl)-3-nitrobenzonitrile in place of 3-(dimethylamino)-5-nitrobenzonitrile. Yield: 78%; $^1$H NMR (400 MHz, CDCl$_3$): δ 7.05 (d, 1H, J=8.0 Hz), 6.92 (dd, 1H, J=8.0, 1.6 Hz), 6.86 (d, 1H, J=1.6 Hz), 5.02 (br s, 2H), 3.68 (br t, 4H, J=4.0 Hz), 3.53 (s, 2H), 2.41 (br s, 4H).

Preparative Example 22

Preparation of 3-amino-2-(morpholinomethyl)benzonitrile (a compound of the formula (VIII) wherein $R^b$=3-Cyano-2-(morpholinomethyl))

To a stirred solution of 2-(bromomethyl)-3-nitrobenzonitrile (1.10 g, 4.56 mmol) and morpholine (0.80 g, 9.13 mmol) in CH$_2$Cl$_2$ (15 mL) was added triethylamine (1.85 g, 18.25 mmol) dropwise at 0° C. The mixture was stirred at room temperature for 1.5 h and evaporated to dryness under reduced pressure. The residue was diluted with water (10 mL) and extracted with CH$_2$Cl$_2$ (3×50 mL). The CH$_2$Cl$_2$ solution was dried over anhydrous Na$_2$SO$_4$, filtered, and evaporated to dryness under reduced pressure. The residue was purified by MPLC on silica gel using a mixture of EtOAc and hexane as eluent to give 2-(morpholinomethyl)-3-nitrobenzonitrile (1.02 g, 90%) as a yellow solid. $^1$H NMR (400 MHz, CDCl$_3$): δ 7.90 (br d, 1H, J=8.0 Hz), 7.84 (dd, 1H, J=8.0, 1.2 Hz), 7.56 (t, 1H, J=8.0 Hz), 3.99 (s, 2H), 3.60 (br t, 4H, J=4.4 Hz), 2.46 (br s, 4H).

The titled compound was prepared as described in Preparative Example 11 by using 2-(morpholinomethyl)-3-nitrobenzonitrile in place of 3-(dimethylamino)-5-nitrobenzonitrile. Yield: 82%; $^1$H NMR (400 MHz, CDCl$_3$): δ 7.15 (t, 1H, J=7.6 Hz), 7.01 (d, 1H, J=7.6 Hz), 6.83 (d, 1H, J=7.6 Hz), 5.00 (br s, 2H), 3.78 (s, 2H), 3.69 (br s, 4H), 2.50 (br s, 4H).

Preparative Example 23

Preparation of 3-amino-5-(morpholinomethyl)benzonitrile (a compound of the formula (VIII) wherein $R^b$=3-cyano-5-(morpholinomethyl))

To a stirred solution of 3-(bromomethyl)-5-nitrobenzonitrile (1.50 g, 6.22 mmol) and morpholine (0.65 g, 7.46 mmol) in CH$_2$Cl$_2$ (15 mL) was added triethylamine (1.88 g, 18.66 mmol) dropwise at 0° C. The mixture was stirred at room temperature overnight and then evaporated to dryness under reduced pressure. The residue was diluted with water (15 mL) and extracted with EtOAc (3×50 mL). The EtOAc solution was dried over anhydrous Na$_2$SO$_4$, filtered and evaporated to dryness under reduced pressure. The residue was purified by MPLC on silica gel using a mixture of EtOAc and hexane as eluent to give 3-(morpholinomethyl)-5-nitrobenzonitrile (0.87 g, 85%) as an off-white solid. $^1$H NMR (400 MHz, CDCl$_3$): δ 8.45 (br s, 1 H), 8.41 (br s, 1H), 8.01 (br s, 1H), 3.74 (br t, 4H, J=4.4 Hz), 3.64 (s, 2H), 2.48 (br t, 4H, J=4.4 Hz).

The titled compound was prepared as described in Preparative Example 11 by using 3-(morpholinomethyl)-5-nitrobenzonitrile in place of 3-(dimethylamino)-5-nitrobenzonitrile. Yield: 85%; $^1$H NMR (400 MHz, CDCl$_3$): δ 7.00 (br t, 1H, J=1.6 Hz), 6.93 (br s, 1H), 6.81 (dd, 1H, J=2.4, 1.6 Hz), 3.88 (br s, 2H), 3.74 (br t, 4H, J=4.6 Hz), 3.44 (s, 2H), 2.47 (br s, 4H).

Preparative Example 24

Preparation of 2-(2-fluorophenoxy)acetaldehyde (a compound of the formula (IX) wherein $R^b$=2-fluoro, X=O). This compound was prepared by the following 2 steps.

A stirred mixture of 2-fluorophenol (1.00 g, 8.92 mmol), 2-bromo-1,1-diethoxyethane (1.75 g, 8.92 mmol), and K$_2$CO$_3$ (1.47 g, 10.7 mmol) in anhydrous DMF (10 mL) was heated at 110° C. overnight. The reaction mixture was poured into ice cold water (15 mL) and extracted with EtOAc (2×100 mL). The EtOAc solution was washed with water (25 mL) and brine (25 mL), dried over anhydrous $Na_2SO_4$, filtered, and evaporated to dryness under reduced pressure. The residue was purified by MPLC on silica gel using a mixture of EtOAc and hexane as eluent to give 1-(2,2-diethoxyethoxy)-2-fluorobenzene (1.65 g, 81%) as a viscous liquid. $^1$H NMR (400 MHz, $CDCl_3$): δ 7.09-6.96 (m, 3H), 6.93-6.87 (m, 1H), 4.85 (t, 1H, J=5.2 Hz), 4.07 (d, 2H, J=5.2 Hz), 3.82-3.74 (m, 2H), 3.69-3.61 (m, 2H), 1.24 (t, 6H, J=7.0 Hz).

To a stirred solution of 1-(2,2-diethoxyethoxy)-2-fluorobenzene (1.65 g, 7.23 mmol) in a mixture of 1,4-dioxane (50 mL) and water (40 mL) at 0° C. was added conc. HCl (17.6 mL), and the mixture was stirred at room temperature overnight. The reaction mixture was cooled to 0° C., neutralized with saturated $NaHCO_3$ solution, and extracted with EtOAc (2×200 mL). The EtOAc solution was dried over anhydrous $Na_2SO_4$, filtered, and evaporated to dryness under reduced pressure. The residue was purified by MPLC on silica gel using a mixture of EtOAc and hexane as eluent to give the titled compound (0.78 g, 71%) as a viscous liquid. $^1$H NMR (400 MHz, $CDCl_3$): δ 9.87 (s, 1H), 7.12 (ddd, 1H, J=11.4, 8.2, 1.6 Hz), 7.08-7.04 (m, 1H), 7.01-6.95 (m, 1H), 6.91 (td. 1H, J=8.2, 1.6 Hz), 4.63 (s, 2H).

Preparative Example 25

Preparation of 2-(2-fluorophenylthio)acetaldehyde (a compound of the formula (IX) wherein $R^b$=2-fluoro, X=S). This compound was prepared by the following 2 steps.

A mixture of 2-fluorothiophenol (1.00 g, 7.80 mmol), bromoacetaldehyde diethyl acetal (1.41 mL, 9.36 mmol), and $Cs_2CO_3$ (3.05 g, 9.36 mmol) in anhydrous DMF (20 mL) was stirred under $N_2$ at room temperature overnight. The reaction mixture was filtered through a sintered funnel, and the filtrate was diluted with water (20 mL). The aqueous mixture was extracted with $Et_2O$ (3×100 mL), and the organic phase was dried over anhydrous $MgSO_4$, filtered, and evaporated to dryness under reduced pressure. The residue was purified by MPLC on silica gel using a mixture of EtOAc and hexane as eluent to give (2,2-diethoxyethyl)(2-fluorophenyl)sulfane (1.81 g, 95%) as a viscous liquid. $^1$H NMR (400 MHz, $CDCl_3$): δ 7.46-7.41 (m, 1H), 7.24-7.18 (m, 1H), 7.09-7.02 (m, 1H), 4.64 (t, 1H, J=5.6 Hz), 3.69-3.61 (m, 2H), 3.56-3.49 (m, 2H), 3.10 (d, 2 H, J=5.6 Hz), 1.17 (t, 6H, J=7.2 Hz).

To a stirred solution of (2,2-diethoxyethyl)(2-fluorophenyl)sulfane (1.00 g, 4.09 mmol) in a mixture of 1,4-dioxane (30 mL) and water (25 mL) at 0° C. was added conc. HCl (9 mL), and the mixture was stirred at room temperature for 2 h. The reaction mixture was cooled to 0° C., neutralized with saturated $NaHCO_3$ solution, and extracted with $CH_2Cl_2$ (3×50 mL). The organic phase was washed with water (50 mL), dried over anhydrous $Na_2SO_4$, filtered, and evaporated to dryness under reduced pressure to give the titled compound (0.59 g, 85%) as a viscous liquid, which was immediately used for the next step without further purification. $^1$H NMR (400 MHz, $CDCl_3$): δ 9.56 (td, 1H, J=3.2, 1.2 Hz), 7.42-7.38 (m, 1H), 7.31-7.25 (m, 1 H), 7.12-7.06 (m, 2H), 3.58 (d, 2H, J=3.2 Hz).

Preparative Example 26

Preparation of 3-(methyl(2-oxoethyl)amino)benzonitrile (a compound of the formula (IX) wherein $R^b$=3-cyano, X=NMe). This compound was prepared by the following 3 steps started with commercially available 3-aminobenzonitrile.

To a stirred solution of 3-aminobenzonitrile (2.50 g, 21.10 mmol) in anhydrous DMSO (30 mL) at 0° C. was added NaH (0.61 g, 25.39 mmol) portionwise, and the mixture was stirred at room temperature for 20 min and then treated with bromoacetaldehyde diethyl acetal (4.20 g, 21.10 mmol). After 2 h, to it, saturated aqueous $NH_4Cl$ (20 mL) was added slowly at 0° C., and the reaction mixture was extracted with EtOAc (2×50 mL). The EtOAc solution was dried over anhydrous $Na_2SO_4$, filtered, and evaporated to dryness under reduced pressure. The residue was purified by MPLC on silica gel using EtOAc and hexane as eluent to give 3-(2,2-diethoxyethylamino)benzonitrile (0.86 g, 17%) as a light orange oil. $^1$H NMR (400 MHz, $CDCl_3$): δ 7.22 (td, 1H, J=7.8, 0.6 Hz), 6.97 (m, 1H), 6.84-6.81 (m, 2H), 4.67 (t, 1H, J=5.4 Hz), 3.77-3.69 (m, 2H), 3.61-3.53 (m, 2H), 3.24 (d, 2H, J=5.6 Hz), 1.24 (t, 6H, J=7.0 Hz).

To a stirred solution of 3-(2,2-diethoxyethylamino)benzonitrile (0.84 g, 3.59 mmol) in anhydrous DMF (5 mL) at 0° C. was added NaH (0.10 g, 4.30 mmol) portionwise. After 20 min, MeI (0.61 g, 4.30 mmol) was added, and the mixture was stirred at room temperature for 6 h. The reaction mixture was cooled to 0° C., and to it, aqueous $NH_4Cl$ (10 mL) solution was added dropwise. The aqueous mixture was extracted with $CHCl_3$ (2×30 mL), and the organic phase was dried over anhydrous $Na_2SO_4$, filtered, and evaporated to dryness under reduced pressure. The residue was purified by MPLC on silica gel using a mixture of EtOAc and hexane as eluent to give 3-((2,2-diethoxyethyl)(methyl)amino)benzonitrile (0.65 g, 73%) as a viscous liquid. $^1$H NMR (400 MHz, $CDCl_3$): δ 7.28-7.24 (m, 1H), 6.96-6.93 (m, 3H), 4.60 (t, 1H, J=5.2 Hz), 3.76-3.69 (m, 2H), 3.55-3.47 (m, 2H), 3.46 (d, 2H, J=5.2 Hz), 3.02 (s, 3H), 1.20 (t, 6H, J=7.0 Hz).

To a stirred solution of 3-((2,2-diethoxyethyl)(methyl)amino)benzonitrile (0.65 g, 2.61 mmol) in anhydrous dioxane (6 mL) at 0° C. was added 1 N HCl (4.30 mmol) dropwise, and the mixture was stirred at room temperature for 1 h. The reaction mixture was cooled to 0° C., neutralized with aqueous $NaHCO_3$ solution, and extracted with $CHCl_3$ (2×30 mL). The $CHCl_3$ solution was dried over anhydrous $Na_2SO_4$, filtered, and evaporated to dryness under reduced pressure to give the titled compound (0.24 g, 52%) as a viscous liquid, which was used for the next step without further purification. $^1$H NMR (400 MHz, $CDCl_3$): δ 9.74 (t, 1H, J=0.8 Hz), 7.29 (ddd, 1H, J=8.8, 7.4, 0.8 HZ), 7.02 (ddd, 1H, J=7.4, 0.8, 1.2 Hz), 6.86 (dd, 1H, J=2.4, 1.2 Hz), 6.82 (ddd, 1H, J=8.8, 2.4, 1.2 Hz) 4.14 (d, 2H, J=0.8 Hz), 3.10 (s, 3H).

Preparative Example 27

Preparation of 2-((2-fluorophenyl)(methyl)amino)acetaldehyde (a compound of the formula (IX) wherein $R^b$=2-fluoro, X=NMe). This compound was prepared by the following 3 steps started with commercially available 2-fluoroaniline.

A stirred mixture of 2-fluoroaniline (2.00 g, 17.90 mmol), bromoacetaldehyde dimethyl acetal (3.25 mL, 21.40 mmol), and $Cs_2CO_3$ (11.70 g, 35.80 mmol) in anhydrous DMF (10 mL) was heated to 120° C. overnight. The reaction mixture was evaporated to dryness under reduced pressure, and the residue was extracted with $Et_2O$ (2×150 mL). The $Et_2O$ solution was washed with water (4×50 mL) and brine (2×50 mL), dried over anhydrous $MgSO_4$, filtered, and evaporated to dryness under reduced pressure. The residue was purified by MPLC on silica gel using a mixture of EtOAc and hexane as eluent to give N-(2,2-diethoxyethyl)-2-fluoroaniline (2.00 g, 49%) as a colorless oil. $^1$H NMR (400 MHz, CDCl$_3$): δ 7.03-6.95 (m, 2H), 6.82-6.77 (m, 1H), 6.71-6.65 (m, 1H), 4.72 (t, 1H, J=5.6 Hz), 3.78-3.71 (m, 2H), 3.62-3.54 (m, 2H), 3.29 (d, 2H, J=5.6 Hz), 1.26-1.22 (m, 6H).

To a stirred solution of N-(2,2-diethoxyethyl)-2-fluoroaniline (1.00 g, 4.40 mmol) in anhydrous DMF (10 mL) at 0° C. was added NaH (0.16 g, 6.60 mmol) portionwise. After 30 min, MeI (0.5 mL, 8.80 mmol) was added, and the mixture was stirred at room temperature overnight. The reaction mixture was extracted with EtOAc (2×100 mL), and the EtOAc solution was washed with water (50 mL) and brine (50 mL), dried over anhydrous Na$_2$SO$_4$, filtered, and evaporated to dryness under reduced pressure to give N-(2,2-diethoxyethyl)-2-fluoro-N-methylaniline (0.41 g, 38%) as a colorless oil. $^1$H NMR (400 MHz, CDCl$_3$): δ 7.05-6.96 (m, 3 H), 6.83-6.81 (m, 1H), 4.69 (t, 1H, J=5.2 Hz), 3.72-3.64 (m, 2H), 3.55-3.49 (m, 2H), 3.33 (dd, 2H, J=5.2, 1.2 Hz), 2.97 (s, 3H), 1.19-1.53 (m, 6H).

To a stirred solution of N-(2,2-diethoxyethyl)-2-fluoro-N-methylaniline (0.40 g, 1.60 mmol) in 1,4-dioxane (5 mL) at 0° C. was added 2.5 N HCl (5 mL) dropwise, and the mixture was stirred at room temperature overnight. The reaction mixture was cooled to 0° C., neutralized with saturated NaHCO$_3$ solution, and extracted with CHCl$_3$ (2×50 mL). The CHCl$_3$ solution was washed with water (20 mL) and brine (20 mL), dried over Na$_2$SO$_4$, filtered, and evaporated to dryness under reduced pressure to give the titled compound (0.27 g, 98%) as a colorless oil, which was used for next step without further purification. $^1$H NMR (400 MHz, CDCl$_3$): δ 9.80 (dd, 1H, J=2.4, 1.2 Hz), 7.07-6.89 (m, 4H), 3.91 (dd, 2H, J=1.8, 0.8 Hz), 2.97 (s, 3H).

Practice Example 1

Preparation of N-((4-([1,2,4]triazolo[1,5-a]pyridin-6-yl)-5-(6-methylpyridin-2-yl)-1H-imidazol-2-yl)methyl)-3-vinylaniline (Example 37)

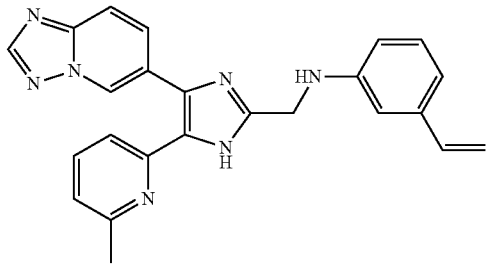

To a stirred solution of 4-([1,2,4]triazolo[1,5-a]pyridin-6-yl)-5-(6-methylpyridin-2-yl)-1H-imidazole-2-carbaldehyde (4.00 g, 13.14 mmol) in 1,2-dichloroethane (240 mL) were added 3-vinylaniline (2.36 g, 19.71 mmol) and AcOH (0.79 g, 13.14 mmol), and the mixture was heated at 80° C. for 2 h. The reaction mixture was cooled to 0° C. and, to it, was added NaBH(OAc)$_3$ (5.56 g, 26.20 mmol). The mixture was stirred at 40° C. overnight, and then the pH of the reaction mixture was adjusted to 7-8 at 0° C. with 10% K$_2$CO$_3$ solution. The reaction mixture was extracted with 5% MeOH in CHCl$_3$ (2×200 mL), and the organic phase was dried over anhydrous Na$_2$SO$_4$, filtered, and evaporated to dryness under reduced pressure. The residue was purified by MPLC on silica gel using a mixture of MeOH and CH$_2$Cl$_2$ (1:19 (v/v)) as eluent to give the titled compound (2.89 g, 63%) as a solid. $^1$H NMR (400 MHz, CDCl$_3$) δ 10.59 (br s, 1H), 8.94 (s, 1H), 8.37 (s, 1H), 7.81 (d, 1H, J=9.2 Hz), 7.77 (d, 1H, J=9.2 Hz), 7.45 (t, 1H, J=7.8 Hz), 7.20 (br d, 1H, overlapped, J=7.6 Hz), 7.15 (t, 1H, overlapped, J=7.8 Hz), 7.00 (d, 1H, J=8.0 Hz), 6.86 (d, 1H, J=7.6 Hz), 6.75 (t, 1H, J=2.0 Hz), 6.63 (dd, 1H, overlapped, J=17.6, 10.8 Hz), 6.61 (dd, 1H, overlapped, J=8.0, 2.0 Hz), 5.69 (dd, 1H, J=17.6, 0.8 Hz), 5.21 (dd, 1H, J=10.8, 0.8 Hz), 4.55 (s, 2H), 4.39 (br s, 1H), 2.51 (s, 3H); MS (ESI) m/z 408.21 (MH$^+$).

Practice Example 2

Preparation of N-((4-([1,2,4]triazolo[1,5-a]pyridin-6-yl)-5-(6-methylpyridin-2-yl)-1H-imidazol-2-yl)methyl)-3-vinylaniline hydrochloride (Example 38)

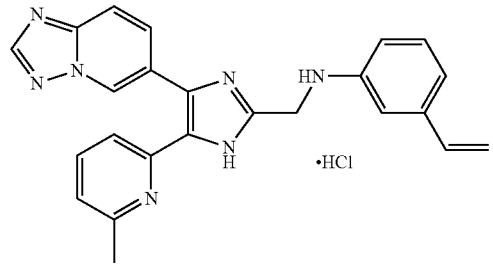

A stirred suspension of N-((4-([1,2,4]triazolo[1,5-a]pyridin-6-yl)-5-(6-methylpyridin-2-yl)-1H-imidazol-2-yl)methyl)-3-vinylaniline (1.00 g, 2.45 mmol) in anhydrous CHCl$_3$ (12 mL) was heated at 50° C. to give a clear solution. The CHCl$_3$ solution was cooled to 0° C. and, to it, was added 1.0 M HCl in Et$_2$O (7.36 mL, 7.36 mmol). After 5 min, the precipitates were filtered under N$_2$ and dried thoroughly over P$_2$O$_5$ in vacuo to give the titled compound (1.07 g, 98%) as a yellow powder. $^1$H NMR (400 MHz, DMSO-d$_6$) δ 9.49 (dd, 1H, J=1.6, 0.8 Hz), 8.65 (s, 1H), 7.97 (dd, 1H, J=9.2, 0.8 Hz), 7.86 (dd, 1H, overlapped, J=9.2, 1.6 Hz), 7.85 (t, 1H, overlapped, J=7.8 Hz), 7.65 (d, 1H, J=8.0 Hz), 7.38 (d, 1H, J=7.6 Hz), 7.12 (t, 1H, J=7.8 Hz), 6.91 (t, 1H, J=1.6 Hz), 6.79 (d, 1H, J=7.6 Hz), 6.71 (dd, 1H, J=8.0, 1.6 Hz), 6.64 (dd, 1H, J=17.6, 11.2 Hz), 5.80 (dd, 1H, J=17.6, 0.8 Hz), 5.20 (dd, 1H, J=11.2, 0.8 Hz), 4.79 (s, 2H), 2.51 (s, 3H).

Practice Example 3

Preparation of N-((4-([1,2,4]triazolo[1,5-a]pyridin-6-yl)-5-(6-methylpyridin-2-yl)-1H-imidazol-2-yl)methyl)-3-vinylaniline sulfate (Example 39)

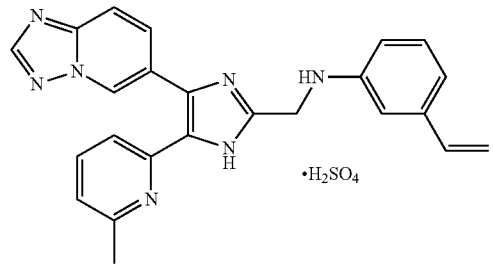

To a stirred suspension of N-((4-([1,2,4]triazolo[1,5-a]pyridin-6-yl)-5-(6-methylpyridin-2-yl)-1H-imidazol-2-yl)methyl)-3-vinylaniline (100 mg, 0.25 mmol) in anhydrous EtOH (2 mL) at 0° C. was added 10% $H_2SO_4$ in anhydrous EtOH (0.20 mL, 0.37 mmol). The mixture was allowed to warm to room temperature and stirred for 10 min. The reaction mixture was diluted with anhydrous $Et_2O$ (8 mL) and stirred for an additional 10 min. The precipitates were filtered under $N_2$, washed with anhydrous $Et_2O$ (4×4 mL), and then dried thoroughly over $P_2O_5$ in vacuo to give the titled compound (79 mg, 64%) as a yellow solid. $^1$H NMR (400 MHz, DMSO-$d_6$) δ 9.40 (dd, 1H, J=1.6, 0.8 Hz), 8.63 (s, 1H), 7.98 (dd, 1H, J=9.2, 0.8 Hz), 7.84 (t, 1H, J=8.0 Hz), 7.76 (dd, 1H, J=9.2, 1.6 Hz), 7.43 (d, 1H, J=7.6 Hz), 7.40 (d, 1H, J=8.0 Hz), 7.13 (t, 1H, J=7.8 Hz), 6.80 (br s, 1H), 6.79 (d, 1H, overlapped, J=7.6 Hz), 6.64 (dd, 1H, overlapped, J=17.6, 11.2 Hz), 6.63 (dd, 1H, overlapped, J=7.6, 2.0 Hz), 5.74 (dd, 1H, J=17.6, 0.8 Hz), 5.21 (dd, 1H, J=11.2, 0.8 Hz), 4.68 (s, 2H), 2.58 (s, 3H).

Practice Example 4

Preparation of 3-((4-([1,2,4]triazolo[1,5-a]pyridin-6-yl)-5-(6-methylpyridin-2-yl)-1H-imidazol-2-yl)methylamino)-4-((dimethylamino)methyl)benzonitrile (Example 116)

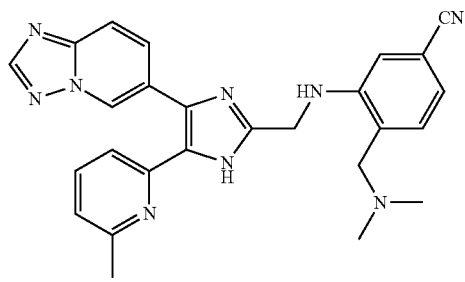

To a stirred solution of 4-((1,2,4)triazolo(1,5-a)pyridin-6-yl)-5-(6-methylpyridin-2-yl)-1H-imidazole-2-carbaldehyde (0.50 g, 1.64 mmol) in 1,2-dichloroethane (30 mL) were added 3-amino-4-((dimethylamino)methyl)benzonitrile (0.43 g, 2.46 mmol) and AcOH (0.20 g, 3.29 mmol), and the mixture was heated at 80° C. overnight. The reaction mixture was concentrated under reduced pressure, and the residue was dissolved in anhydrous MeOH (30 mL). To a methanolic solution at 0° C. was added $NaBH_4$ (0.25 g, 6.57 mmol), and then the mixture was allowed to warm to room temperature and stirred for an additional 3 h. The pH of the reaction mixture was adjusted to 7-8 at 0° C. with 1 N HCl, and then MeOH was removed under reduced pressure. The aqueous mixture was extracted with $CH_2Cl_2$ (2×50 mL), and the $CH_2Cl_2$ solution was dried over anhydrous $Na_2SO_4$, filtered, and evaporated to dryness under reduced pressure. The residue was purified by MPLC on silica gel using a mixture of MeOH and $CH_2Cl_2$ (1:19 (v/v)) as eluent to give the titled compound (0.60 g, 79%) as a white solid. $^1$H NMR (400 MHz, $CDCl_3$) δ 8.99 (s, 1H), 8.36 (s, 1H), 7.86 (dd, 1H, J=9.2, 1.6 Hz), 7.78 (dd, 1H, J=9.2, 0.8 Hz), 7.47 (t, 1H, J=7.6 Hz), 7.23 (br d, 1H, J=7.6 Hz), 7.09 (d, 1H, J=7.6 Hz), 7.01 (d, 1H, J=7.6 Hz), 6.98 (dd, 1H, J=7.6, 1.6 Hz), 6.93 (br s, 1H), 4.59 (s, 2H), 3.63 (s, 2H), 2.53 (s, 3H), 2.33 (s, 6H); MS (ESI) m/z 464.23 ($MH^+$).

The compounds listed in the following Table 1 were prepared in an analogous manner to those described in the Practice Examples 1-4 above. The mass spectroscopy data of these compounds are included in the Table 1.

TABLE 1

| Example | Structure | $^1$H NMR (ppm) | MS (ESI) m/z ($MH^+$) |
|---|---|---|---|
| 1 | 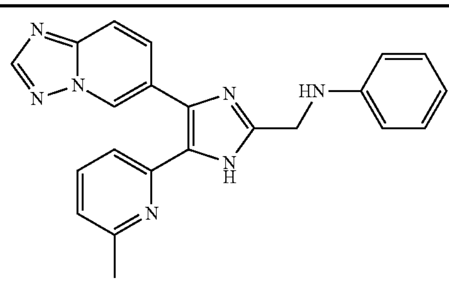 | (400 MHz, $CDCl_3$) δ 10.43 (br s, 1H), 8.96 (s, 1H), 8.37 (s, 1H), 7.82 (dd, 1H, J = 9.2, 1.6 Hz), 7.77 (dd, 1H, J = 9.2, 0.8 Hz), 7.45 (t, 1H, J = 7.6 Hz), 7.25-7.19 (m, 3H), 7.01 (d, 1H, J = 7.6 Hz), 6.80 (tt, 1H, J = 8.0, 1.2 Hz), 6.74-6.72 (m, 2H), 4.55 (s, 2H), 2.53 (s, 3H) | 382.19 |
| 2 | 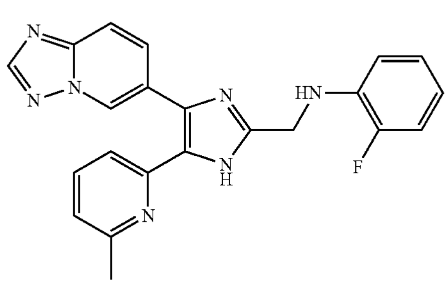 | (400 MHz, $CDCl_3$) δ 11.34 (br s, 1H), 8.96 (dd, 1H, J = 1.6, 0.8 Hz), 8.35 (s, 1H), 7.81 (dd, 1H, J = 9.2, 1.6 Hz), 7.74 (dd, 1H, J = 9.2, 0.8 Hz), 7.45 (t, 1H, J = 7.6 Hz), 7.23 (d, 1H, J = 7.6 Hz), 6.97-6.90 (m, 2H), 6.94 (dd, 1H, J = 8.0, 1.2 Hz), 6.72 (td, 1H, J = 8.4, 1.6 Hz), 6.69-6.63 (m, 1H), 4.51 (s, 2H), 2.35 (s, 3H). | 400.18 |

TABLE 1-continued

| Example | Structure | ¹H NMR (ppm) | MS (ESI) m/z (MH⁺) |
|---|---|---|---|
| 3 | 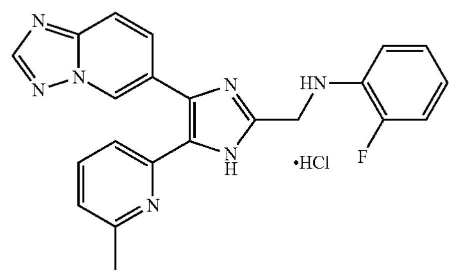 | (400 MHz, DMSO-d₆) δ 9.44 (d, 1H, J = 0.8 Hz), 8.62 (s, 1H), 7.96 (dd, 1H, J = 9.2, 0.8 Hz), 7.83 (t, 1H, J = 8.0 Hz), 7.80 (dd, 1H, J = 9.2, 1.6 Hz), 7.53 (d, 1H, J = 8.0 Hz), 7.38 (d, 1H, J = 7.6 Hz), 7.10 (ddd, 1H, J = 12.0, 8.0, 1.2 Hz), 7.01 (td, 1H, J = 7.6, 1.2 Hz), 6.88 (br t, 1H, J = 8.6 Hz), 6.70-6.64 (m, 1H), 4.75 (s, 2H), 2.54 (s, 3H) | |
| 4 | 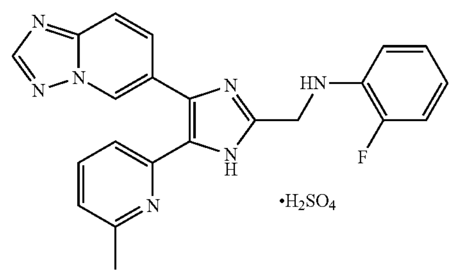 | (400 MHz, DMSO-d₆) δ 9.40 (dd, 1H, J = 2.0, 0.8 Hz), 8.64 (s, 1H), 7.99 (dd, 1H, J = 9.2, 0.8 Hz), 7.85 (t, 1H, J = 8.0 Hz), 7.77 (dd, 1H, J = 9.2, 2.0 Hz), 7.42 (pseudo t, 2H, J = 7.4 Hz), 7.11 (ddd, 1H, J = 12.0, 8.0, 1.2 Hz), 7.02 (td, 1H, J = 7.6, 1.2 Hz), 6.82 (td, 1H, J = 8.0, 1.2 Hz), 6.71-6.65 (m, 1H), 4.73 (s, 2H), 2.59 (s, 3H) | |
| 5 | 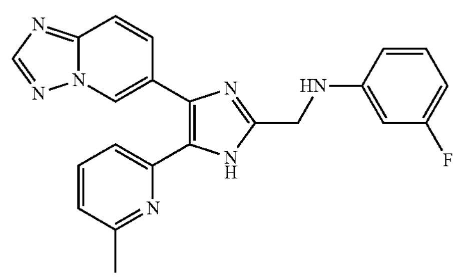 | (400 MHz, CDCl₃) δ 8.94 (t, 1H, J = 1.4 Hz), 8.36 (s, 1H), 7.79 (dd, 1H, J = 9.2, 1.6 Hz), 7.75 (dd, 1H, J = 9.2, 0.8 Hz), 7.46 (t, 1H, J = 7.8 Hz), 7.23 (d, 1H, J = 8.0 Hz), 7.13-7.07 (m, 1H), 7.01 (d, 1H, J = 7.6 Hz), 6.47-6.41 (m, 2H), 6.37 (dt, 1H, J = 8.8, 2.4 Hz), 4.49 (s, 2H), 2.49 (s, 3H) | 400.19 |
| 6 | 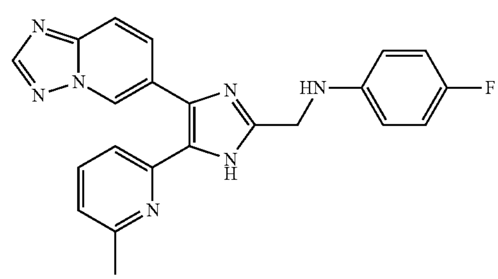 | (400 MHz, CDCl₃) δ 8.95 (dd, 1H, J = 1.6, 1.2 Hz), 8.37 (s, 1H), 7.80 (dd, 1H, J = 9.2, 1.6 Hz), 7.76 (dd, 1H, J = 9.2, 1.2 Hz), 7.46 (t, 1H, J = 7.6 Hz), 7.23 (d, 1H, J = 7.6 Hz), 7.01 (d, 1H, J = 7.6 Hz), 6.92-6.88 (m, 2H), 6.65-6.62 (m, 2H), 4.49 (s, 2H), 2.51 (s, 3H) | 400.19 |
| 7 | 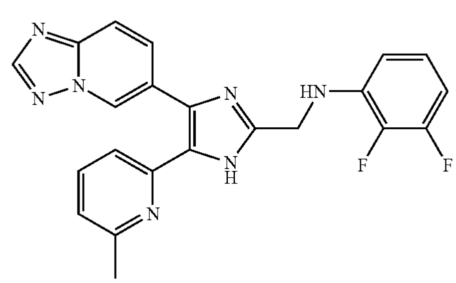 | (400 MHz, CDCl₃) δ 8.96 (br s, 1H), 8.38 (s, 1H), 7.82 (dd, 1H, J = 9.2, 1.6 Hz), 7.78 (dd, 1H, J = 9.2, 0.8 Hz), 7.47 (t, 1H, J = 7.6 Hz), 7.24 (d, 1H, J = 7.6 Hz), 7.02 (dd, 1H, J = 7.6, 0.4 Hz), 6.94-6.88 (m, 1H), 6.60-6.51 (m, 2H), 4.71 (br s, 1H), 4.58 (d, 2H, J = 3.6 Hz), 2.51 (s, 3H) | 418.18 |

TABLE 1-continued

| Example | Structure | ¹H NMR (ppm) | MS (ESI) m/z (MH⁺) |
|---|---|---|---|
| 8 | 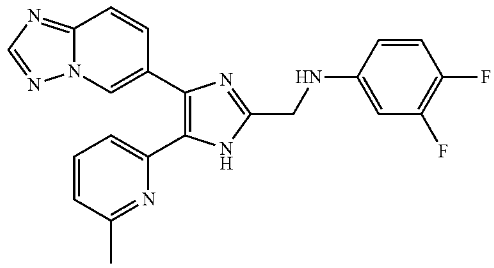 | (400 MHz, CDCl₃) δ 8.94 (t, 1H, J = 1.4 Hz), 8.38 (s, 1H), 7.81 (dd, 1H, overlapped, J = 9.2, 1.6 Hz), 7.78 (dd, 1H, overlapped, J = 9.2, 1.2 Hz), 7.47 (t, 1H, J = 7.8 Hz), 7.24 (d, 1H, J = 8.0 Hz), 7.03 (d, 1H, J = 7.6 Hz), 7.04-6.95 (m, 1H), 6.52 (ddd, 1H, J = 12.4, 6.8, 2.8 Hz), 6.42-6.37 (m, 1H), 4.48 (s, 2H), 2.55 (s, 3H) | 418.18 |
| 9 | 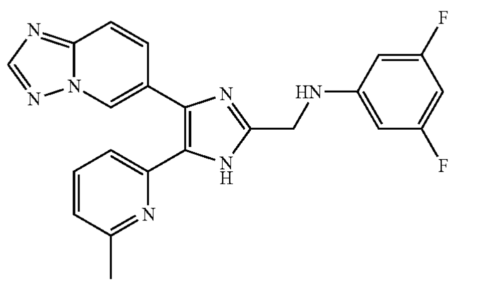 | (400 MHz, CDCl₃) δ 8.94 (t, 1H, J = 1.2 Hz), 8.38 (s, 1H), 7.81 (dd, 1H, overlapped, J = 9.2, 1.6 Hz), 7.79 (dd, 1H, overlapped, J = 9.2, 1.2 Hz), 7.47 (t, 1H, J = 7.8 Hz), 7.24 (d, 1H, J = 8.0 Hz), 7.03 (d, 1H, J = 7.6 Hz), 6.24-6.19 (m, 3H), 4.71 (br s, 1H), 4.50 (s, 2H), 2.55 (s, 3H) | 418.18 |
| 10 | 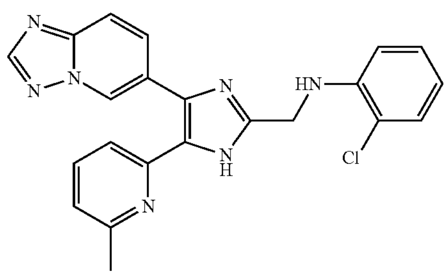 | (400 MHz, CDCl₃) δ 8.97 (br s, 1H), 8.37 (s, 1H), 7.82 (dd, 1H, J = 9.2, 1.6 Hz), 7.77 (dd, 1H, J = 9.2, 1.0 Hz), 7.46 (t, 1H, J = 7.6 Hz), 7.29 (dd, 1H, J = 7.6, 1.6 Hz), 7.23 (br d, 1H, J = 7.6 Hz), 7.01 (td, 1H, J = 8.4, 1.6 Hz), 7.01 (dd, 1H, J = 7.6, 0.4 Hz), 6.75 (dd, 1H, J = 8.8, 1.4 Hz), 6.72 (td, 1H, J = 8.4, 1.6 Hz), 5.01 (br s, 1H), 4.60 (br s, 2H), 2.50 (s, 3H) | 416.16 |
| 11 | 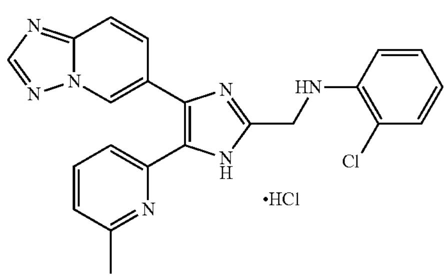 | (400 MHz, DMSO-d₆) δ 9.43 (s, 1H), 8.61 (s, 1H), 7.95 (dd, 1H, J = 9.2, 0.8 Hz), 7.82 (t, 1H, overlapped, J = 7.8 Hz), 7.81 (dd, 1H, overlapped, J = 9.2, 2.0 Hz), 7.49 (d, 1H, J = 8.0 Hz), 7.36 (d, 1H, J = 7.6 Hz), 7.32 (dd, 1H, J = 7.8, 1.4 Hz), 7.17 (td, 1H, J = 8.4, 1.2 Hz), 6.87 (dd, 1H, J = 8.4, 1.2 Hz), 6.69 (td, 1H, J = 7.8, 1.4 Hz), 6.15 (br s, 1H), 4.76 (s, 2H), 2.55 (s, 3H) | |
| 12 | 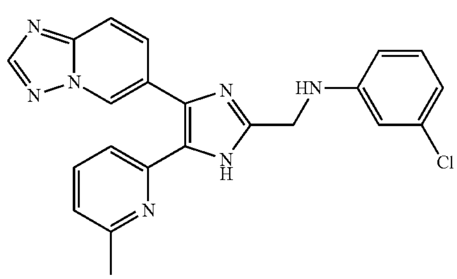 | (400 MHz, CDCl₃) δ 8.95 (t, 1H, J = 1.6 Hz), 8.37 (s, 1H), 7.81 (dd, 1H, J = 9.2, 1.6 Hz), 7.77 (dd, 1H, J = 9.2, 1.2 Hz), 7.47 (t, 1H, J = 7.8 Hz), 7.24 (d, 1H, J = 8.0 Hz), 7.10 (t, 1H, J = 8.0 Hz), 7.02 (d, 1H, J = 7.6 Hz), 6.75 (ddd, 1H, J = 8.0, 2.0, 0.8 Hz), 6.69 (t, 1H, J = 2.0 Hz), 6.57 (ddd, 1H, J = 8.0, 2.4, 0.8 Hz), 4.51 (s, 2H), 2.52 (s, 3H) | 416.16 |

TABLE 1-continued

| Example | Structure | $^1$H NMR (ppm) | MS (ESI) m/z (MH$^+$) |
|---|---|---|---|
| 13 | 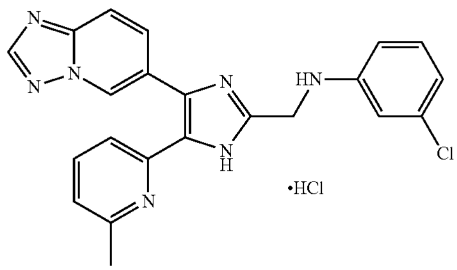 | (400 MHz, DMSO-d$_6$) δ 9.45 (dd, 1H, J = 1.6, 0.8 Hz), 8.63 (s, 1H), 7.97 (dd, 1H, J = 9.2, 0.8 Hz), 7.85 (t, 1H, J = 8.0 Hz), 7.81 (dd, 1H, J = 9.2, 1.6 Hz), 7.56 (d, 1H, J = 8.4 Hz), 7.39 (d, 1H, J = 7.6 Hz), 7.15 (t, 1H, J = 8.0 Hz), 6.80 (t, 1H, J = 2.2 Hz), 6.71-6.65 (m, 2H), 4.71 (s, 2H), 2.54 (s, 3H) | |
| 14 | 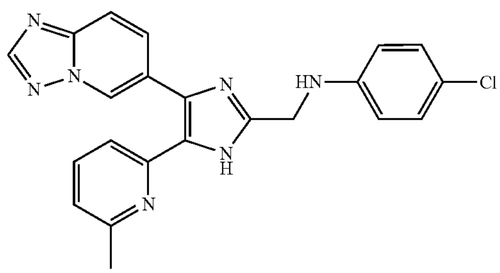 | (400 MHz, CDCl$_3$) δ 8.95 (t, 1H, J = 1.4 Hz), 8.38 (s, 1H), 7.81 (dd, 1H, overlapped, J = 9.2, 1.4 Hz), 7.78 (dd, 1H, overlapped, J = 9.2, 1.2 Hz), 7.47 (t, 1H, J = 7.6 Hz), 7.23 (br d, 1H, J = 7.6 Hz), 7.16 (m, 2H), 7.02 (br d, 1H, J = 7.6 Hz), 6.65 (m, 2H), 4.51 (s, 2H), 2.54 (s, 3H) | 416.16 |
| 15 | 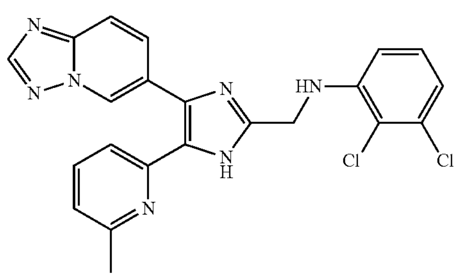 | (400 MHz, CDCl$_3$) δ 11.02 (br s, 1H), 8.97 (s, 1H), 8.36 (s, 1H), 7.81 (dd, 1H, J = 9.2, 1.6 Hz), 7.75 (dd, 1H, J = 9.2, 0.8 Hz), 7.46 (t, 1H, J = 8.0 Hz), 7.24 (d, 1H, J = 8.0 Hz), 7.03 (t, 1H, overlapped, J = 8.0 Hz), 7.00 (d, 1H, overlapped, J = 8.0 Hz), 6.85 (dd, 1H, J = 8.0, 1.6 Hz), 6.63 (dd, 1H, J = 8.0, 1.6 Hz), 5.15 (t, 1H, J = 5.6 Hz), 4.57 (d, 2H, J = 5.6 Hz), 2.43 (s, 3H) | 450.12 |
| 16 | 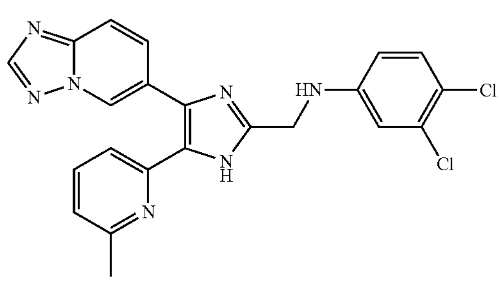 | (400 MHz, CDCl$_3$) δ 8.94 (t, 1H, J = 1.2 Hz), 8.37 (s, 1H), 7.80 (dd, 1H, overlapped, J = 9.2, 1.6 Hz), 7.77 (dd, 1H, overlapped, J = 9.2, 1.2 Hz), 7.47 (t, 1H, J = 8.0 Hz), 7.24 (br d, 1H, J = 8.0 Hz), 7.20 (d, 1H, J = 8.8 Hz), 7.03 (d, 1H, J = 8.0 Hz), 6.77 (d, 1H, J = 2.8 Hz), 6.53 (dd, 1H, J = 8.8, 2.8 Hz), 4.47 (s, 2H), 2.51 (s, 3H) | 450.12 |
| 17 | 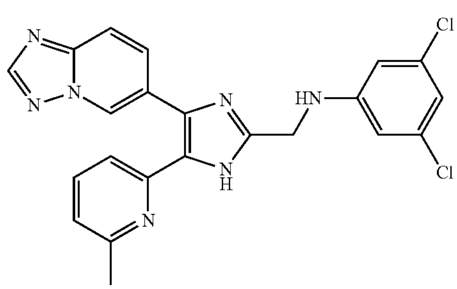 | (400 MHz, CDCl$_3$/CD$_3$OD) δ 8.90 (s, 1H), 8.24 (s, 1H), 7.71 (dd, 1H, J = 9.2, 1.6 Hz), 7.64 (dd, 1H, J = 9.2, 0.8 Hz), 7.45 (t, 1H, J = 7.6 Hz), 7.16 (br d, 1H, J = 7.6 Hz), 6.99 (d, 1H, J = 7.6 Hz), 6.57 (t, 1H, J = 1.6 Hz), 6.51 (d, 2H, J = 1.6 Hz), 4.36 (s, 2H), 2.45 (s, 3H) | 450.12 |

TABLE 1-continued

| Example | Structure | ¹H NMR (ppm) | MS (ESI) m/z (MH⁺) |
|---|---|---|---|
| 18 | 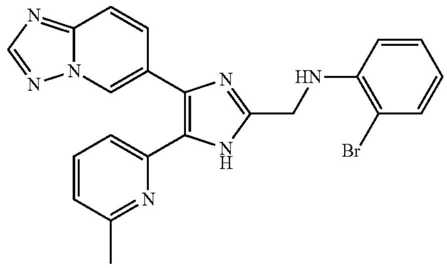 | (400 MHz, CDCl₃) δ 10.94 (br s, 1H), 8.97 (br s, 1H), 8.36 (s, 1H), 7.82 (d, 1H, J = 9.2 Hz), 7.75 (d, 1H, J = 9.2 Hz), 7.45 (t, 1H, overlapped, J = 7.8 Hz), 7.43 (dd, 1H, J = 8.0, 1.6 Hz), 7.21 (d, 1H, J = 8.0 Hz), 7.16 (td, 1H, J = 8.4, 1.2 Hz), 6.99 (d, 1H, J = 7.6 Hz), 6.71 (dd, 1H, J = 8.4, 1.2 Hz), 6.63 (td, 1H, J = 8.0, 1.6 Hz), 4.99 (t, 1H, J = 5.6 Hz), 4.57 (d, 2H, J = 5.6 Hz), 2.44 (s, 3H) | 460.11 |
| 19 | ·HCl | (400 MHz, DMSO-d₆) δ 9.43 (dd, 1H, J = 1.6, 0.8 Hz), 8.62 (s, 1H), 7.96 (dd, 1H, J = 9.2, 0.8 Hz), 7.83 (t, 1H, J = 7.6 Hz), 7.80 (dd, 1H, J = 9.2, 1.6 Hz), 7.50 (d, 1H, J = 7.6 Hz), 7.48 (dd, 1H, J = 8.0, 1.6 Hz), 7.37 (d, 1H, J = 7.6 Hz), 7.21 (td, 1H, J = 7.6, 1.6 Hz), 6.87 (dd, 1H, J = 8.0, 1.2 Hz), 6.63 (td, 1H, J = 7.6, 1.2 Hz), 6.04 (br s 1H), 4.78 (s, 2H), 2.55 (s, 3H) | |
| 20 | 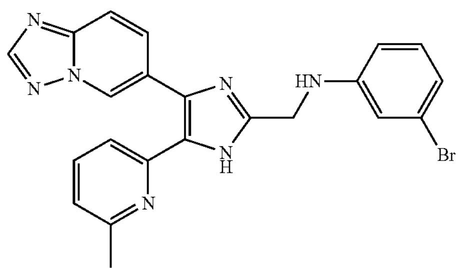 | (400 MHz, CDCl₃) δ 8.89 (br s, 1H), 8.30 (s, 1H), 7.75 (dd, 1H, J = 9.2, 1.6 Hz), 7.69 (d, 1H, J = 9.2 Hz), 7.44 (br t, 1H, J = 7.6 Hz), 7.12 (br d, 1H, J = 7.6 Hz), 7.00 (d, 1H, J = 8.0 Hz), 6.97 (t, 1H, overlapped, J = 8.0 Hz), 6.82-6.78 (m, 2H), 6.58 (ddd, 1H, J = 8.2, 2.4, 0.8 Hz), 4.41 (s, 2H), 2.49 (s, 3H) | 460.11 |
| 21 | ·HCl | (400 MHz, DMSO-d₆) δ 9.44 (d, 1H, J = 0.8 Hz), 8.61 (s, 1H), 7.95 (dd, 1H, J = 9.2, 0.8 Hz), 7.83 (t, 1H, J = 7.8 Hz), 7.82 (dd, 1H, J = 9.2, 1.6 Hz), 7.50 (d, 1H, J = 8.0 Hz), 7.37 (d, 1H, J = 7.6 Hz), 7.08 (t, 1H, J = 8.0 Hz), 6.94 (t, 1H, J = 2.0 Hz), 6.79 (ddd, 1H, J = 7.6, 2.0, 0.8 Hz), 6.71 (ddd, 1H, J = 8.4, 2.0, 0.8 Hz), 4.63 (s, 2H), 2.55 (s, 3H) | |
| 22 | 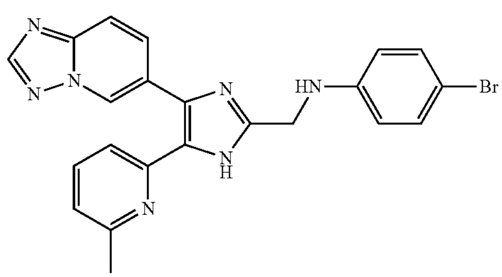 | (400 MHz, CDCl₃) δ 8.94 (br s, 1H), 8.38 (s, 1H), 7.82-7.77 (m, 2H), 7.46 (t, 1H, J = 7.6 Hz), 7.29 (m, 2H), 7.21 (d, 1H, J = 7.6 Hz), 7.02 (d, 1H, J = 7.6 Hz), 6.61 (m, 2H), 4.51 (s, 2H), 4.44 (br s, 1H), 2.54 (s, 3H) | 460.11 |

TABLE 1-continued

| Example | Structure | $^1$H NMR (ppm) | MS (ESI) m/z (MH$^+$) |
|---|---|---|---|
| 23 | 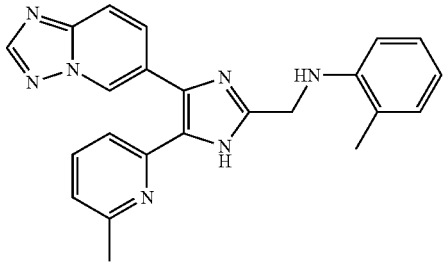 | (400 MHz, CDCl$_3$) δ 8.97 (s, 1H), 8.37 (s, 1H), 7.83 (dd, 1H, J = 9.2, 1.6 Hz), 7.78 (dd, 1H, J = 9.2, 0.8 Hz), 7.46 (t, 1H, J = 7.8 Hz), 7.23 (br d, 1H, J = 7.6 Hz), 7.14 (t, 1H, overlapped, J = 8.0 Hz), 7.12 (d, 1H, overlapped, J = 7.6 Hz), 7.01 (d, 1H, J = 8.0 Hz), 6.76 (td, 1H, J = 7.6, 0.8 Hz), 6.69 (d, 1H, J = 7.6 Hz), 4.61 (s, 2H), 2.54 (s, 3H), 2.26 (s, 3H) | 396.21 |
| 24 | 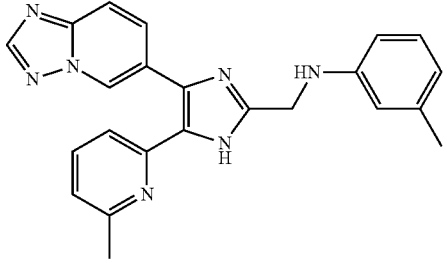 | (400 MHz, CDCl$_3$) δ 8.96 (dd, 1H, J = 1.6, 1.2 Hz), 8.37 (s, 1H), 7.82 (dd, 1H, J = 9.2, 1.6 Hz), 7.78 (dd, 1H, J = 9.2, 1.2 Hz), 7.46 (t, 1H, J = 7.8 Hz), 7.22 (br d, 1H, J = 8.0 Hz), 7.11 (t, 1H, J = 7.8 Hz), 7.01 (d, 1H, J = 7.6 Hz), 6.63 (dt, 1H, J = 7.6, 0.8 Hz), 6.57-6.53 (m, 2H), 4.55 (s, 2H), 2.54 (s, 3H), 2.29 (s, 3H) | 396.21 |
| 25 | 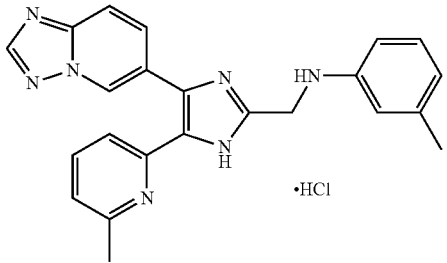 | (400 MHz, DMSO-d$_6$) δ 9.45 (dd, 1H, J = 1.6, 0.8 Hz), 8.63 (s, 1H), 7.97 (dd, 1H, J = 9.2, 0.8 Hz), 7.83 (t, 1H, J = 8.0 Hz), 7.81 (dd, 1H, J = 9.2, 1.6 Hz), 7.56 (d, 1H, J = 8.0 Hz), 7.37 (d, 1H, J = 8.0 Hz), 7.02 (t, 1H, J = 7.8 Hz), 6.60 (s, 1H), 6.54 (dd, 1H, J = 8.0, 2.0 Hz), 6.49 (d, 1H, J = 7.6 Hz), 4.69 (s, 2H), 2.52 (s, 3H), 2.21 (s, 3H) | |
| 26 | 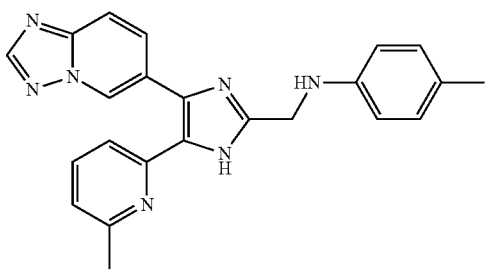 | (400 MHz, CDCl$_3$) δ 8.96 (t, 1H, J = 1.2 Hz), 8.37 (s, 1H), 7.82 (d d, 1H, J = 9.2, 1.6 Hz), 7.77 (dd, 1H, J = 9.2, 0.8 Hz), 7.45 (t, 1H, J = 7.8 Hz), 7.22 (br d, 1H, J = 8.0 Hz), 7.03 (m, 2H), 7.02 (d, 1H, overlapped, J = 7.6 Hz), 6.65 (m, 2H), 4.53 (s, 2H), 2.53 (s, 3H), 2.25 (s, 3H) | 396.21 |
| 27 | 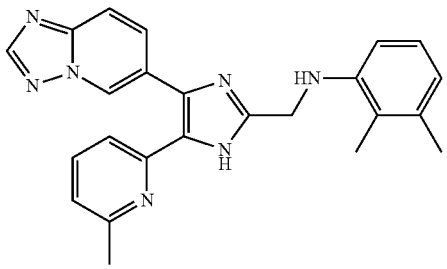 | (400 MHz, CDCl$_3$) δ 8.97 (s, 1H), 8.37 (s, 1H), 7.83 (dd, 1H, J = 9.2, 1.6 Hz), 7.78 (dd, 1H, J = 9.2, 0.8 Hz), 7.45 (t, 1H, J = 7.8 Hz), 7.22 (br d, 1H, J = 7.6 Hz), 7.03 (t, 1H, overlapped, J = 7.8 Hz), 7.02 (d, 1H, overlapped, J = 8.0 Hz), 6.96 (d, 1H, J = 7.6 Hz), 6.58 (d, 1H, J = 8.0 Hz), 4.59 (s, 2H), 2.54 (s, 3H), 2.31 (s, 3H), 2.17 (s, 3H) | 410.23 |

TABLE 1-continued

| Example | Structure | $^1$H NMR (ppm) | MS (ESI) m/z (MH$^+$) |
|---|---|---|---|
| 28 | 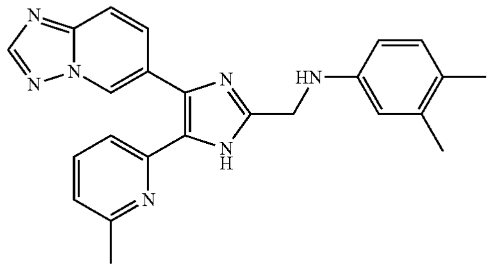 | (400 MHz, CDCl$_3$) δ 8.96 (d, 1H, J = 1.2 Hz), 8.37 (s, 1H), 7.82 (dd, 1H, J = 9.2, 1.6 Hz), 7.77 (dd, 1H, J = 9.2, 0.8 Hz), 7.45 (t, 1H, J = 7.6 Hz), 7.22 (br d, 1H, J = 8.0 Hz), 7.00 (d, 1H, J = 7.6 Hz), 6.98 (d, 1H, J = 8.0 Hz), 6.57 (d, 1H, J = 2.4 Hz), 6.50 (dd, 1H, J = 8.0, 2.4 Hz), 4.53 (s, 2H), 2.54 (s, 3H), 2.20 (s, 3H), 2.16 (s, 3H) | 410.23 |
| 29 | 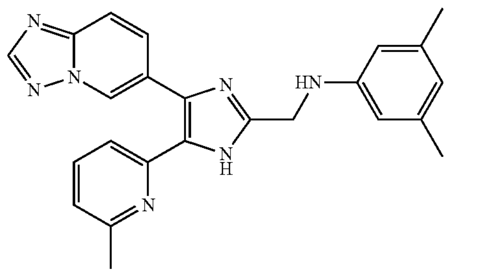 | (400 MHz, CDCl$_3$) δ 8.95 (dd, 1H, J = 1.6, 1.2 Hz), 8.36 (s, 1H), 7.79 (dd, 1H, J = 9.2, 1.6 Hz), 7.74 (dd, 1H, J = 9.2, 1.2 Hz), 7.45 (t, 1H, J = 7.8 Hz), 7.22 (d, 1H, J = 8.0 Hz), 6.99 (d, 1H, J = 7.6 Hz), 6.44 (br s, 1H), 6.31 (s, 2H), 4.49 (s, 2H), 2.48 (s, 3H), 2.21 (s, 6H) | 410.23 |
| 30 | 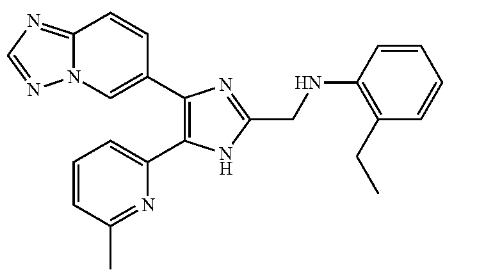 | (400 MHz, CDCl$_3$) δ 8.97 (br s, 1H), 8.37 (s, 1H), 7.83 (dd, 1H, J = 9.2, 1.6 Hz), 7.78 (dd, 1H, J = 9.2, 0.8 Hz), 7.46 (t, 1H, J = 7.8 Hz), 7.23 (br d, 1H, J = 7.6 Hz), 7.16-7.11 (m, 2H), 7.01 (d, 1H, J = 7.6 Hz), 6.80 (td, 1H, J = 7.6, 1.2 Hz), 6.71 (dd, 1H, J = 8.4, 1.2 Hz), 4.60 (s, 2H), 2.60 (q, 2H, J = 7.6 Hz), 2.52 (s, 3H), 1.32 (t, 3H, J = 7.6 Hz) | 410.23 |
| 31 | 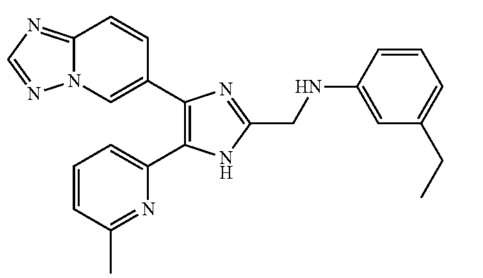 | (400 MHz, CDCl$_3$) δ 8.96 (d, 1H, J = 1.2 Hz), 8.37 (s, 1H), 7.82 (dd, 1H, J = 9.2, 1.6 Hz), 7.77 (dd, 1H, J = 9.2, 1.2 Hz), 7.45 (t, 1H, J = 7.8 Hz), 7.22 (br d, 1H, J = 8.0 Hz), 7.14 (t, 1H, J = 7.8 Hz), 7.01 (d, 1H, J = 7.6 Hz), 6.66 (dd, 1H, J = 7.6, 0.8 Hz), 6.58 (d, 1H, J = 2.0 Hz), 6.55 (dd, 1H, J = 7.6, 2.0 Hz), 4.55 (s, 2H), 2.58 (q, 2H, J = 7.6 Hz), 2.53 (s, 3H), 1.21 (t, 3H, J = 7.6 Hz) | 410.23 |
| 32 | 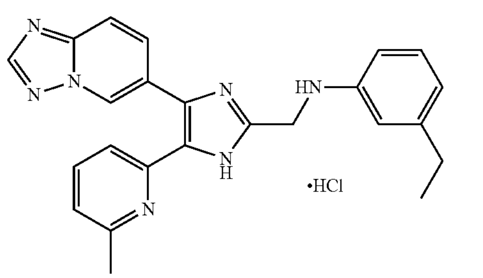 | (400 MHz, DMSO-d$_6$) δ 9.45 (dd, 1H, J = 1.6, 0.8 Hz), 8.63 (s, 1H), 7.97 (dd, 1H, J = 9.2, 0.8 Hz), 7.83 (t, 1H, J = 8.0 Hz), 7.81 (dd, 1H, J = 9.2, 1.6 Hz), 7.57 (d, 1H, J = 8.0 Hz), 7.37 (dd, 1H, J = 8.0 Hz), 7.05 (t, 1H, J = 7.6 Hz), 6.64 (d, 1H, J = 1.6 Hz), 6.57-6.52 (m, 2H), 4.71 (s, 2H), 2.53 (s, 3H), 2.50 (q, 2H, J = 7.6 Hz), 1.14 (t, 3H, J = 7.6 Hz) | |

TABLE 1-continued

| Example | Structure | $^1$H NMR (ppm) | MS (ESI) m/z (MH$^+$) |
|---|---|---|---|
| 33 | 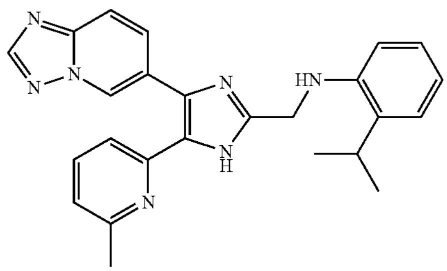 | (400 MHz, CDCl$_3$) δ 8.97 (br s, 1H), 8.37 (s, 1H), 7.82 (dd, 1H, J = 9.2, 1.6 Hz), 7.76 (dd, 1H, J = 9.2, 0.8 Hz), 7.45 (t, 1H, J = 7.8 Hz), 7.23 (br d, 1H, overlapped, J = 8.0 Hz), 7.21 (dd, 1H, overlapped, J = 7.6, 1.6 Hz), 7.12 (td, 1H, J = 7.6, 1.6 Hz), 7.00 (d, 1H, J = 7.6 Hz), 6.83 (td, 1H, J = 7.6, 1.2 Hz), 6.71 (dd, 1H, J = 8.0, 1.2 Hz), 4.58 (s, 2H), 3.00 (heptet, 1H, J = 6.8 Hz), 2.50 (s, 3H), 1.31 (d, 6H, J = 6.8 Hz) | 424.24 |
| 34 | 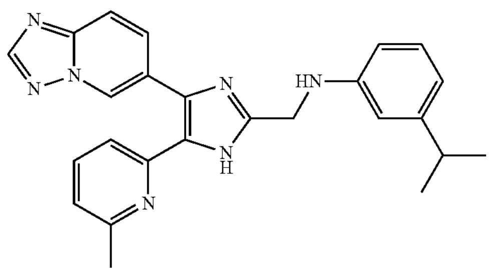 | (400 MHz, CDCl$_3$) δ 8.96 (dd, 1H, J = 1.4, 0.8 Hz), 8.35 (s, 1H), 7.79 (dd, 1H, J = 9.2, 1.4 Hz), 7.73 (dd, 1H, J = 9.2, 0.8 Hz), 7.44 (t, 1H, J = 7.8 Hz), 7.21 (d, 1H, J = 7.6 Hz), 7.11 (t, 1H, J = 7.8 Hz), 6.99 (dd, 1H, J = 7.8, 0.4 Hz), 6.67 (d, 1H, J = 7.6 Hz), 6.57 (t, 1H, J = 2.4 Hz), 6.50 (ddd, 1H, J = 8.0, 2.4, 0.8 Hz), 4.51 (s, 2H), 2.80 (heptet, 1H, J = 6.8 Hz), 2.47 (s, 3H), 1.20 (d, 6H, J = 6.8 Hz) | 424.24 |
| 35 | 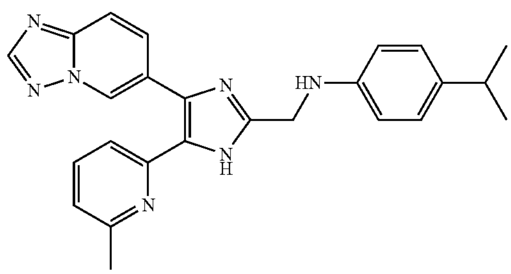 | (400 MHz, CDCl$_3$) δ 8.96 (t, 1H, J = 1.2 Hz), 8.36 (s, 1H), 7.81 (dd, 1H, J = 9.2, 1.6 Hz), 7.75 (d, 1H, J = 9.2 Hz), 7.44 (t, 1H, J = 7.8 Hz), 7.21 (d, 1H, J = 8.0 Hz), 7.06 (m, 2H), 6.99 (d, 1H, J = 7.6 Hz), 6.64 (m, 2H), 4.50 (s, 2H), 2.80 (heptet, 1H, J = 6.8 Hz), 2.48 (s, 3H), 1.19 (d, 6H, J = 6.8 Hz) | 424.24 |
| 36 | 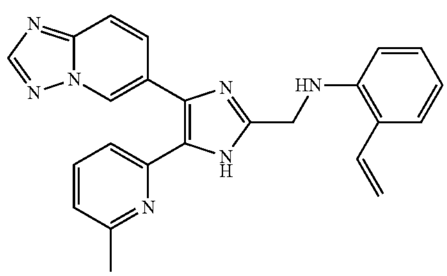 | (400 MHz, CDCl$_3$) δ 8.96 (br s, 1H), 8.35 (s, 1H), 7.80 (dd, 1H, J = 9.2, 1.6 Hz), 7.73 (dd, 1H, J = 9.2, 0.8 Hz), 7.44 (t, 1H, J = 7.8 Hz), 7.28 (dd, 1H, J = 7.6, 1.2 Hz), 7.22 (br d, 1H, J = 8.0 Hz), 7.15 (td, 1H, J = 7.8, 1.2 Hz), 6.99 (d, 1H, J = 7.6 Hz), 6.79 (dd, 1H, overlapped, J = 17.2, 11.2 Hz), 6.78 (td, 1H, overlapped, J = 7.6, 0.8 Hz), 6.68 (dd, 1H, J = 8.2, 1.0 Hz), 5.62 (dd, 1H, J = 17.2, 1.4 Hz), 5.34 (dd, 1H, J = 11.2, 1.4 Hz), 4.53 (s, 2H), 2.45 (s, 3H) | 408.21 |
| 37 | 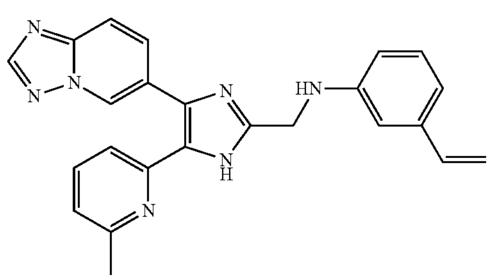 | (400 MHz, CDCl$_3$) δ 10.59 (br s, 1H), 8.94 (s, 1H), 8.37 (s, 1H), 7.81 (d, 1H, J = 9.2 Hz), 7.77 (d, 1H, J = 9.2 Hz), 7.45 (t, 1H, J = 7.8 Hz), 7.20 (br d, 1H, overlapped, J = 7.6 Hz), 7.15 (t, 1H, overlapped, J = 7.8 Hz), 7.00 (d, 1H, J = 8.0 Hz), 6.86 (d, 1H, J = 7.6 Hz), 6.75 (t, 1H, J = 2.0 Hz), 6.63 (dd, 1H, overlapped, J = 17.6, 10.8 Hz), 6.61 (dd, 1H, overlapped, J = 8.0, 2.0 Hz), 5.69 (dd, 1H, J = 17.6, 0.8 Hz), 5.21 (dd, 1H, J = 10.8, 0.8 Hz), 4.55 (s, 2H), 4.39 (br s, 1H), 2.51 (s, 3H) | 408.21 |

TABLE 1-continued

| Example | Structure | ¹H NMR (ppm) | MS (ESI) m/z (MH⁺) |
|---|---|---|---|
| 38 | 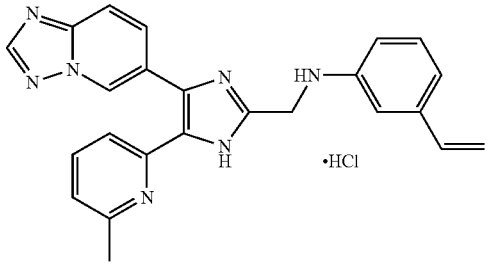 ·HCl | (400 MHz, DMSO-d$_6$) δ 9.49 (dd, 1H, J = 1.6, 0.8 Hz), 8.65 (s, 1H), 7.97 (dd, 1H, J = 9.2, 0.8 Hz), 7.86 (dd, 1H, overlapped, J = 9.2, 1.6 Hz), 7.85 (t, 1H, overlapped, J = 7.8 Hz), 7.65 (d, 1H, J = 8.0 Hz), 7.38 (d, 1H, J = 7.6 Hz), 7.12 (t, 1H, J = 7.8 Hz), 6.91 (t, 1H, J = 1.6 Hz), 6.79 (d, 1H, J = 7.6 Hz), 6.71 (dd, 1H, J = 8.0, 1.6 Hz), 6.64 (dd, 1H, J = 17.6, 11.2 Hz), 5.80 (dd, 1H, J = 17.6, 0.8 Hz), 5.20 (dd, 1H, J = 11.2, 0.8 Hz), 4.79 (s, 2H), 2.51 (s, 3H) | |
| 39 | 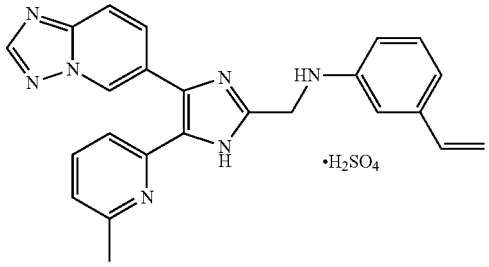 ·H$_2$SO$_4$ | (400 MHz, DMSO-d$_6$) δ 9.40 (dd, 1H, J = 1.6, 0.8 Hz), 8.63 (s, 1H), 7.98 (dd, 1H, J = 9.2, 0.8 Hz), 7.84 (t, 1H, J = 8.0 Hz), 7.76 (dd, 1H, J = 9.2, 1.6 Hz), 7.43 (d, 1H, J = 7.6 Hz), 7.40 (d, 1H, J = 8.0 Hz), 7.13 (t, 1H, J = 7.8 Hz), 6.80 (br s, 1H), 6.79 (d, 1H, overlapped, J = 7.6 Hz), 6.64 (dd, 1H, overlapped, J = 17.6, 11.2 Hz), 6.63 (dd, 1H, overlapped, J = 7.6, 2.0 Hz), 5.74 (dd, 1H, J = 17.6, 0.8 Hz), 5.21 (dd, 1H, J = 11.2, 0.8 Hz), 4.68 (s, 2H), 2.58 (s, 3H) | |
| 40 | 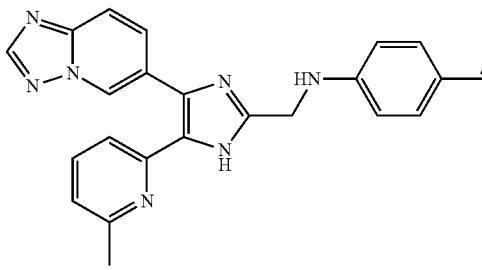 | (400 MHz, CDCl$_3$) δ 10.39 (br s, 1H), 8.96 (s, 1H), 8.37 (s, 1H), 7.82 (dd, 1H, J = 9.2, 1.6 Hz), 7.78 (dd, 1H, J = 9.2, 0.8 Hz), 7.45 (t, 1H, J = 7.6 Hz), 7.28 (m, 2H), 7.22 (br d, 1H, J = 7.6 Hz), 7.01 (d, 1H, J = 7.6 Hz), 6.69 (m, 2H), 6.61 (dd, 1H, J = 17.6, 10.8 Hz), 5.55 (dd, 1H, J = 17.6, 0.8 Hz), 5.05 (dd, 1H, J = 10.8, 0.8 Hz), 4.56, (s, 2H), 2.53 (s, 3H) | 408.21 |
| 41 | 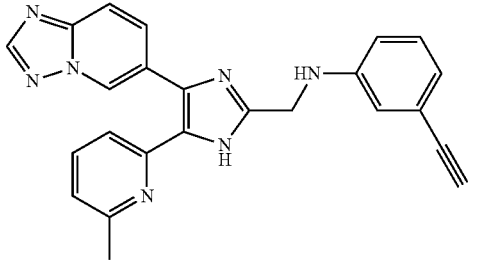 | (400 MHz, CDCl$_3$) δ 8.94 (t, 1H, J = 1.2 Hz), 8.35 (s, 1H), 7.77 (dd, 1H, J = 9.2, 1.2 Hz), 7.72 (d, 1H, J = 9.2 Hz), 7.46 (t, 1H, J = 7.8 Hz), 7.23 (d, 1H, J = 8.0 Hz), 7.07 (t, 1H, J = 7.8 Hz), 6.99 (d, 1H, J = 7.6 Hz), 6.86 (d, 1H, J = 7.6 Hz), 6.73 (br s, 1H), 6.61 (br d, 1H, J = 8.0 Hz), 4.45 (s, 2H), 2.98 (s, 1H), 2.42 (s, 3H) | 406.18 |
| 42 | 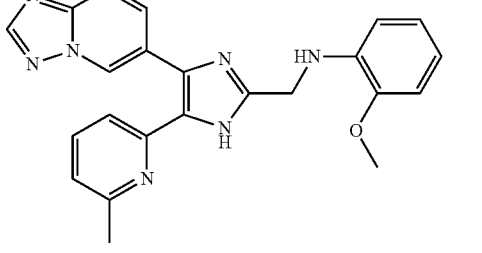 | (400 MHz, CDCl$_3$) δ 8.98 (br s, 1H), 8.37 (s, 1H), 7.83 (dd, 1H, J = 9.2, 1.6 Hz), 7.78 (dd, 1H, J = 9.2, 0.8 Hz), 7.45 (t, 1H, J = 7.6 Hz), 7.22 (br d, 1H, J = 7.6 Hz), 7.00 (d, 1H, J = 7.6 Hz), 6.87 (td, 1H, J = 7.6, 1.6 Hz), 6.84 (dd, 1H, J = 8.0, 1.6 Hz), 6.77 (td, 1H, J = 7.8, 1.6 Hz), 6.69 (dd, 1H, J = 7.8, 1.6 Hz), 4.58 (s, 2H), 3.91 (s, 3H), 2.53 (s, 3H) | 412.21 |

TABLE 1-continued

| Example | Structure | ¹H NMR (ppm) | MS (ESI) m/z (MH⁺) |
|---|---|---|---|
| 43 | 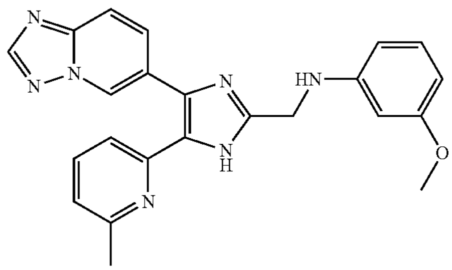 | (400 MHz, CDCl₃) δ 8.95 (br s, 1H), 8.37 (s, 1H), 7.81 (dd, 1H, J = 9.2, 1.6 Hz), 7.76 (dd, 1H, J = 9.2, 0.8 Hz), 7.45 (t, 1H, J = 7.6 Hz), 7.22 (d, 1H, J = 7.6 Hz), 7.11 (t, 1H, J = 8.0 Hz), 7.01 (d, 1H, J = 7.6 Hz), 6.36-6.31 (m, 2H), 6.27 (t, 1H, J = 2.4 Hz), 4.52 (s, 2H), 3.75 (s, 3H), 2.51 (s, 3H) | 412.21 |
| 44 | 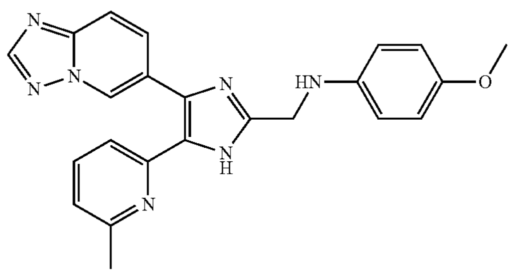 | (400 MHz, CDCl₃) δ 8.96 (br s, 1H), 8.37 (s, 1H), 7.82 (dd, 1H, J = 9.2, 1.6 Hz), 7.77 (dd, 1H, J = 9.2, 0.8 Hz), 7.45 (t, 1H, J = 7.8 Hz), 7.22 (br d, 1H, J = 7.6 Hz), 7.01 (br d, 1H, J = 8.0 Hz), 6.80 (m, 2H), 6.70 (m, 2H), 4.50 (s, 2H), 3.74 (s, 3H), 2.53 (s, 3H) | 412.21 |
| 45 | 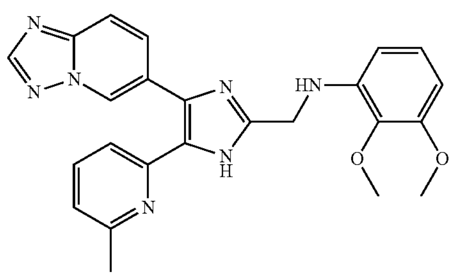 | (400 MHz, CDCl₃) δ 8.96 (br s, 1H), 8.34 (s, 1H), 7.80 (dd, 1H, J = 9.2, 1.6 Hz), 7.72 (d, 1H, J = 9.2 Hz), 7.42 (t, 1H, J = 7.6 Hz), 7.20 (br d, 1H, J = 7.6 Hz), 6.96 (d, 1H, J = 7.6 Hz), 6.88 (td, 1H, J = 8.2, 0.4 Hz), 6.36 (d, 1H, overlapped, J = 8.0 Hz), 6.34 (d, 1H, overlapped, J = 8.2 Hz), 4.52 (s, 2H), 3.84 (s, 3H), 3.81 (s, 3H), 2.43 (s, 3H) | 442.22 |
| 46 | 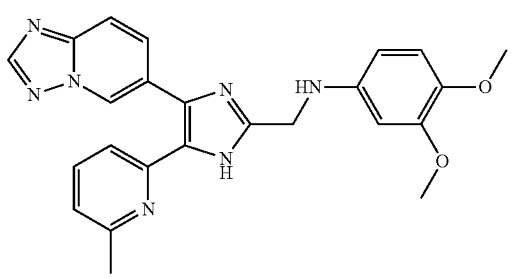 | (400 MHz, CDCl₃) δ 8.94 (dd, 1H, J = 1.6, 0.8 Hz), 8.34 (s, 1H), 7.78 (dd, 1H, J = 9.2, 1.6 Hz), 7.72 (dd, 1H, J = 9.2, 0.8 Hz), 7.44 (t, 1H, J = 8.0 Hz), 7.21 (br d, 1H, J = 8.0 Hz), 6.99 (d, 1H, J = 8.0 Hz), 6.71 (d, 1H, J = 8.4 Hz), 6.30 (d, 1H, J = 2.4 Hz), 6.19 (dd, 1H, J = 8.4, 2.4 Hz), 4.46 (s, 2H), 3.78 (s, 3H), 3.76 (s, 3H), 2.47 (s, 3H) | 442.22 |
| 47 | 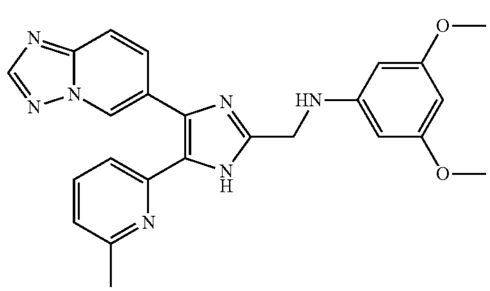 | (400 MHz, CDCl₃) δ 10.43 (br s, 1H), 8.94 (s, 1H), 8.37 (s, 1H), 7.81 (d, 1H, J = 9.2 Hz), 7.77 (d, 1H, J = 9.2 Hz), 7.45 (t, 1H, J = 7.6 Hz), 7.20 (d, 1H, J = 7.6 Hz), 7.01 (d, 1H, J = 7.6 Hz), 5.96 (t, 1H, J = 2.0 Hz), 5.92 (d, 2H, J = 2.0 Hz), 4.52 (d, 2H, J = 2.8 Hz), 4.41 (br s, 1H), 3.75 (s, 6H), 2.54 (s, 3H) | 442.22 |

TABLE 1-continued

| Example | Structure | ¹H NMR (ppm) | MS (ESI) m/z (MH⁺) |
|---|---|---|---|
| 48 | 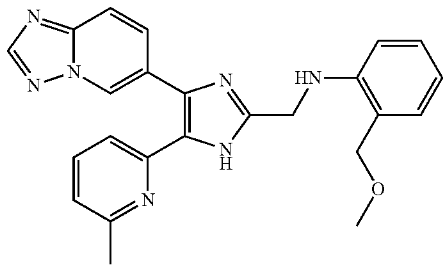 | (400 MHz, CDCl₃) δ 8.97 (br s, 1H), 8.37 (s, 1H), 7.83 (dd, 1H, J = 9.2, 1.6 Hz), 7.77 (dd, 1H, J = 9.2, 0.8 Hz), 7.45 (t, 1H, J = 7.6 Hz), 7.23 (td, 1H, overlapped, J = 7.6, 1.6 Hz), 7.22 (br d, 1H, overlapped, J = 7.6 Hz) 7.12 (dd, 1H, J = 7.6, 1.6 Hz), 7.01 (d, 1H, J = 8.0 Hz), 6.77-6.73 (m, 2H), 4.63 (s, 2H), 4.60 (s, 2H), 3.42 (s, 3H), 2.53 (s, 3H) | 426.22 |
| 49 | 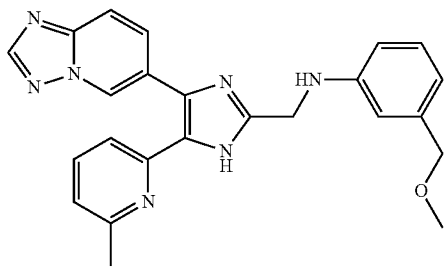 | (400 MHz, CDCl₃) δ 8.96 (br s, 1H), 8.37 (s, 1H), 7.82 (dd, 1H, J = 9.2, 1.6 Hz), 7.78 (dd, 1H, J = 9.2, 0.8 Hz), 7.45 (t, 1H, J = 7.6 Hz), 7.21 (t, 1H, overlapped, J = 8.0 Hz), 7.20 (br d, 1H, overlapped, J = 7.6 Hz), 7.01 (d, 1H, J = 7.6 Hz), 6.76 (d, 1H, overlapped, J = 8.0 Hz), 6.75 (d, 1H, overlapped, J = 1.6 Hz), 6.67-6.64 (m, 1H), 4.56 (s, 2H), 4.40 (s, 2H), 3.38 (s, 3H), 2.54 (s, 3H) | 426.22 |
| 50 | 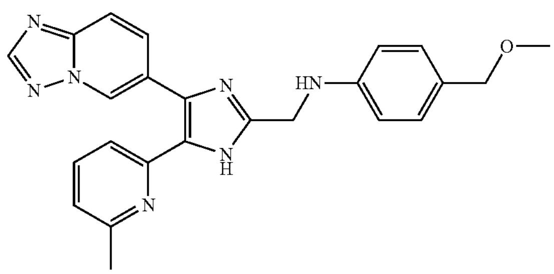 | (400 MHz, CDCl₃) δ 10.36 (br s, 1H), 8.95 (s, 1H), 8.37 (s, 1H), 7.82 (br d, 1H, J = 9.2 Hz), 7.78 (br d, 1H, J = 9.2 Hz), 7.45 (t, 1H, J = 7.6 Hz), 7.20 (br d, 1H, overlapped, J = 7.6 Hz), 7.19 (d, 2H, overlapped, J = 8.4 Hz), 7.01 (d, 1H, J = 7.6 Hz), 6.71 (d, 2H, J = 8.4 Hz), 4.55 (s, 2H), 4.40 (br s, 1H), 4.34 (s, 2H), 3.34 (s, 3H), 2.53 (s, 3H) | 426.22 |
| 51 | 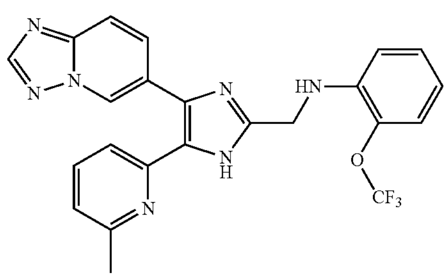 | (400 MHz, CDCl₃) δ 10.42 (br s, 1H), 8.96 (br s,1H), 8.37 (s, 1H), 7.82 (d, 1H, J = 9.2 Hz), 7.78 (d, 1H, J = 9.2 Hz), 7.45 (t, 1H, J = 7.8 Hz), 7.25-7.18 (m, 2H), 7.15 (td, 1H, J = 7.8, 1.2 Hz), 7.01 (d, 1H, J = 7.6 Hz), 6.81 (dd, 1H, J = 8.0, 1.2 Hz), 6.76 (td, 1H, J = 7.8, 1.6 Hz), 4.85 (t, 1H, J = 5.6 Hz), 4.61 (d, 2H, J = 5.6 Hz), 2.52 (s, 3H) | 466.18 |
| 52 | 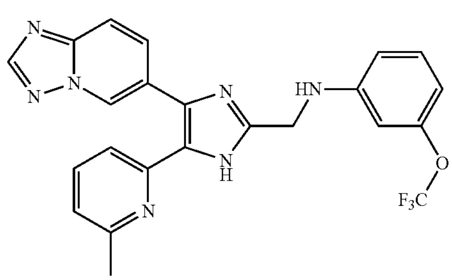 | (400 MHz, CDCl₃) δ 8.94 (br s, 1H), 8.37 (s, 1H), 7.80 (dd, 1H, J = 9.2, 1.6 Hz), 7.77 (dd, 1H, J = 9.2, 0.8 Hz), 7.46 (t, 1H, J = 7.8 Hz), 7.23 (br d, 1H, J = 8.0 Hz), 7.19 (t, 1H, J = 8.2 Hz), 7.02 (d, 1H, J = 7.6 Hz), 6.64-6.60 (m, 2H), 6.55 (br s, 1H), 4.62 (br s, 1H), 4.52 (s, 2H), 2.52 (s, 3H) | 466.18 |

TABLE 1-continued

| Example | Structure | ¹H NMR (ppm) | MS (ESI) m/z (MH⁺) |
|---|---|---|---|
| 53 | 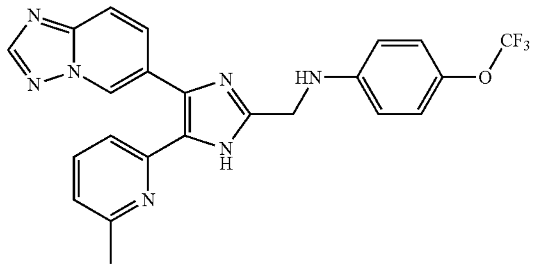 | (400 MHz, CDCl₃) δ 8.95 (s, 1H), 8.38 (s, 1H), 7.81 (dd, 1H, J = 9.2, 1.6 Hz), 7.78 (dd, 1H, J = 9.2, 0.8 Hz), 7.46 (t, 1H, J = 7.8 Hz), 7.23 (d, 1H, J = 8.0 Hz), 7.08 (m, 2H), 7.02 (d, 1H, J = 7.6 Hz), 6.70 (m, 2H), 4.53 (s, 2H), 2.54 (s, 3H) | 466.18 |
| 54 | 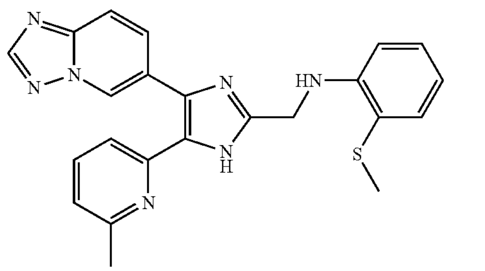 | (400 MHz, CDCl₃) δ 11.34 (br s, 1H), 8.99 (s, 1H), 8.34 (s, 1H), 7.83 (br d, 1H, J = 9.2 Hz), 7.72 (br d, 1H, J = 9.2 Hz), 7.43 (t, 1H, J = 7.8 Hz), 7.35 (dd, 1H, J = 7.6, 1.6 Hz), 7.21 (br d, 1H, J = 7.6 Hz), 7.12 (td, 1H, J = 7.8, 1.6 Hz), 6.95 (d, 1H, J = 8.0 Hz), 6.70 (td, 1H, J = 7.6, 1.2 Hz), 6.65 (dd, 1H, J = 8.0, 1.2 Hz), 5.49 (br t, 1H, J = 4.8 Hz), 4.55 (d, 2H, J = 4.8 Hz), 2.33 (s, 3H), 2.32 (s, 3H) | 428.18 |
| 55 | 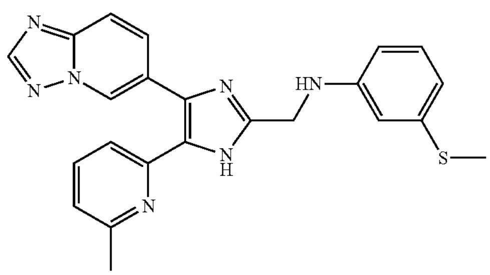 | (400 MHz, CDCl₃) δ 11.06 (br s, 1H), 8.94 (s, 1H), 8.35 (s, 1H), 7.78 (dd, 1H, J = 9.2, 1.2 Hz), 7.74 (d, 1H, J = 9.2 Hz), 7.45 (t, 1H, J = 7.8 Hz), 7.21 (br d, 1H, J = 8.0 Hz), 7.07 (t, 1H, J = 7.8 Hz), 6.99 (d, 1H, J = 7.6 Hz), 6.64 (dd, 1H, J = 7.6, 2.0 Hz), 6.54 (t, 1H, J = 1.6 Hz), 6.42 (dd, 1H, J = 8.0, 1.6 Hz), 4.47 (s, 2H) 4.42 (br s, 1H), 2.45 (s, 3H), 2.40 (s, 3H) | 428.19 |
| 56 | ·HCl | (400 MHz, DMSO-d₆) δ 9.43 (br s, 1H), 8.62 (s, 1H), 7.97 (dd, 1H, J = 9.2, 0.8 Hz), 7.84 (t, 1H, J = 7.6 Hz), 7.80 (dd, 1H, J = 9.2, 1.6 Hz), 7.51 (d, 1H, J = 7.6 Hz), 7.38 (d, 1H, J = 7.6 Hz), 7.08 (t, 1H, J = 7.8 Hz), 6.62 (t, 1H, J = 2.0 Hz), 6.55 (d, 1H, J = 7.6 Hz), 6.51 (dd, 1H, J = 8.0, 2.0 Hz), 4.68 (s, 2H), 2.55 (s, 3H), 2.41 (s, 3H) | |
| 57 | ·H₂SO₄ | (400 MHz, DMSO-d₆) δ 9.40 (dd, 1H, J = 1.6, 0.8 Hz), 8.63 (s, 1H), 7.98 (d, 1H, J = 9.6 Hz), 7.84 (t, 1H, J = 7.6 Hz), 7.77 (dd, 1H, J = 9.6, 1.6 Hz), 7.43 (d, 1H, J = 7.6 Hz), 7.40 (d, 1H, J = 7.6 Hz), 7.08 (t, 1H, J = 8.0 Hz), 6.60 (t, 1H, J = 2.0 Hz), 6.56 (d, 1H, J = 8.0 Hz), 6.48 (dd, 1H, J = 8.0, 2.0 Hz), 4.65 (s, 2H), 2.58 (s, 3H), 2.40 (s, 3H) | |

TABLE 1-continued

| Example | Structure | ¹H NMR (ppm) | MS (ESI) m/z (MH⁺) |
|---|---|---|---|
| 58 | 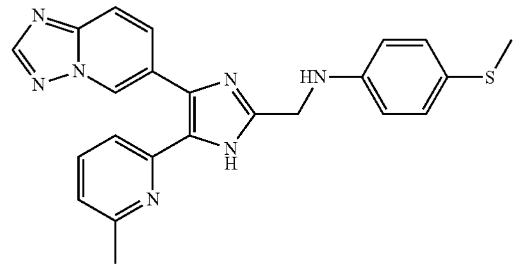 | (400 MHz, CDCl₃) δ 11.08 (br s, 1H), 8.94 (s, 1H), 8.35 (s, 1H), 7.78 (dd, 1H, J = 9.2, 1.6 Hz), 7.73 (d, 1H, J = 9.2 Hz), 7.45 (t, 1H, J = 7.8 Hz), 7.21 (br d, 1H, J = 8.0 Hz), 7.17 (m, 2H), 6.99 (d, 1H, J = 7.6 Hz), 6.60 (m, 2H), 4.46 (s, 2H), 2.45 (s, 3H), 2.37 (s, 3H) | 428.18 |
| 59 | 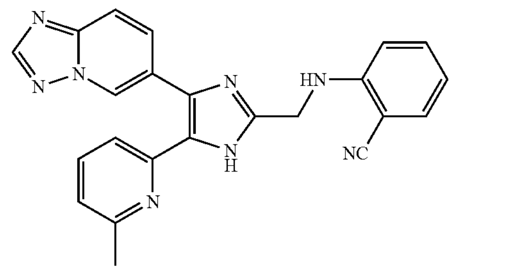 | (400 MHz, CDCl₃) δ 8.98 (br s, 1H), 8.36 (s, 1H), 7.83 (dd, 1H, J = 9.2, 1.6 Hz), 7.76 (dd, 1H, J = 9.2, 0.8 Hz), 7.47 (t, 1H, J = 7.8 Hz), 7.40 (br d, 1H, overlapped, J = 7.6 Hz), 7.38 (t, 1H, J = 7.8 Hz), 7.25 (br d, 1H, J = 8.0 Hz), 7.00 (d, 1H, J = 7.6), 6.80 (d, 1H, J = 8.4 Hz), 6.75 (td, 1H, J = 8.0, 0.8 Hz), 5.32 (br t, 1H, J = 5.6 Hz), 4.62 (d, 2H, J = 5.6 Hz), 2.41 (s, 3H) | 407.19 |
| 60 | 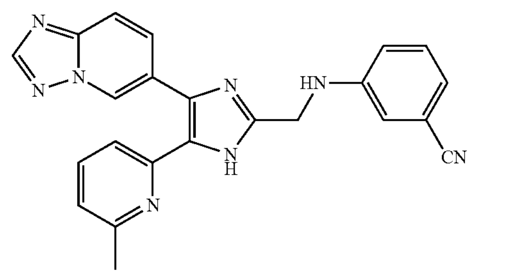 | (400 MHz, CDCl₃) δ 8.94 (t, 1H, J = 1.2 Hz), 8.38 (s, 1H), 7.80 (dd, 1H, J = 9.2, 0.8 Hz), 7.77 (dd, 1H, J = 9.2, 1.6 Hz), 7.55 (t, 1H, J = 8.0 Hz), 7.31 (d, 1H, J = 8.0 Hz), 7.25 (t, 1H, J = 8.0 Hz), 7.08 (d, 1H, J = 8.0 Hz), 7.02 (dt, 1H, J = 7.6, 1.2 Hz), 6.96-6.92 (m, 2H), 4.56 (s, 2H), 2.62 (s, 3H) | 407.19 |
| 61 | 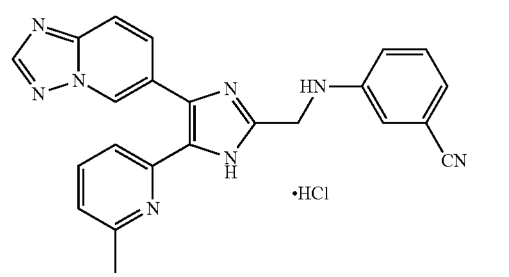 | (400 MHz, DMSO-d₆) δ 9.47 (d, 1H, J = 0.8 Hz), 8.66 (s, 1H), 7.97 (dd, 1H, J = 9.2, 0.8 Hz), 7.87 (t, 1H, overlapped, J = 7.8 Hz), 7.85 (dd, 1H, overlapped, J = 9.2, 1.6 Hz), 7.63 (d, 1H, J = 7.6 Hz), 7.40 (d, 1H, J = 8.0 Hz), 7.33 (t, 1H, J = 7.8 Hz), 7.16 (t, 1H, J = 1.6 Hz), 7.11 (dd, 1H, J = 8.4, 1.6 Hz), 7.06 (br d, 1H, J = 7.6 Hz), 4.79 (s, 2H), 2.53 (s, 3H) | |
| 62 | 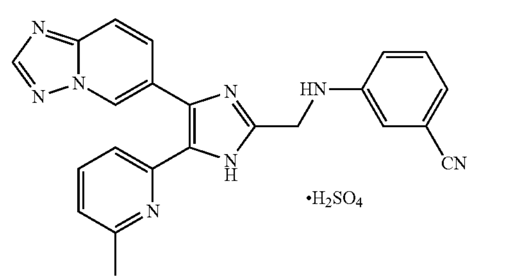 | (400 MHz, DMSO-d₆) δ 9.39 (br s, 1H), 8.64 (s, 1H), 7.99 (d, 1H, J = 9.2 Hz), 7.87 (t, 1H, J = 7.6 Hz), 7.77 (dd, 1H, J = 9.2, 1.6 Hz), 7.45 (d, 1H, overlapped, J = 7.6 Hz), 7.44 (d, 1H, overlapped, J = 7.6 Hz), 7.34 (t, 1H, J = 8.0 Hz), 7.10 (d, 1H, J = 2.0 Hz), 7.07 (d, 1H, overlapped, J = 7.6 Hz), 7.04 (dd, 1H, overlapped, J = 8.0, 2.0 Hz), 4.70 (s, 2H), 2.60 (s, 3H) | |

TABLE 1-continued

| Example | Structure | ¹H NMR (ppm) | MS (ESI) m/z (MH⁺) |
|---|---|---|---|
| 63 | 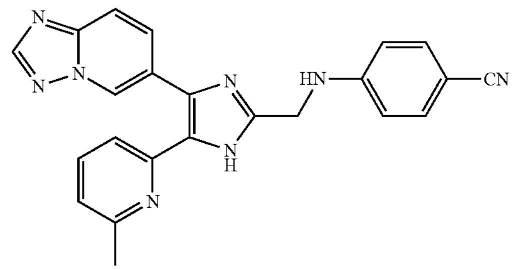 | (400 MHz, CDCl₃) δ 8.93 (t, 1H, J = 1.2 Hz), 8.37 (s, 1H), 7.79 (dd, 1H, overlapped, J = 9.2, 1.6 Hz), 7.76 (dd, 1H, overlapped, J = 9.2, 0.8 Hz), 7.48 (t, 1H, J = 7.8 Hz), 7.43 (m, 2H), 7.24 (d, 1H, J = 8.0 Hz), 7.03 (d, 1H, J = 7.6 Hz), 6.68 (m, 2H), 5.12 (br s, 1H), 4.54 (d, 2H, J = 4.0 Hz), 2.51 (s, 3H) | 407.19 |
| 64 | 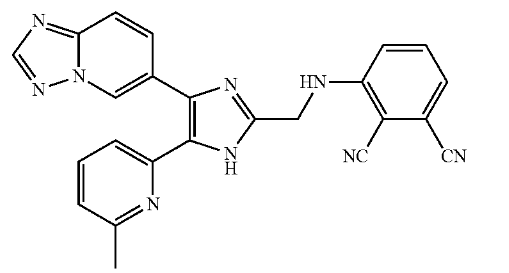 | (400 MHz, CDCl₃) δ 8.99 (br s, 1H), 8.35 (s, 1H), 7.84 (dd, 1H, J = 9.2, 1.6 Hz), 7.74 (dd, 1H, J = 9.2, 0.8 Hz), 7.50 (t, 1H, J = 7.8 Hz), 7.37 (t, 1H, J = 8.2 Hz), 7.27 (br d, 1H, J = 7.6 Hz), 7.05 (d, 1H, J = 8.8 Hz), 7.01 (d, 1H, overlapped, J = 8.0 Hz), 6.98 (d, 1H, overlapped, J = 7.6 Hz), 5.94 (br t, 1H, J = 5.6 Hz), 4.66 (d, 2H, J = 5.6 Hz), 2.30 (s, 3H) | 432.19 |
| 65 | 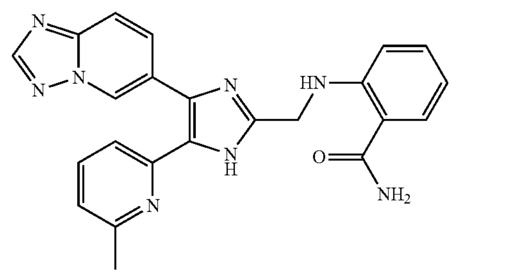 | (400 MHz, CDCl₃) δ 9.04 (dd, 1H, J = 1.6, 0.8 Hz), 8.48 (br s, 1H), 8.33 (s, 1H), 7.84 (dd, 1H, J = 9.2, 1.6 Hz), 7.72 (d, 1H, J = 9.2 Hz), 7.41 (t, 1H, J = 7.8 Hz), 7.37 (dd, 1H, J = 7.6, 1.2 Hz), 7.29 (td, 1H, J = 8.4, 1.2 Hz), 7.21 (br d, 1H, J = 8.0 Hz), 6.92 (d, 1H, J = 7.6 Hz), 6.83 (d, 1H, J = 8.4 Hz), 6.62 (td, 1H, J = 8.0, 1.0 Hz), 6.25 (br s, 2H), 4.59 (d, 2H, J = 5.2 Hz), 2.32 (s, 3H) | 425.20 |
| 66 | 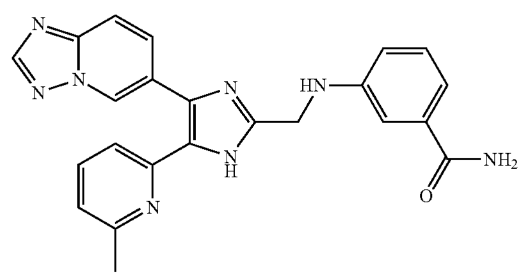 | (400 MHz, CD₃OD) δ 9.06 (br s, 1H), 8.34 (s, 1H), 7.83 (br d, 1H, J = 9.2 Hz), 7.71 (d, 1H, J = 9.2 Hz), 7.59-7.55 (m, 2H), 7.22-7.18 (m, 2H), 7.15 (dt, 1H, J = 7.6, 2.0 Hz), 7.10 (dd, 1H, J = 8.4, 0.8 Hz), 6.86 (ddd, 1H, J = 7.6, 2.0, 0.8 Hz), 4.51 (s, 2H), 2.50 (s, 3H) | 425.20 |
| 67 | 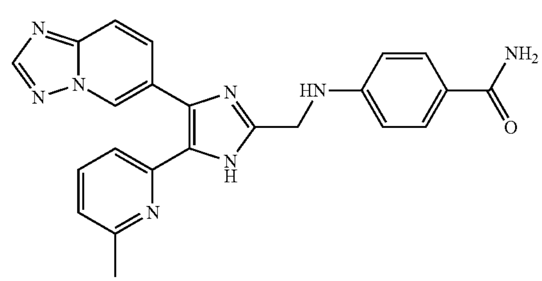 | (400 MHz, CDCl₃/CD₃OD) δ 9.03 (br s, 1H), 8.32 (s, 1H), 7.81 (dd, 1H, J = 9.2, 1.6 Hz), 7.70 (dd, 1H, J = 9.2, 0.8 Hz), 7.67 (m, 2H), 7.55 (t, 1H, J = 7.6 Hz), 7.26 (br d, 1H, J = 7.6 Hz), 7.09 (d, 1H, J = 7.6 Hz), 6.71 (m, 2H), 4.52 (s, 2H), 2.51 (s, 3H) | 425.20 |

TABLE 1-continued

| Example | Structure | $^1$H NMR (ppm) | MS (ESI) m/z (MH$^+$) |
|---|---|---|---|
| 68 | 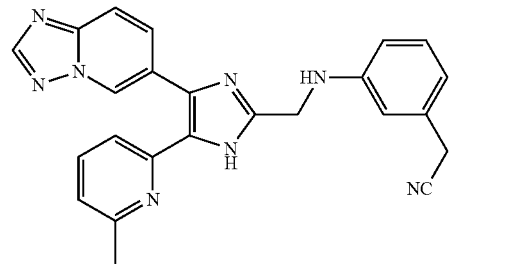 | (400 MHz, CDCl$_3$) δ 10.76 (br s, 1H), 8.94 (br s, 1H), 8.37 (s, 1H), 7.81 (br d, 1H, J = 9.2 Hz), 7.76 (br d, 1H, J = 9.2 Hz), 7.46 (t, 1H, J = 7.6 Hz), 7.21 (br d, 1H, J = 7.6 Hz), 7.20-7.15 (m, 1H), 7.01 (d, 1H, J = 7.6 Hz), 6.69 (dd, 1H, J = 7.6, 0.8 Hz), 6.62-6.40 (m, 2H), 4.53 (br s, 1H, overlapped), 4.52 (br s, 2H, overlapped), 3.65 (s, 2H), 2.50 (s, 3H) | 421.21 |
| 69 | 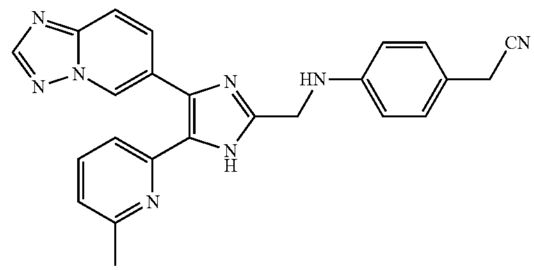 | (400 MHz, CDCl$_3$) δ 10.78 (br s, 1H), 8.94 (br s, 1H), 8.36 (s, 1H), 7.80 (dd, 1H, J = 9.2, 1.2 Hz), 7.76 (d, 1H, J = 9.2 Hz), 7.46 (t, 1H, J = 7.8 Hz), 7.22 (br d, 1H, J = 7.6 Hz), 7.11 (d, 2H, J = 8.4 Hz), 7.01 (d, 1H, J = 8.0 Hz), 6.67 (d, 2H, J = 8.4 Hz), 4.50 (br s, 3H), 3.61 (s, 2H), 2.49 (s, 3H) | 421.21 |
| 70 | 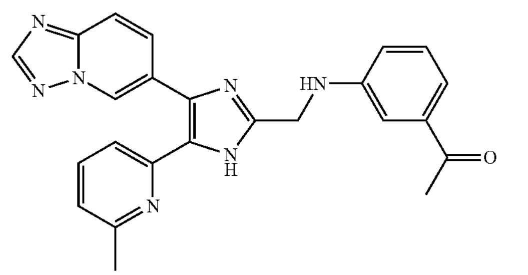 | (400 MHz, CDCl$_3$) δ 11.09 (br s, 1H), 8.92 (s, 1H), 8.35 (s, 1H), 7.79 (d, 1H, J = 9.2 Hz), 7.74 (d, 1H, J = 9.2 Hz), 7.44 (t, 1H, J = 7.8 Hz), 7.30 (d, 1H, J = 7.6 Hz), 7.26-7.24 (m, 1H), 7.23 (t, 1H, overlapped, J = 7.8 Hz), 7.19 (br d, 1H, J = 8.0 Hz), 7.00 (d, 1H, J = 8.0 Hz), 6.86 (dd, 1H, J = 8.0, 1.8 Hz), 4.68 (br s, 1H), 4.52 (d, 2H, J = 5.2 Hz), 2.53 (s, 3H), 2.47 (s, 3H) | 424.21 |
| 71 | 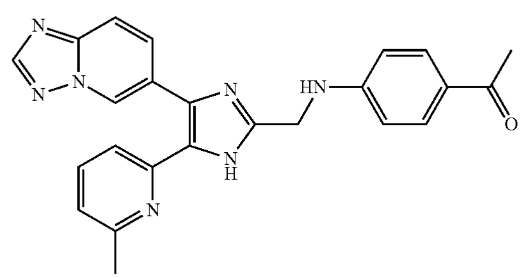 | (400 MHz, CDCl$_3$) δ 8.96 (t, 1H, J = 1.4 Hz), 8.37 (s, 1H), 7.81 (d, 2H, J = 8.8 Hz), 7.79-7.76 (m, 2H), 7.54 (t, 1H, J = 7.8 Hz), 7.30 (d, 1H, J = 8.0 Hz), 7.07 (d, 1H, J = 7.6 Hz), 6.70 (d, 2H, J = 8.8 Hz), 4.63 (s, 2H), 2.59 (s, 3H), 2.48 (s, 3H) | 424.21 |
| 72 | 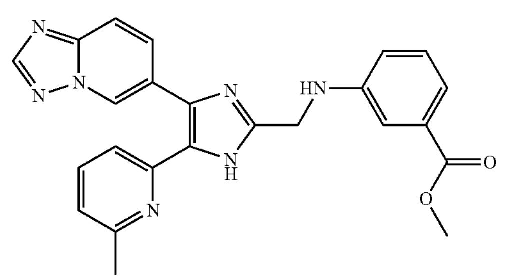 | (400 MHz, CDCl$_3$) δ 8.94 (br s, 1H), 8.34 (s, 1H), 7.77 (dd, 1H, J = 9.2, 1.6 Hz), 7.72 (dd, 1H, J = 9.2, 0.8 Hz), 7.44 (t, 1H, J = 7.8 Hz), 7.39 (dt, 1H, J = 7.6, 1.2 Hz), 7.32 (dd, 1H, J = 2.4, 1.6 Hz), 7.22 (d, 1H, overlapped, J = 8.0 Hz), 7.19 (t, 1H, overlapped, J = 8.0 Hz), 6.98 (d, 1H, J = 7.6 Hz), 6.81 (ddd, 1H, J = 8.0, 2.4, 0.8 Hz), 4.49 (s, 2H), 3.84 (s, 3H), 2.43 (s, 3H) | 440.20 |

TABLE 1-continued

| Example | Structure | ¹H NMR (ppm) | MS (ESI) m/z (MH⁺) |
|---|---|---|---|
| 73 | 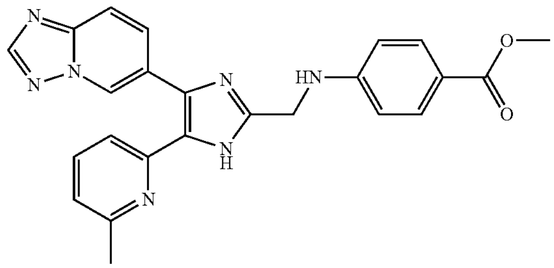 | (400 MHz, CDCl₃) δ 10.52 (br s, 1H), 8.94 (s, 1H), 8.37 (s, 1H), 7.89 (m, 2H), 7.81 (br d, 1H, J = 9.6 Hz), 7.78 (br d, 1H, J = 9.6 Hz), 7.46 (t, 1H, J = 8.0 Hz), 7.21 (d, 1H, J = 8.0 Hz), 7.02 (d, 1H, J = 8.0 Hz), 6.68 (m, 2H), 4.90 (t, 1H, J = 5.6 Hz), 4.58 (d, 2H, J = 5.6 Hz), 3.85 (s, 3H), 2.51 (s, 3H)H, | 440.20 |
| 74 | 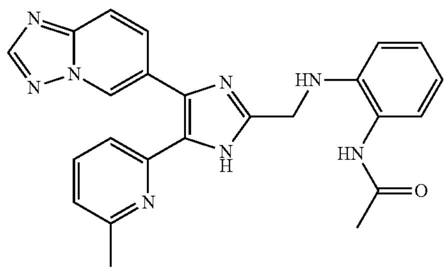 | (400 MHz, DMSO-d₆) δ 12.56 (br s, 1H), 9.58 (s, 1H), 9.36 (s, 1H), 8.50 (s, 1H), 8.00 (br d, 1H, J = 9.2 Hz), 7.82 (d, 1H, J = 9.2 Hz), 7.71 (t, 1H, J = 7.8 Hz), 7.44 (br s, 1H), 7.16 (d, 1H, overlapped, J = 8.0 Hz), 7.15 (d, 1H, overlapped, J = 7.6 Hz), 7.03 (td, 1H, J = 7.6, 1.2 Hz), 6.81 (d, 1H, J = 7.6 Hz), 6.61 (td, 1H, J = 7.6, 1.2 Hz), 5.65 (t, 1H, J = 6.0 Hz), 4.45 (d, 2H, J = 6.0 Hz), 2.47 (br s, 3H), 2.09 (s, 3H) | 439.22 |
| 75 | 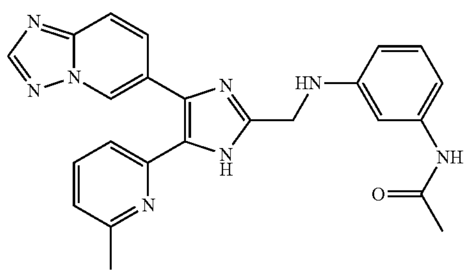 | (400 MHz, DMSO-d₆) δ 8.97 (br s, 1H), 8.35 (s, 1H), 7.79 (dd, 1H, J = 9.2, 1.6 Hz), 7.73 (d, 1H, J = 9.2 Hz), 7.46 (t, 1H, J = 7.8 Hz), 7.38 (br s, 1H), 7.24 (d, 1H, J = 8.0 Hz), 7.15 (br s, 1H), 7.09 (t, 1H, J = 8.0 Hz), 7.01 (d, 1H, J = 7.6 Hz), 6.69 (br d, 1H, J = 8.0 Hz), 6.41 (dd, 1H, J = 8.0, 1.6 Hz), 4.50 (s, 2H), 2.51 (s, 3H), 2.13 (s, 3H) | 439.22 |
| 76 | 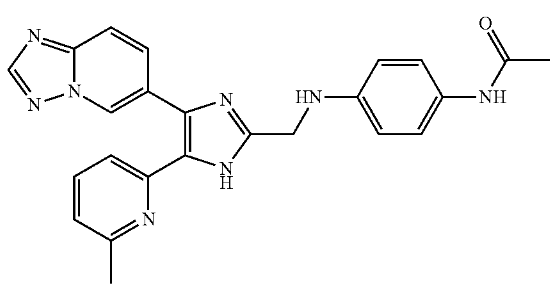 | (400 MHz, DMSO-d₆) δ 8.96 (br s, 1H), 8.37 (s, 1H), 7.81 (dd, 1H, J = 9.2, 1.6 Hz), 7.76 (dd, 1H, J = 9.2, 0.8 Hz), 7.46 (t, 1H, J = 7.8 Hz), 7.27 (m, 2H), 7.23 (d, 1H, J = 8.0 Hz), 7.10 (br s, 1H), 7.01 (d, 1H, J = 7.6 Hz), 6.66 (m, 2H), 4.50 (s, 2H), 2.53 (s, 3H), 2.13 (s, 3H) | 439.22 |
| 77 | 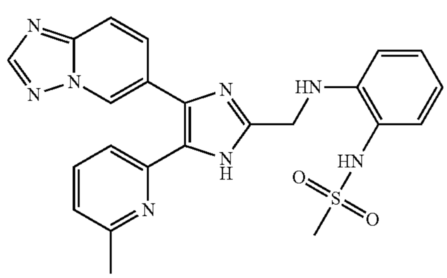 | (400 MHz, CD₃OD) δ 9.18 (dd, 1H, J = 1.6, 0.8 Hz), 8.41 (s, 1H), 7.87 (dd, 1H, J = 9.2, 1.6 Hz), 7.75 (dd, 1H, J = 9.2, 0.8 Hz), 7.66 (t, 1H, J = 7.8 Hz), 7.38 (br d, 1H, J = 7.6 Hz), 7.20 (dd, 1H, J = 7.8, 1.4 Hz), 7.16 (d, 1H, overlapped, J = 7.6 Hz), 7.15 (td, 1H, overlapped, J = 8.0, 1.6 Hz), 6.82 (dd, 1H, J = 8.0, 1.2 Hz), 6.71 (td, 1H, J = 8.0, 1.4 Hz), 4.59 (s, 2H), 3.05 (s, 3H), 2.48 (s, 3H) | 475.19 |

TABLE 1-continued

| Example | Structure | ¹H NMR (ppm) | MS (ESI) m/z (MH⁺) |
|---|---|---|---|
| 78 | 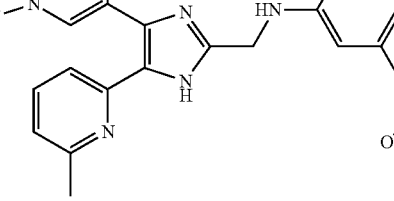 | (400 MHz, CDCl₃) δ 8.92 (br s, 1H), 8.35 (s, 1H), 7.78 (dd, 1H, J = 9.2, 1.6 Hz), 7.73 (dd, 1H, J = 9.2, 0.8 Hz), 7.46 (t, 1H, J = 7.6 Hz), 7.21 (br d, 1H, J = 7.6 Hz), 7.11 (t, 1H, overlapped, J = 8.2 Hz), 7.10 (br s, 1H, overlapped), 7.01 (d, 1H, J = 7.6 Hz), 6.58 (t, 1H, J = 2.0 Hz), 6.54 (ddd, 1H, J = 8.2, 2.0, 0.8 Hz), 6.49 (ddd, 1H, J = 8.2, 2.0, 0.8 Hz), 4.50 (s, 2H), 2.94 (s, 3H), 2.51 (s, 3H) | 475.19 |
| 79 | 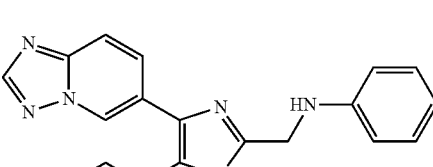 | (400 MHz, CDCl₃) δ 8.93 (br s, 1H), 8.38 (s, 1H), 7.80 (dd, 1H, J = 9.2, 1.6 Hz), 7.76 (d, 1H, J = 9.2 Hz), 7.46 (t, 1H, J = 7.8 Hz), 7.22 (br d, 1H, J = 8.0 Hz), 7.09 (d, 2H, J = 8.8 Hz), 7.02 (d, 1H, J = 7.6 Hz), 6.67 (d, 2H, J = 8.8 Hz), 6.34 (br s, 1H), 4.52 (br s, 3H), 2.93 (s, 3H), 2.54 (s, 3H) | 475.19 |
| 80 | 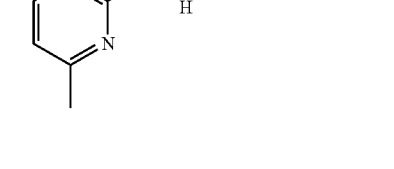 | (400 MHz, CDCl₃) δ 8.99 (s, 1H), 8.36 (s, 1H), 7.83 (dd, 1H, J = 9.2, 1.6 Hz), 7.77 (dd, 1H, J = 9.2, 0.8 Hz), 7.45 (t, 1H, J = 7.8 Hz), 7.23 (br d, 1H, J = 7.6 Hz), 7.10 (dd, 1H, J = 8.0, 1.2 Hz), 7.02 (td, 1H, overlapped, J = 7.6, 1.2 Hz), 7.00 (d, 1H, overlapped, J = 8.0 Hz), 6.78 (td, 1H, J = 7.6, 1.2 Hz), 6.72 (dd, 1H, J = 8.0, 1.2 Hz), 4.58 (s, 2H), 2.73 (s, 6H), 2.50 (s, 3H) | 425.20 |
| 81 | 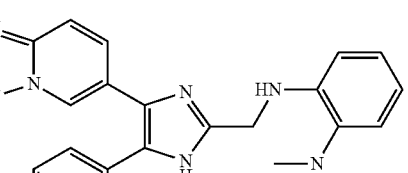 | (400 MHz, DMSO-d₆) δ 9.47 (dd, 1H, J = 1.6, 0.8 Hz), 8.63 (s, 1H), 7.97 (dd, 1H, J = 9.2, 0.8 Hz), 7.87 (t, 1H, J = 7.8 Hz), 7.84 (dd, 1H, J = 9.2, 1.6 Hz), 7.59 (br d, 1H, overlapped, J = 8.0 Hz), 7.58 (d, 1H, J = 7.6 Hz), 7.41 (d, 1H, J = 7.6 Hz), 7.29 (t, 1H, J = 7.4 Hz), 6.99 (dd, 1H, J = 7.6, 0.8 Hz), 6.89 (t, 1H, J = 7.4 Hz), 4.81 (s, 2H), 3.10 (s, 6H), 2.56 (s, 3H) | |
| 82 | 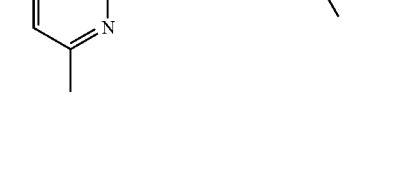 | (400 MHz, CDCl₃) δ 8.97 (s, 1H), 8.36 (s, 1H), 7.80 (dd, 1H, J = 9.2, 1.6 Hz), 7.75 (d, 1H, J = 9.2 Hz), 7.45 (t, 1H, J = 7.8 Hz), 7.23 (d, 1H, J = 8.0 Hz), 7.07 (t, 1H, J = 8.2 Hz), 7.00 (d, 1H, J = 7.6 Hz), 6.24 (d, 1H, J = 8.0 Hz), 6.14 (br s, 2H), 4.55 (s, 2H), 2.90 (s, 6H), 2.52 (s, 3H) | 425.21 |

TABLE 1-continued

| Example | Structure | ¹H NMR (ppm) | MS (ESI) m/z (MH⁺) |
|---|---|---|---|
| 83 | 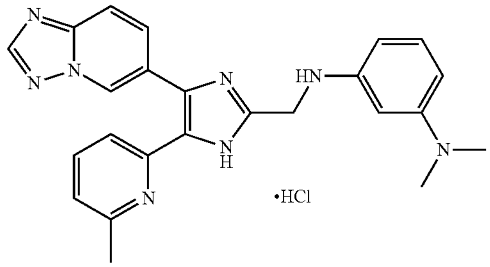 | (400 MHz, DMSO-d₆) δ 9.48 (dd, 1H, J = 1.6, 0.8 Hz), 8.64 (s, 1H), 7.97 (dd, 1H, J = 9.2, 0.8 Hz), 7.86 (t, 1H, overlapped, J = 7.8 Hz), 7.85 (dd, 1H, overlapped, J = 9.2, 1.6 Hz), 7.62 (d, 1H, J = 8.0 Hz), 7.39 (d, 1H, J = 7.6 Hz), 7.28 (t, 1H, J = 8.2 Hz), 7.17 (br s, 1H), 6.98 (br d, 1H, J = 8.0 Hz), 6.81 (br d, 1H, J = 8.4 Hz), 4.78 (s, 2H), 3.09 (s, 6H), 2.52 (s, 3H) | |
| 84 | 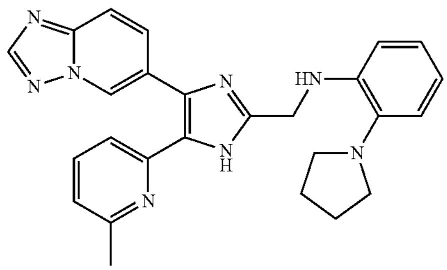 | (400 MHz, CDCl₃) δ 10.41 (br s, 1H), 8.99 (s, 1H), 8.36 (s, 1H), 7.84 (dd, 1H, J = 9.2, 1.2 Hz), 7.76 (d, 1H, J = 9.2 Hz), 7.45 (t, 1H, J = 7.8 Hz), 7.23 (br s, 1H), 7.10 (dd, 1H, J = 7.6, 1.2 Hz), 7.00 (td, 1H, overlapped, J = 7.6, 1.2 Hz), 6.99 (d, 1H, overlapped, J = 7.6 Hz), 6.77 (td, 1H, J = 7.6, 1.2 Hz), 6.72 (d, 1H, J = 8.0 Hz), 4.58 (s, 2H), 3.12 (br s, 4H), 2.51 (s, 3H), 1.98 (br s, 4H) | 451.22 |
| 85 | 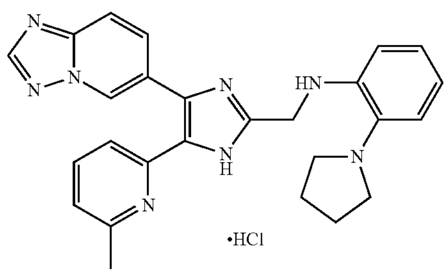 | (400 MHz, DMSO-d₆) δ 9.47 (dd, 1H, J = 2.0, 0.8 Hz), 8.63 (s, 1H), 7.97 (dd, 1H, J = 9.2, 0.8 Hz), 7.87 (t, 1H, J = 7.8 Hz), 7.84 (dd, 1H, J = 9.2, 2.0 Hz), 7.60 (d, 1H, J = 8.0 Hz), 7.57 (d, 1H, J = 8.0 Hz), 7.41 (d, 1H, J = 7.6 Hz), 7.30 (td, 1H, J = 7.8, 0.8 Hz), 7.02 (dd, 1H, J = 7.8, 1.2 Hz), 6.88 (td, 1H, J = 8.0, 1.2 Hz), 4.82 (s, 2H), 3.72 (br s, 4H), 2.55 (s, 3H), 2.17 (m, 4H) | |
| 86 | 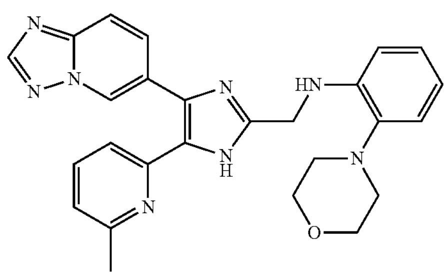 | (400 MHz, CDCl₃) δ 8.96 (s, 1H), 8.37 (s, 1H), 7.82 (dd, 1H, J = 9.2, 1.6 Hz), 7.78 (dd, 1H, J = 9.2, 1.2 Hz), 7.48 (t, 1H, J = 7.6 Hz), 7.25 (br d, 1H, J = 7.6 Hz), 7.09 (dd, 1H, J = 8.0, 1.6 Hz) 7.05 (td, 1H, overlapped, J = 7.6, 1.6 Hz), 7.02 (d, 1H, overlapped, J = 7.6 Hz), 6.80 (td, 1H, J = 7.6, 1.2 Hz), 6.71 (dd, 1H, J = 8.0, 1.2 Hz), 4.57 (s, 2H), 3.90 (br t, 4H, J = 4.6 Hz), 2.96 (br t, 4H, J = 4.6 Hz), 2.54 (s, 3H) | 467.22 |
| 87 | 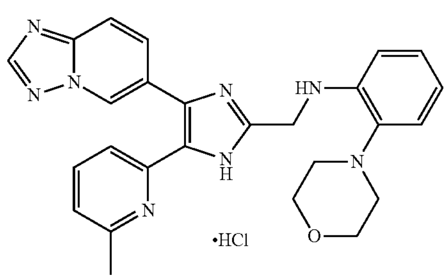 | (400 MHz, DMSO-d₆) δ 9.46 (dd, 1H, J = 1.6, 0.8 Hz), 8.64 (s, 1H), 7.98 (dd, 1H, J = 9.2, 0.8 Hz), 7.84 (t, 1H, J = 7.8 Hz), 7.82 (dd, 1H, J = 9.2, 1.6 Hz), 7.57 (d, 1H, J = 8.0 Hz), 7.38 (d, 1H, J = 7.6 Hz), 7.06 (dd, 1H, J = 7.6, 1.2 Hz), 6.98 (td, 1H, J = 7.8, 1.2 Hz), 6.82 (d, 1H, J = 7.8, 1.2 Hz), 6.70 (td, 1H, J = 7.6, 1.2 Hz), 4.80 (s, 2H), 3.84 (br t, 4H, J = 4.4 Hz), 2.89 (br t, 4H, J = 4.4 Hz), 2.53 (s, 3H) | |

TABLE 1-continued

| Example | Structure | $^1$H NMR (ppm) | MS (ESI) m/z (MH$^+$) |
|---|---|---|---|
| 88 | 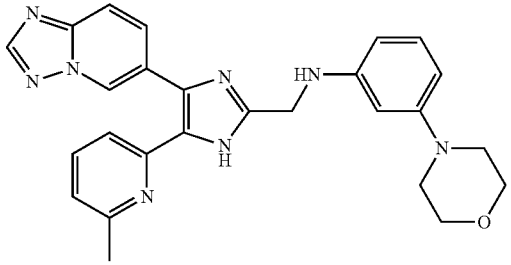 | (400 MHz, CDCl$_3$) δ 8.96 (t, 1H, J = 1.2 Hz), 8.37 (s, 1H), 7.82-7.76 (m, 2H), 7.48 (t, 1H, J = 7.6 Hz), 7.24 (br d, 1H, J = 7.6 Hz), 7.12 (t, 1H, J = 8.0 Hz), 7.03 (d, 1H, J = 7.6 Hz), 6.39 (dd, 1H, J = 8.0, 1.6 Hz), 6.34 (t, 1H, J = 2.0 Hz), 6.29 (dd, 1H, J = 8.0, 2.0 Hz), 4.56 (s, 2H), 3.85-3.82 (m, 4H), 3.15-3.12 (m, 4H), 2.56 (s, 3H) | 467.23 |
| 89 | 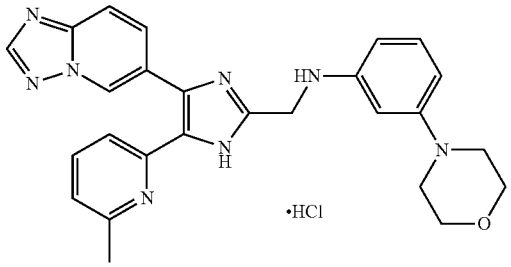 | (400 MHz, DMSO-d$_6$) δ 9.47 (dd, 1H, J = 1.6, 0.8 Hz), 8.64 (s, 1H), 7.97 (dd, 1H, J = 9.2, 0.8 Hz), 7.85 (t, 1H, J = 8.0 Hz), 7.84 (dd, 1H, J = 9.2, 1.6 Hz), 7.60 (d, 1H, J = 8.0 Hz), 7.39 (d, 1H, J = 8.0 Hz), 7.17 (t, 1H, J = 8.0 Hz), 6.86 (br s, 1H), 6.76 (br s, 1H), 6.59 (br d, 1H, J = 7.6 Hz), 4.76 (s, 2H), 3.92 (br s, 4H), 3.34 (br s, 4H), 2.52 (s, 3H) | |
| 90 | 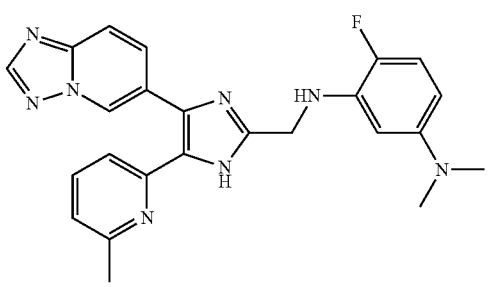 | (400 MHz, CDCl$_3$) δ 8.95 (t, 1H, J = 1.2 Hz), 8.35 (s, 1H), 7.78 (dd, 1H, J = 9.2, 1.6 Hz), 7.70 (dd, 1H, J = 9.2, 1.2 Hz), 7.43 (t, 1H, J = 7.8 Hz), 7.21 (d, 1H, J = 8.0 Hz), 6.94 (d, 1H, J = 7.6 Hz), 6.80-6.73 (m, 1H), 6.14 (br d, 1H, J = 7.6 Hz), 6.00-5.95 (m, 1H), 4.49 (s, 2H), 2.79 (s, 6H), 2.31 (s, 3H) | 443.21 |
| 91 | 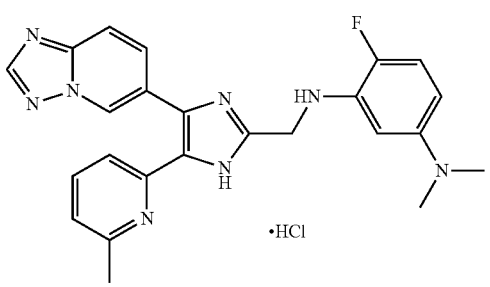 | (400 MHz, DMSO-d$_6$) δ 9.49 (dd, 1H, J = 1.6, 0.8 Hz), 8.63 (s, 1H), 7.97 (dd, 1H, J = 9.2, 0.8 Hz), 7.85 (dd, 1H, overlapped, J = 9.2, 1.6 Hz), 7.84 (t, 1H, overlapped, J = 8.0 Hz), 7.60 (d, 1H, J = 8.0 Hz), 7.39 (br s, 1H, overlapped), 7.38 (d, 1H, overlapped, J = 8.0 Hz), 7.24 (pseudo t, 1H, J = 9.8 Hz), 6.97 (br s, 1H), 4.86 (s, 2H), 3.10 (s, 6H), 2.52 (s, 3H) | |
| 92 | 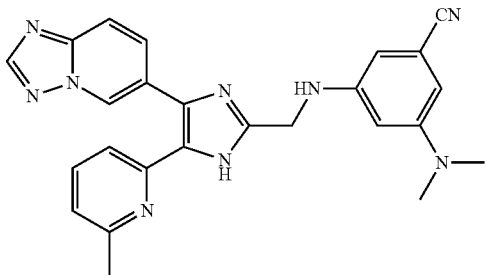 | (400 MHz, CDCl$_3$) δ 8.94 (t, 1H, J = 1.2 Hz), 8.38 (s, 1H), 7.80 (dd, 1H, overlapped, J = 9.2, 1.6 Hz), 7.78 (dd, 1H, overlapped, J = 9.2, 1.2 Hz), 7.49 (t, 1H, J = 7.6 Hz), 7.25 (d, 1H, J = 7.6 Hz), 7.04 (d, 1H, J = 7.6 Hz), 6.38 (dd, 1H, J = 2.4, 1.2 Hz), 6.30 (t, 1H, J = 1.6 Hz), 6.18 (t, 1H, J = 2.2 Hz), 4.53 (s, 2H), 2.92 (s, 6H), 2.56 (s, 3H) | 450.21 |

TABLE 1-continued

| Example | Structure | $^1$H NMR (ppm) | MS (ESI) m/z (MH$^+$) |
|---|---|---|---|
| 93 | 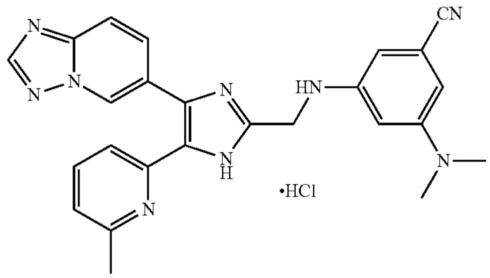 | (400 MHz, DMSO-d$_6$) δ 9.44 (dd, 1H, J = 2.0, 0.8 Hz), 8.63 (s, 1H), 7.97 (dd, 1H, J = 9.2, 0.8 Hz), 7.85 (t, 1H, J = 7.8 Hz), 7.81 (dd, 1H, J = 9.2, 2.0 Hz), 7.55 (d, 1H, J = 8.0 Hz), 7.40 (d, 1H, J = 7.6 Hz), 6.47 (s, 2H), 6.37 (br s, 1H), 4.73 (s, 2H), 2.90 (s, 6H), 2.55 (s, 3H) | |
| 94 | 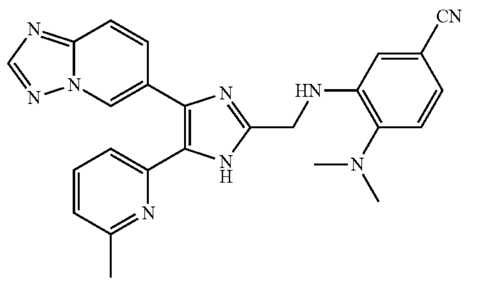 | (400 MHz, CDCl$_3$) δ 8.96 (t, 1H, J = 1.6 Hz), 8.38 (s, 1H), 7.82 (dd, 1H, J = 9.2, 1.6 Hz), 7.79 (dd, 1H, J = 9.2, 0.8 Hz), 7.53 (t, 1H, J = 7.8 Hz), 7.31 (d, 1H, J = 8.0 Hz), 7.08-7.03 (m, 3H), 6.87 (d, 1H, J = 1.6 Hz), 5.44 (br s, 1H), 4.55 (s, 2H), 2.74 (s, 6H), 2.58 (s, 3H) | 450.21 |
| 95 | 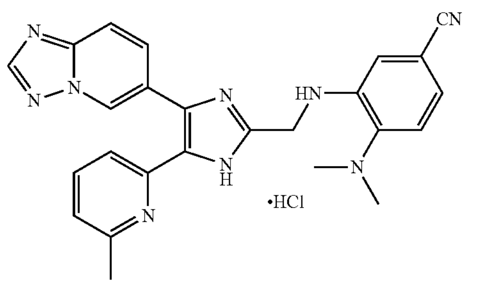 | (400 MHz, DMSO-d$_6$) δ 9.44 (dd, 1H, J = 1.6, 0.8 Hz), 8.64 (s, 1H), 7.99 (dd, 1H, J = 9.2, 0.8 Hz), 7.84 (t, 1H, overlapped, J = 7.8 Hz), 7.82 (dd, 1H, J = 9.2, 0.8 Hz), 7.51 (d, 1H, J = 8.0 Hz), 7.39 (d, 1H, J = 7.6 Hz), 7.15 (dd, 2H, overlapped, J = 7.6, 0.8 Hz), 7.14 (d, 1H, overlapped, J = 1.2 Hz), 4.79 (s, 2H), 2.71 (s, 6H), 2.56 (s, 3H) | |
| 96 | 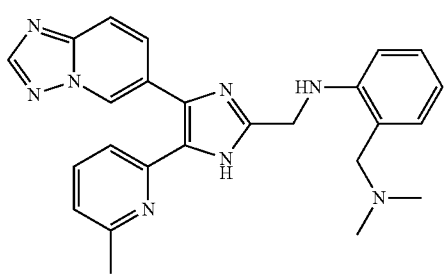 | (400 MHz, CDCl$_3$) δ 10.57 (br s, 1H), 8.97 (s, 1H), 8.34 (s, 1H), 7.82 (dd, 1H, J = 9.2, 1.2 Hz), 7.74 (d, 1H, J = 9.2 Hz), 7.43 (t, 1H, J = 7.8 Hz), 7.21 (br s, 1H, overlapped), 7.17 (td, 1H, J = 8.0, 1.6 Hz), 7.01 (dd, 1H, J = 7.6, 1.6 Hz), 6.98 (d, 1H, J = 7.6 Hz), 6.72-6.66 (m, 2H), 4.61 (s, 2H), 3.54 (s, 2H), 2.51 (s, 3H), 2.28 (s, 6H) | 439.23 |
| 97 | 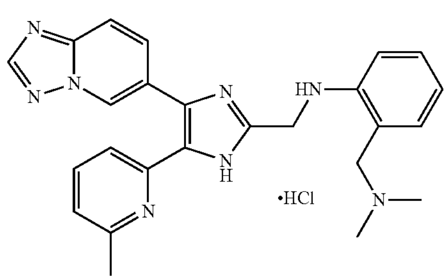 | (400 MHz, DMSO-d$_6$) δ 10.03 (br s, 1H), 9.48 (dd, 1H, J = 1.6, 0.8 Hz), 8.62 (s, 1H), 7.95 (dd, 1H, J = 9.2, 0.8 Hz), 7.87-7.82 (m, 2H), 7.64 (d, 1H, J = 7.6 Hz), 7.38 (d, 1H, J = 7.6 Hz), 7.33-7.27 (m, 2H), 6.95 (br s, 1H), 6.78-6.74 (m, 2H), 4.81 (s, 2H), 4.43 (s, 2H), 2.77 (s, 6H), 2.52 (s, 3H) | |

TABLE 1-continued

| Example | Structure | ¹H NMR (ppm) | MS (ESI) m/z (MH⁺) |
|---|---|---|---|
| 98 | 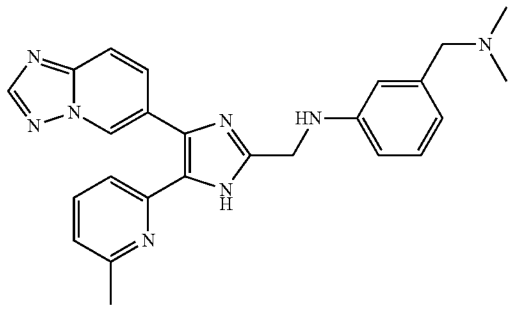 | (400 MHz, CDCl₃) δ 9.02 (br s, 1H), 8.35 (s, 1H), 7.82 (dd, 1H, J = 9.2, 1.6 Hz), 7.74 (dd, 1H, J = 9.2, 0.8 Hz), 7.46 (t, 1H, J = 7.6), 7.27 (br d, 1H, J = 7.6 Hz), 7.13 (t, 1H, J = 7.8), 7.00 (d, 1H, J = 7.6 Hz), 6.90 (br s, 1H), 6.67 (d, 1H, J = 7.6 Hz), 6.61 (dd, 1H, J = 8.0, 2.0 Hz), 4.54 (s, 2H), 3.48 (s, 2H), 2.51 (s, 3H), 2.30 (s, 6H) | 439.23 |
| 99 | ·HCl | (400 MHz, DMSO-d₆) δ 10.69 (br s, 1H), 9.48 (dd, 1H, J = 1.6, 0.8 Hz), 8.63 (s, 1H), 7.96 (dd, 1H, J = 9.2, 0.8 Hz), 7.84 (t, 1H, J = 8.0 Hz), 7.83 (dd, 1H, J = 9.2, 1.6 Hz), 7.61 (d, 1H, J = 8.0 Hz), 7.37 (d, 1H, J = 8.0 Hz), 7.21 (t, 1H, J = 8.2 Hz), 7.09 (br s, 1H), 6.85 (dd, 1H, overlapped, J = 8.4, 2.2 Hz), 6.82 (d, 1H, J = 8.0 Hz), 4.76 (s, 2H), 4.16 (d, 1H, J = 4.8 Hz), 2.66 (d, 6H, J = 4.4 Hz), 2.51 (s, 3H) | |
| 100 | 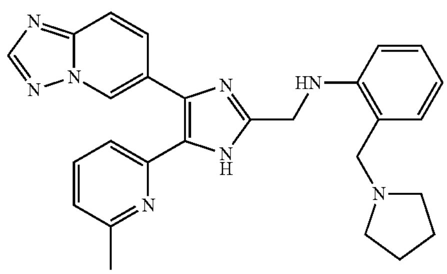 | (400 MHz, CDCl₃) δ 10.40 (br s, 1H), 8.98 (s, 1H), 8.35 (s, 1H), 7.83 (d, 1H, J = 9.2 Hz), 7.75 (d, 1H, J = 9.2 Hz), 7.43 (t, 1H, J = 7.6 Hz), 7.20 (br s, 1H, overlapped), 7.15 (td, 1H, J = 8.0, 1.6 Hz), 7.04 (d, 1H, J = 8.0 Hz), 6.98 (d, 1H, J = 7.6 Hz), 6.69 (pseudo t, 2H, J = 7.2 Hz), 4.58 (s, 2H), 3.72 (s, 2H), 2.56 (br s, 4H), 2.50 (s, 3H), 1.80 (br s, 4H) | 465.25 |
| 101 | ·HCl | (400 MHz, DMSO-d₆) δ 10.29 (br s, 1H), 9.47 (t, 1H, J = 0.8 Hz), 8.62 (s, 1H), 7.95 (d, 1H, J = 9.2 Hz), 7.87-7.83 (m, 2H), 7.65 (d, 1H, J = 8.0 Hz), 7.38 (br d, 2H, J = 7.6 Hz), 7.27 (td, 1H, J = 8.0, 1.2 Hz), 6.75 (t, 1H, overlapped, J = 7.6 Hz), 6.72 (d, 1H, overlapped, J = 7.6 Hz), 4.82 (s, 2H), 4.47 (s, 2H), 3.44 (br s, 2H), 3.17 (br s, 2H), 2.52 (s, 3H), 2.04 (br s, 2H), 1.94 (br s, 2H) | |
| 102 | 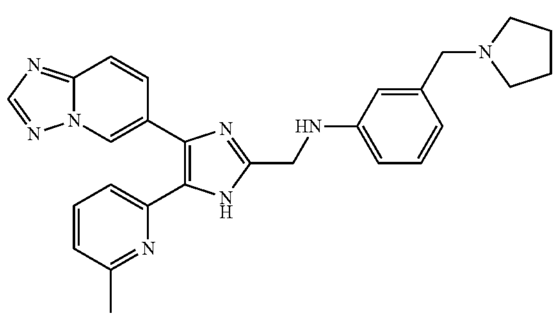 | (400 MHz, CDCl₃) δ 9.04 (s, 1H), 8.35 (s, 1H), 7.83 (dd, 1H, J = 9.2, 1.6 Hz), 7.73 (d, 1H, J = 9.2 Hz), 7.47 (t, 1H, J = 7.8 Hz), 7.28 (br d, 1H, J = 7.6 Hz), 7.11 (t, 1H, J = 7.8 Hz), 7.00 (d, 1H, J = 8.0 Hz), 6.95 (br s, 1H), 6.68 (d, 1H, J = 7.6 Hz), 6.60 (dd, 1H, J = 8.0, 2.0 Hz), 4.54 (s, 2H), 3.65 (s, 2H), 2.61 (br s, 4H), 2.51 (s, 3H), 1.78-1.75 (m, 4H) | 465.25 |

TABLE 1-continued

| Example | Structure | ¹H NMR (ppm) | MS (ESI) m/z (MH⁺) |
|---|---|---|---|
| 103 | 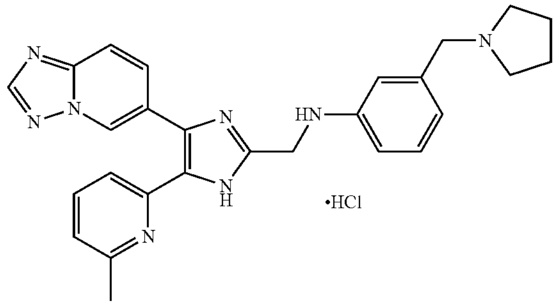 | (400 MHz, DMSO-d₆) δ 10.93 (br s, 1H), 9.48 (dd, 1H, J = 1.2, 1.6 Hz), 8.63 (s, 1H), 7.96 (dd, 1H, J = 9.2, 0.8 Hz), 7.86-7.81 (m, 2H), 7.61 (d, 1H, J = 8.0 Hz), 7.37 (d, 1H, J = 7.6 Hz), 7.19 (t, 1H, J = 7.8 Hz), 7.15 (br s, 1H), 6.86-6.81 (m, 2H), 4.76 (s, 2H), 4.22 (d, 2H, J = 5.6 Hz), 3.29 (m, 2H), 3.00 (m, 2H), 2.51 (s, 3H), 1.92 (m, 2H), 1.82 (m, 2H) | |
| 104 | 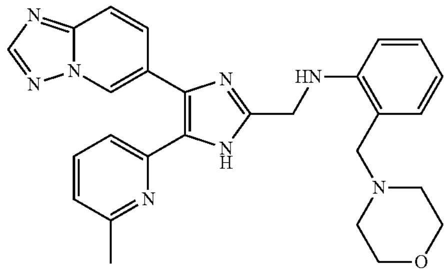 | (400 MHz, CDCl₃) δ 10.35 (br s, 1H), 8.97 (s, 1H), 8.36 (s, 1H), 7.83 (d, 1H, J = 9.2 Hz), 7.76 (d, 1H, J = 9.2 Hz), 7.44 (t, 1H, J = 7.6 Hz), 7.21 (br s, 1H, overlapped), 7.19 (td, 1H, J = 7.6, 1.6 Hz), 7.04 (dd, 1H, J = 7.6, 1.6 Hz), 6.99 (d, 1H, J = 7.6 Hz), 6.73-6.68 (m, 2H), 4.57 (s, 2H), 3.71 (br s, 4H), 3.63 (s, 2H), 2.50 (br s, 7H) | 481.25 |
| 105 | 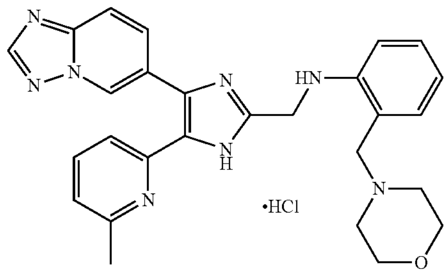 | (400 MHz, DMSO-d₆) δ 9.46 (s, 1H), 8.62 (s, 1H), 7.96 (dd, 1H, J = 9.2, 0.8 Hz), 7.85 (t, 1H, overlapped, J = 8.0 Hz), 7.83 (dd, 1H, overlapped, J = 9.2, 1.6 Hz), 7.60 (d, 1H, J = 8.0 Hz), 7.38 (br d, 2H, J = 8.0 Hz), 7.29 (td, 1H, J = 8.0, 1.2 Hz), 6.75 (t, 1H, overlapped, J = 8.0 Hz), 6.74 (d, 1H, overlapped, J = 8.0 Hz), 4.82 (s, 2H), 4.45 (s, 2H), 3.93 (br s, 4H), 3.34 (br s, 4H), 2.53 (s, 3H) | |
| 106 | 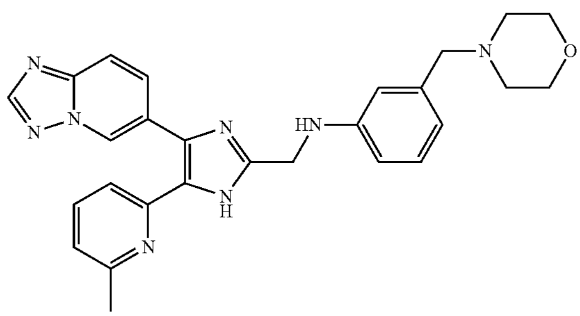 | (400 MHz, CDCl₃) δ 10.78 (br s, 1H), 8.97 (s, 1H), 8.35 (s, 1H), 7.81 (dd, 1H, J = 9.2, 1.6 Hz), 7.74 (d, 1H, J = 9.2 Hz), 7.45 (t, 1H, J = 7.8 Hz), 7.23 (br s, 1H), 7.13 (t, 1H, J = 7.8 Hz), 7.00 (d, 1H, J = 7.6 Hz), 6.79 (br s, 1H), 6.71 (d, 1H, J = 7.6 Hz), 6.59 (dd, 1H, J = 8.0, 1.6 Hz), 4.53 (s, 2H), 4.44 (br s, 1H), 3.66 (m, 4H), 3.45 (s, 2H), 2.49 (s, 3H), 2.44 (br s, 4H) | 481.25 |
| 107 | 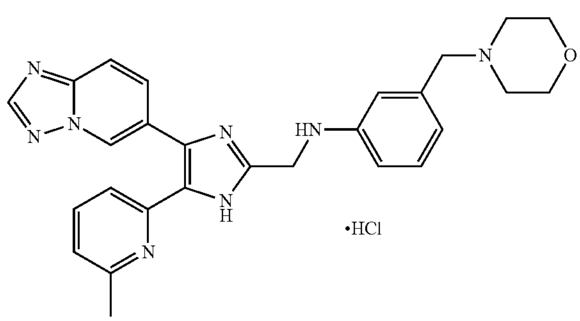 | (400 MHz, DMSO-d₆/D₂O) δ 9.36 (dd, 1H, J = 1.8, 1.0 Hz), 8.62 (s, 1H), 7.95 (dd, 1H, J = 9.4, 1.0 Hz), 7.87 (t, 1H, J = 7.8 Hz), 7.82 (dd, 1H, J = 9.4, 1.8 Hz), 7.48 (d, 1H, J = 8.0 Hz), 7.42 (d, 1H, J = 7.6 Hz), 7.28 (t, 1H, J = 7.8 Hz), 6.90 (br s, 1H), 6.86-6.82 (m, 2H), 4.68 (s, 2H Hz), 4.23 (s, 2H), 3.70 (br s, 4H), 3.22 (br s, 2H), 3.14 (br s, 2H), 2.58 (s, 3H) | |

TABLE 1-continued

| Example | Structure | $^1$H NMR (ppm) | MS (ESI) m/z (MH$^+$) |
|---|---|---|---|
| 108 | 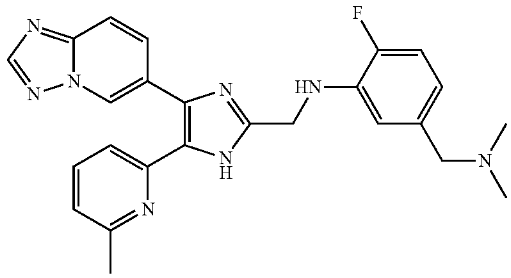 | (400 MHz, CDCl$_3$) δ 9.06 (s, 1H), 8.34 (s, 1H), 7.84 (dd, 1H, J = 9.2, 1.6 Hz), 7.72 (d, 1H, J = 9.2 Hz), 7.48 (t, 1H, J = 7.6 Hz), 7.32 (br s, 1H), 7.18 (br s, 1H), 7.00 (d, 1H, J = 7.6 Hz), 6.90 (dd, 1H, J = 11.2, 8.0 Hz), 6.55-6.51 (m, 1H), 4.78 (br s, 1H), 4.59 (d, 2H, J = 6.4 Hz), 3.54 (s, 2H), 2.50 (s, 3H), 2.34 (s, 6H) | 457.22 |
| 109 | ·HCl | (400 MHz, DMSO-d$_6$) δ 10.73 (br s, 1H), 9.46 (t, 1H, J = 1.2 Hz), 8.62 (s, 1H), 7.96 (dd, 1H, J = 9.2, 0.8 Hz), 7.84 (dd, 1H, overlapped, J = 9.2, 1.6 Hz), 7.82 (t, 1H, overlapped, J = 7.8 Hz), 7.55 (d, 1H, J = 8.0 Hz), 7.37 (dd, 1H, overlapped, J = 8.2, 2.0 Hz), 7.36 (d, 1H, J = 7.6 Hz), 7.18 (dd, 1H, J = 11.8, 8.2 Hz), 6.82-6.78 (m, 1H), 4.79 (s, 2H), 4.17 (br s, 2H), 2.64 (d, 6H, J = 1.6 Hz), 2.52 (s, 3H) | |
| 110 | 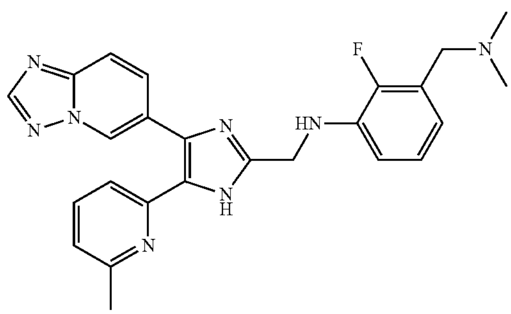 | (400 MHz, CDCl$_3$) δ 8.99 (br s, 1H), 8.36 (s, 1H), 7.83 (dd, 1H, J = 9.2, 1.6 Hz), 7.76 (d, 1H, J = 9.2 Hz), 7.46 (t, 1H, J = 7.8 Hz), 7.24 (br s, 1H), 6.99 (d, 1H, overlapped, J = 8.0 Hz), 6.95 (t, 1H, overlapped, J = 8.0 Hz), 6.76-6.70 (m, 2H), 4.73 (br s, 1H), 4.56 (d, 2H, J = 5.6 Hz), 3.60 (s, 2H), 2.50 (s, 3H), 2.36 (s, 6H) | 457.23 |
| 111 | ·HCl | (400 MHz, DMSO-d$_6$) δ 10.62 (br s, 1H), 9.46 (s, 1H), 8.62 (s, 1H), 7.96 (d, 1H, J = 9.2 Hz), 7.84 (t, 1H, overlapped, J = 8.0 Hz), 7.83 (d, 1H, overlapped, J = 9.2 Hz), 7.57 (d, 1H, J = 8.0 Hz), 7.37 (d, 1H, J = 8.0 Hz), 7.10 (t, 1H, J = 7.6 Hz), 6.93 (pseudo t, 1H, J = 6.6 Hz), 4.78 (s, 2H), 4.30 (d, 2H, J = 4.8 Hz), 2.72 (d, 6H, J = 4.4 Hz), 2.53 (s, 3H) | |
| 112 | 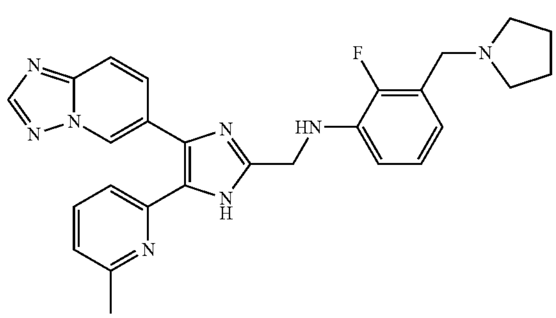 | (400 MHz, CDCl$_3$) δ 11.11 (br s, 1H), 8.98 (s, 1H), 8.35 (s, 1H), 7.81 (dd, 1H, J = 9.2, 1.6 Hz), 7.73 (d, 1H, J = 9.2 Hz), 7.44 (t, 1H, J = 7.8 Hz), 7.23 (br s, 1H), 6.97 (d, 1H, J = 8.0 Hz), 6.91 (t, 1H, J = 8.0 Hz), 6.75 (td, 1H, J = 8.0, 1.2 Hz), 6.65 (td, 1H, J = 8.0, 1.2 Hz), 4.66 (br s, 1H), 4.51 (d, 2H, J = 5.6 Hz), 3.66 (s, 2H), 2.59 (br s, 4H), 2.42 (s, 3H), 1.81-1.75 (m, 4H) | 483.24 |

TABLE 1-continued

| Example | Structure | ¹H NMR (ppm) | MS (ESI) m/z (MH⁺) |
|---|---|---|---|
| 113 | 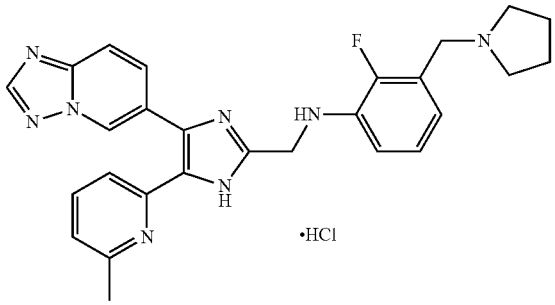 | (400 MHz, DMSO-d₆) δ 10.84 (br s, 1H), 9.46 (s, 1H), 8.62 (s, 1H), 7.95 (d, 1H, J = 9.2 Hz), 7.84 (t, 1H, J = 7.8 Hz), 7.83 (dd, 1H, J = 9.2, 1.6 Hz), 7.57 (d, 1H, J = 8.0 Hz), 7.36 (d, 1H, J = 9.2, 1.6 Hz), 7.08 (t, 1H, J = 7.8 Hz), 7.03-6.96 (m, 2H), 4.77 (s, 2H), 4.36 (d, 2H, J = 5.2 Hz), 3.39 (m, 2H), 3.07 (m, 2H), 2.53 (s, 3H), 2.03-1.87 (m, 4H) | |
| 114 | 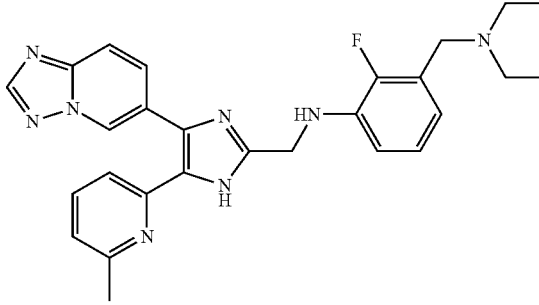 | (400 MHz, CDCl₃) δ 8.97 (s, 1H), 8.36 (s, 1H), 7.82 (dd, 1H, J = 9.2, 2.0 Hz), 7.76 (dd, 1H, J = 9.2, 0.8 Hz), 7.46 (t, 1H, J = 7.6 Hz), 7.23 (br d, 1H, J = 7.6 Hz), 7.00 (d, 1H, J = 7.6 Hz), 6.95 (t, 1H, J = 8.0 Hz), 6.76 (t, 1H, J = 7.6 Hz), 6.70 (td, 1H, J = 8.0, 1.6 Hz), 4.67 (br s, 1H), 4.54 (d, 2H, J = 4.8 Hz), 3.73 (m, 4H), 3.59 (s, 2H), 2.53 (br s, 4H), 2.47 (s, 3H) | 499.24 |
| 115 | 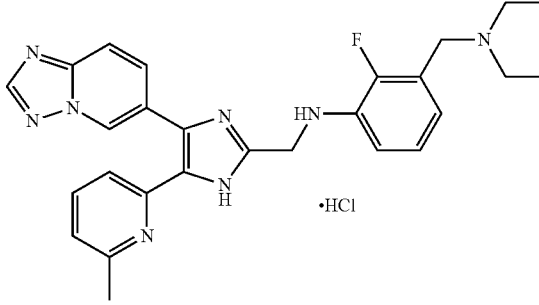 | (400 MHz, DMSO-d₆) δ 11.18 (br s, 1H), 9.46 (dd, 1H, J = 1.6, 1.2 Hz), 8.62 (s, 1H), 7.96 (dd, 1H, J = 9.2, 0.8 Hz), 7.84 (t, 1H, overlapped, J = 7.8 Hz), 7.83 (dd, 1H, overlapped, J = 9.2, 1.6 Hz), 7.57 (d, 1H, J = 7.6 Hz), 7.37 (d, 1H, J = 8.0 Hz), 7.10 (t, 1H, J = 7.8 Hz), 7.05-6.99 (m, 2H), 4.78 (s, 2H), 4.34 (s, 2H), 3.93 (br s, 2H), 3.81 (br t, 2H, J = 11.8 Hz) 3.29 (br s, 2H), 3.13 (br s, 2H), 2.53 (s, 3H) | |
| 116 | 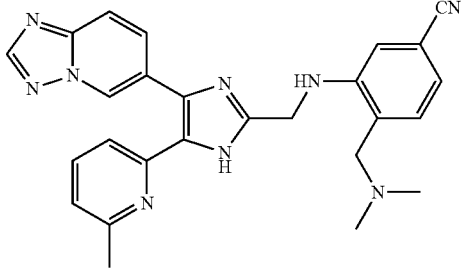 | (400 MHz, CDCl₃) δ 8.99 (s, 1H), 8.36 (s, 1H), 7.86 (dd, 1H, J = 9.2, 1.6 Hz), 7.78 (dd, 1H, J = 9.2, 0.8 Hz), 7.47 (t, 1H, J = 7.6 Hz), 7.23 (br d, 1H, J = 7.6 Hz), 7.09 (d, 1H, J = 7.6 Hz), 7.01 (d, 1H, J = 7.6 Hz), 6.98 (dd, 1H, J = 7.6, 1.6 Hz), 6.93 (br s, 1H), 4.59 (s, 2H), 3.63 (s, 2H), 2.53 (s, 3H), 2.33 (s, 6H) | 464.23 |
| 117 | 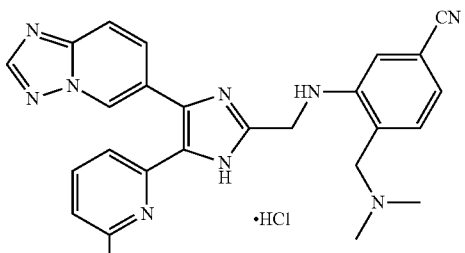 | (400 MHz, DMSO-d₆) δ 9.45 (dd, 1H, J = 1.6, 0.8 Hz), 8.60 (s, 1H), 7.94 (dd, 1H, J = 9.2, 0.8 Hz), 7.85 (t, 1H, overlapped, J = 7.6 Hz), 7.84 (dd, 1H, overlapped, J = 9.2, 1.6 Hz), 7.57 (d, 1H, J = 7.6 Hz), 7.52 (d, 1H, J = 8.0 Hz), 7.39 (d, 1H, J = 7.6 Hz), 7.30 (br s, 1H), 7.19-7.17 (m, 2H), 4.79 (s, 2H), 4.48 (s, 2H), 2.78 (s, 6H), 2.55 (s, 3H) | |

TABLE 1-continued

| Example | Structure | ¹H NMR (ppm) | MS (ESI) m/z (MH⁺) |
|---|---|---|---|
| 118 | 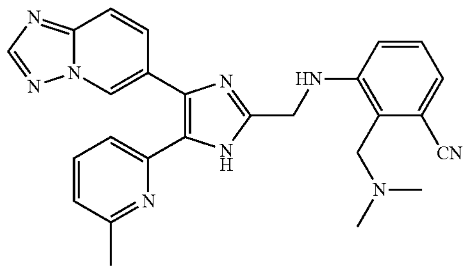 | (400 MHz, DMSO-d₆) δ 12.70 (br s, 1H), 9.54 (s, 1H), 8.50 (s, 1H), 7.99 (dd, 1H, J = 9.2, 2.0 Hz), 7.83 (dd, 1H, J = 9.2, 0.8 Hz), 7.72 (t, 1H, J = 7.8 Hz), 7.52 (br s, 1H), 7.32 (t, 1H, J = 7.6 Hz), 7.17-7.13 (m, 2H), 7.07 (d, 1H, J = 8.0 Hz), 7.02 (dd, 1H, J = 7.6, 0.8 Hz), 4.48 (d, 2H, J = 5.6 Hz), 3.68 (s, 2H), 2.47 (s, 3H), 2.23 (s, 6H) | 464.23 |
| 119 | 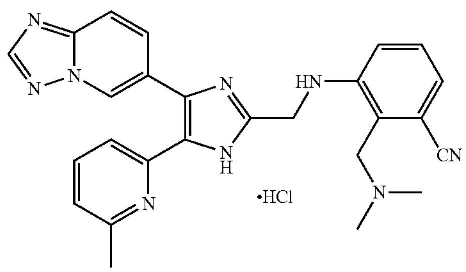 | (400 MHz, DMSO-d₆) δ 9.48 (t, 1H, J = 1.2 Hz), 8.60 (s, 1H), 7.92 (dd, 1H, J = 9.2, 1.2 Hz), 7.86 (dd, 1H, overlapped, J = 9.2, 1.6 Hz), 7.85 (t, 1H, overlapped, J = 8.0 Hz), 7.64 (d, 1H, J = 8.0 Hz), 7.49 (t, 1H, J = 7.8 Hz), 7.37 (d, 1H, J = 8.0 Hz), 7.24 (dd, 1H, J = 7.6, 0.8 Hz), 7.10 (dd, 1H, J = 8.0, 0.8 Hz), 4.81 (s, 2H), 4.61 (s, 2H), 2.89 (s, 6H), 2.52 (s, 3H) | |
| 120 | 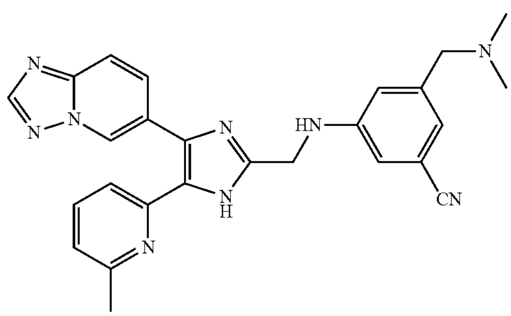 | (400 MHz, CDCl₃) δ 9.01 (s, 1H), 8.36 (s, 1H), 7.83 (dd, 1H, J = 9.2, 1.6 Hz), 7.76 (dd, 1H, J = 9.2, 0.8 Hz), 7.49 (t, 1H, J = 7.6 Hz), 7.28 (br d, 1H, J = 7.6 Hz), 7.15 (br s, 1H), 7.03 (d, 1H, J = 7.6 Hz), 6.94 (s, 1H), 6.82 (dd, 1H, J = 2.0, 1.2 Hz), 4.86 (br s, 1H), 4.55 (d, 2H, J = 5.6 Hz), 3.48 (s, 2H), 2.54 (s, 3H), 2.32 (s, 6H) | 464.23 |
| 121 | 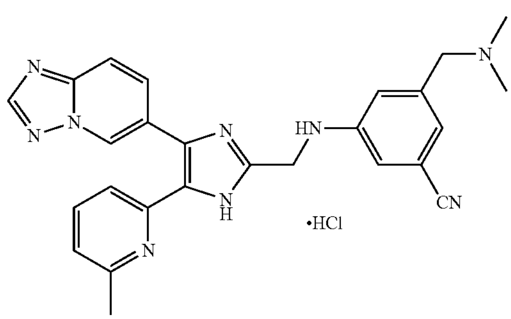 | (400 MHz, DMSO-d₆) δ 10.77 (br s, 1H), 9.46 (dd, 1H, J = 1.6, 0.8 Hz), 8.60 (s, 1H), 7.94 (dd, 1H, J = 9.2, 0.8 Hz), 7.85 (dd, 1H, overlapped, J = 9.2, 1.6 Hz), 7.84 (t, 1H, overlapped, J = 7.8 Hz), 7.55 (d, 1H, J = 7.6 Hz), 7.36 (d, 1H, overlapped, J = 8.0 Hz), 7.35 (s, 1H, overlapped), 7.23 (br s, 2H), 4.71 (s, 2H), 4.22 (s, 2H), 2.67 (s, 6H), 2.53 (s, 3H) | |
| 122 | 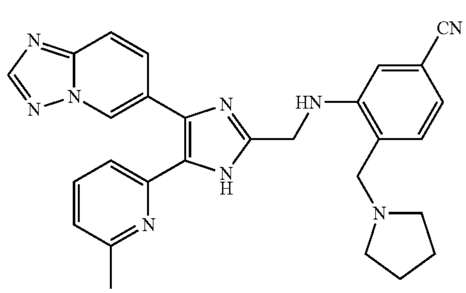 | (400 MHz, CDCl₃) δ 10.40 (br s, 1H), 8.96 (s, 1H), 8.36 (s, 1H), 7.84 (dd, 1H, J = 9.2, 1.6 Hz), 7.77 (d, 1H, J = 9.2 Hz), 7.46 (t, 1H, J = 7.6 Hz), 7.24 (br d, 1H, J = 7.6 Hz), 7.09 (d, 1H, J = 7.6 Hz), 7.00 (d, 1H, J = 7.6 Hz), 6.96 (dd, 1H, J = 7.6, 1.6 Hz), 6.86 (br s, 1H), 4.55 (s, 2H), 3.74 (s, 2H), 2.54 (br s, 4H), 2.51 (s, 3H), 1.81 (br s, 4H) | 490.25 |

TABLE 1-continued

| Example | Structure | $^1$H NMR (ppm) | MS (ESI) m/z (MH$^+$) |
|---|---|---|---|
| 123 | 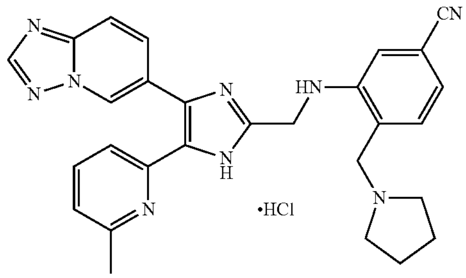 | (400 MHz, DMSO-d$_6$) δ 10.47 (br s, 2H), 9.46 (s, 1H), 8.61 (s, 1H), 7.95 (dd, 1H, J = 9.2, 0.4 Hz), 7.86 (t, 1H, overlapped, J = 7.6 Hz), 7.85 (dd, 1H, overlapped, J = 9.2, 1.2 Hz), 7.60 (d, 1H, J = 7.6 Hz), 7.59 (d, 1H, J = 8.0 Hz), 7.39 (d, 1H, J = 7.6 Hz), 7.32 (br s, 1H), 7.18 (dd, 1H, J = 7.6, 1.6 Hz), 7.14 (d, 1H, J = 1.6 Hz), 4.82 (s, 2H), 4.53 (s, 2H), 3.23 (br s, 4H), 2.55 (s, 3H), 1.99 (br s, 4H) | |
| 124 | 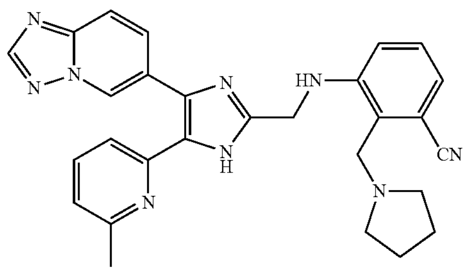 | (400 MHz, DMSO-d$_6$) δ 12.71 (br s, 1H), 9.52 (s, 1H), 8.50 (s, 1H), 7.98 (dd, 1H, J = 9.2, 1.6 Hz), 7.83 (d, 1H, J = 9.2 Hz), 7.71 (t, 1H, J = 7.8 Hz), 7.51 (br s, 1H), 7.37 (t, 1H, J = 5.2 Hz), 7.31 (t, 1H, J = 8.0 Hz), 7.16 (d, 1H, J = 7.6 Hz), 7.05 (d, 1H, J = 8.0 Hz), 7.00 (dd, 1H, J = 8.0, 1.2 Hz), 4.47 (d, 2H, J = 5.2 Hz), 3.87 (s, 2H), 2.51 (br s, 4H), 2.47 (s, 3H), 1.74 (br s, 4H) | 490.25 |
| 125 | 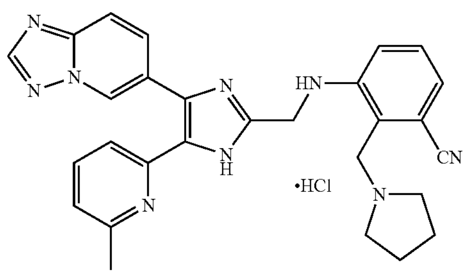 | (400 MHz, DMSO-d$_6$/D$_2$O) δ 9.41 (dd, 1H, J = 1.6, 0.8 Hz), 8.61 (s, 1H), 7.94 (dd, 1H, J = 9.2, 0.8 Hz), 7.89 (t, 1H, J = 7.8 Hz), 7.84 (dd, 1H, J = 9.2, 1.6 Hz), 7.55 (d, 1H, J = 8.0 Hz), 7.50 (t, 1H, J = 7.6 Hz), 7.42 (d, 1H, J = 7.6 Hz), 7.25 (dd, 1H, J = 7.6, 0.8 Hz), 7.09 (d, 1H, J = 7.6 Hz), 4.78 (s, 2H), 4.64 (s, 2H), 3.45 (br s, 4H), 2.58 (s, 3H), 2.06 (br s, 4H) | |
| 126 | 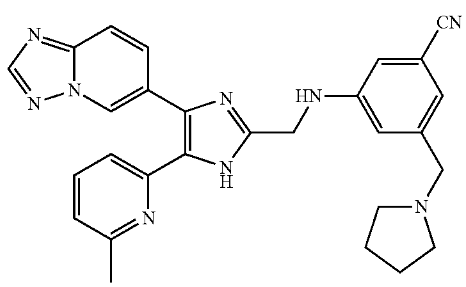 | (400 MHz, CDCl$_3$) δ 8.99 (s, 1H), 8.36 (s, 1H), 7.82 (dd, 1H, J = 9.2, 1.6 Hz), 7.77 (d, 1H, J = 9.2 Hz), 7.48 (t, 1H, J = 7.6 Hz), 7.27 (br d, 1H, J = 7.6 Hz), 7.13 (br s, 1H), 7.03 (d, 1H, J = 7.6 Hz), 6.97 (br s, 1H), 6.81 (dd, 1H, J = 2.4, 1.2 Hz), 4.81 (br s, 1H), 4.54 (d, 2H, J = 5.6 Hz), 3.62 (s, 2H), 2.57 (br s, 4H), 2.54 (s, 3H), 1.79 (br s, 4H) | 490.25 |
| 127 | 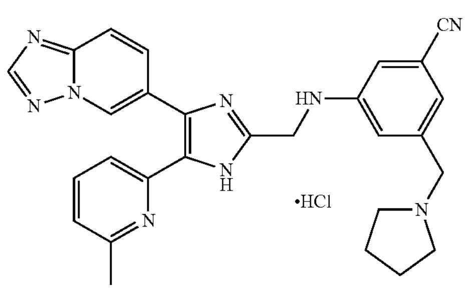 | (400 MHz, DMSO-d$_6$) δ 10.96 (br s, 1H), 9.45 (dd, 1H, J = 1.6, 0.8 Hz), 8.60 (s, 1H), 7.94 (dd, 1H, J = 9.2, 0.8 Hz), 7.84 (dd, 1H, overlapped, J = 9.2, 1.6 Hz), 7.83 (t, 1H, overlapped, J = 7.8 Hz), 7.54 (d, 1H, J = 8.0 Hz), 7.39 (br s, 1H), 7.36 (d, 1H, J = 7.6 Hz), 7.26 (s, 1H), 7.21 (dd, 1H, J = 2.0, 1.6 Hz), 4.72 (s, 2H), 4.29 (s, 2H), 3.02 (br s, 4H), 2.53 (s, 3H), 1.95 (br s, 2H), 1.84 (br s, 2H) | |

TABLE 1-continued

| Example | Structure | $^1$H NMR (ppm) | MS (ESI) m/z (MH$^+$) |
|---|---|---|---|
| 128 | 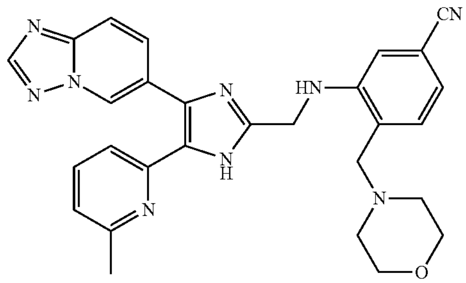 | (400 MHz, CDCl$_3$) δ 8.97 (s, 1H), 8.37 (s, 1H), 7.84 (dd, 1H, J = 9.2, 1.6 Hz), 7.79 (dd, 1H, J = 9.2, 1.2 Hz), 7.49 (t, 1H, J = 7.8 Hz), 7.29 (br d, 1H, J = 8.0 Hz), 7.12 (d, 1H, J = 7.6 Hz), 7.03 (d, 1H, J = 7.6 Hz), 6.99 (dd, 1H, J = 7.6, 1.6 Hz), 6.93 (br s, 1H), 4.57 (s, 2H), 3.75 (br s, 4H, overlapped), 3.72 (s, 2H, overlapped), 2.55 (br s, 7H) | 506.25 |
| 129 | 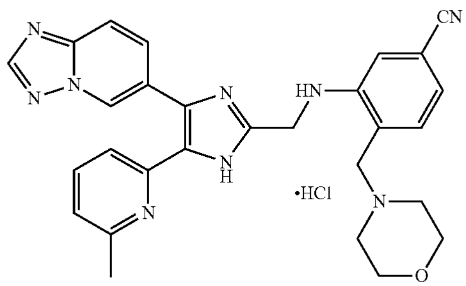 | (400 MHz, DMSO-d$_6$) δ 9.45 (d, 1H, J = 0.4 Hz), 8.61 (s, 1H), 7.96 (d, 1H, J = 9.2 Hz), 7.86 (t, 1H, overlapped, J = 8.0 Hz), 7.85 (dd, 1H, overlapped, J = 9.2, 1.6 Hz), 7.60 (d, 1H, J = 8.0 Hz), 7.57 (d, 1H, J = 8.0 Hz), 7.39 (d, 1H, J = 8.0 Hz), 7.19 (s, 1H), 7.17 (dd, 1H, overlapped, J = 8.0, 1.2 Hz), 4.82 (s, 2H), 4.52 (s, 2H), 3.91 (br s, 4H), 3.32 (br s, 4H), 2.55 (s, 3H) | |
| 130 | 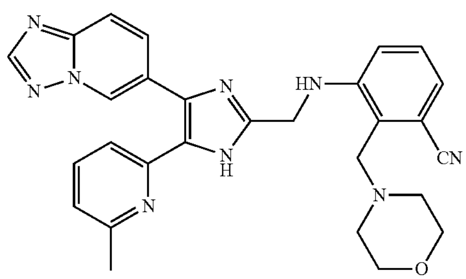 | (400 MHz, DMSO-d$_6$) δ 12.70 (br s, 1H), 9.48 (br s, 1H), 8.50 (s, 1H), 7.95 (dd, 1H, J = 9.2, 1.6 Hz), 7.84 (d, 1H, J = 9.2 Hz), 7.71 (t, 1H, J = 7.6 Hz), 7.44 (br s, 1H), 7.34 (t, 1H, J = 8.0 Hz), 7.28 (t, 1H, J = 5.6 Hz), 7.16 (d, 1H, J = 7.6 Hz), 7.07 (d, 1H, J = 8.4 Hz), 7.03 (dd, 1H, J = 7.6, 1.2 Hz), 4.49 (d, 2H, J = 5.6 Hz), 3.76 (s, 2H), 3.58 (m, 4H), 2.48 (s, 3H), 2.41 (br s, 4H) | 506.24 |
| 131 | 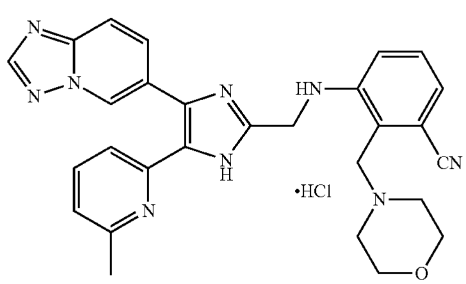 | (400 MHz, DMSO-d$_6$) δ 9.46 (d, 1H, J = 0.8 Hz), 8.60 (s, 1H), 7.94 (dd, 1H, J = 9.2, 0.8 Hz), 7.85 (t, 1H, overlapped, J = 7.6 Hz), 7.84 (dd, 1H, overlapped, J = 9.2, 1.6 Hz), 7.60 (d, 1H, J = 8.0 Hz), 7.47 (t, 1H, J = 8.0 Hz), 7.37 (d, 1H, J = 8.0 Hz), 7.22 (dd, 1H, J = 7.6, 0.8 Hz), 7.08 (d, 1H, J = 8.0 Hz), 4.82 (s, 2H), 4.57 (s, 2H), 3.95 (br t, 4H, J = 4.4 Hz), 3.40 (br s, 4H), 2.53 (s, 3H) | |
| 132 | 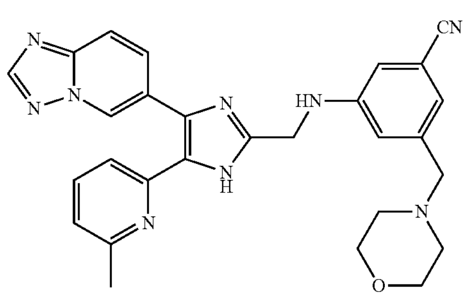 | (400 MHz, CDCl$_3$) δ 8.97 (s, 1H), 8.38 (s, 1H), 7.82 (dd, 1H, J = 9.2, 1.6 Hz), 7.78 (dd, 1H, J = 9.2, 0.8 Hz), 7.48 (t, 1H, J = 7.6 Hz), 7.28 (br d, 1H, J = 7.6 Hz), 7.06 (br s, 1H, overlapped), 7.04 (d, 1H, J = 7.6 Hz), 7.01 (s, 1H), 6.84 (dd, 1H, J = 2.0, 1.2 Hz), 4.79 (br s, 1H), 4.54 (d, 2H, J = 7.6 Hz), 3.70 (m, 4H), 3.48 (s, 2H), 2.55 (s, 3H), 2.47 (br s, 4H) | 506.24 |

TABLE 1-continued

| Example | Structure | ¹H NMR (ppm) | MS (ESI) m/z (MH⁺) |
|---|---|---|---|
| 133 | 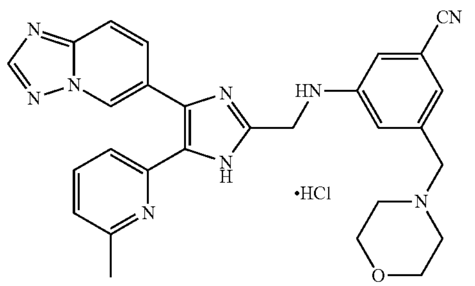 | (400 MHz, DMSO-d₆) δ 9.45 (dd, 1H, J = 1.6, 0.8 Hz), 8.61 (s, 1H), 7.95 (dd, 1H, J = 9.2, 0.8 Hz), 7.85 (t, 1H, overlapped, J = 7.6 Hz), 7.84 (dd, 1H, overlapped, J = 9.2, 1.6 Hz), 7.54 (d, 1H, J = 7.6 Hz), 7.43 (br s, 1H), 7.37 (d, 1H, J = 7.6 Hz), 7.28 (s, 1H), 7.23 (dd, 1H, J = 2.2, 1.4 Hz), 4.74 (s, 2H), 4.28 (s, 2H), 3.83 (br s, 4H), 3.81 (br s, 2H), 3.08 (br s, 2H), 2.54 (s, 3H) | |
| 134 | 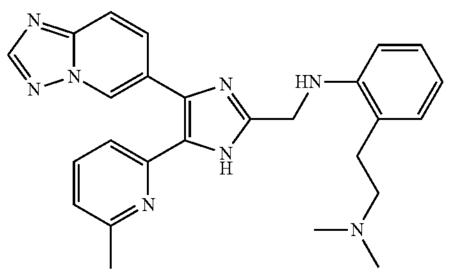 | (400 MHz, CDCl₃) δ 8.98 (s, 1H), 8.36 (s, 1H), 7.83 (dd, 1H, J = 9.2, 1.6 Hz), 7.76 (dd, 1H, J = 9.2, 0.8 Hz), 7.45 (t, 1H, J = 7.8 Hz), 7.23 (br d, 1H, J = 7.6 Hz), 7.13 (td, 1H, J = 8.0, 1.2 Hz), 7.04 (dd, 1H, J = 8.0, 1.2 Hz), 6.99 (d, 1H, J = 8.0 Hz), 6.72 (d, 1H, overlapped, J = 7.6 Hz), 6.71 (td, 1H, overlapped, J = 8.0, 1.2 Hz), 4.56 (s, 2H), 2.81 (t, 2H, J = 6.4 Hz), 2.63 (t, 2H, J = 6.4 Hz), 2.52 (s, 3H), 2.36 (s, 6H) | 453.25 |
| 135 | 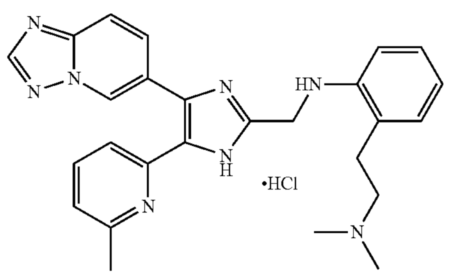 | (400 MHz, DMSO-d₆/D₂O) δ 9.40 (dd, 1H, J = 1.8, 0.8 Hz), 8.63 (s, 1H), 7.96 (dd, 1H, J = 9.2, 0.8 Hz), 7.86 (t, 1H, J = 7.8 Hz), 7.82 (dd, 1H, J = 9.2, 1.8 Hz), 7.48 (d, 1H, J = 8.0 Hz), 7.41 (d, 1H, J = 7.6 Hz), 7.17-7.12 (m, 2H), 6.75-671 (m, 2H), 4.73 (s, 2H), 3.32 (br t, 2H, J = 8.4 Hz), 3.02 (br t, 2H, J = 8.4 Hz), 2.90 (s, 6H), 2.58 (s, 3H) | |
| 136 | 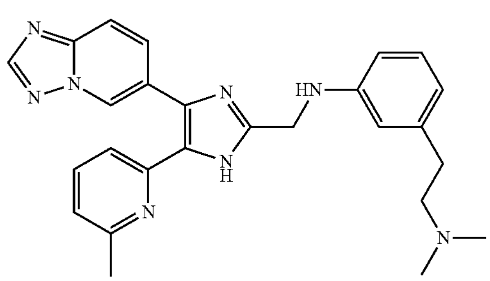 | (400 MHz, CDCl₃) δ 9.08 (s, 1H), 8.32 (s, 1H), 7.83 (dd, 1H, J = 9.2, 1.6 Hz), 7.68 (d, 1H, J = 9.2 Hz), 7.47 (t, 1H, J = 7.6 Hz), 7.34 (br d, 1H, J = 7.6 Hz), 7.04 (t, 1H, J = 7.6 Hz), 6.99 (dd, 1H, J = 7.6, 0.4 Hz), 6.66 (br s, 1H), 6.53-6.49 (m, 2H), 4.48 (s, 2H), 2.89-2.83 (m 4H), 2.56 (s, 6H), 2.48 (s, 3H) | 453.25 |
| 137 | 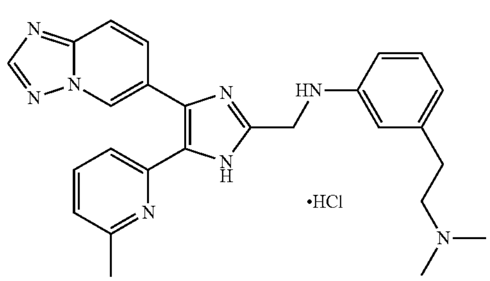 | (400 MHz, DMSO-d₆) δ 10.47 (br s, 1H), 9.49 (t, 1H, J = 0.8 Hz), 8.63 (s, 1H), 7.97 (dd, 1H, J = 9.2, 0.8 Hz), 7.85 (dd, 1H, overlapped, J = 9.2, 1.2 Hz), 7.84 (t, 1H, overlapped, J = 7.8 Hz), 7.64 (d, 1H, J = 8.0 Hz), 7.37 (d, 1H, J = 7.6 Hz), 7.10 (t, 1H, J = 8.0 Hz), 6.81 (br s, 1H), 6.66 (dd, 1H, J = 8.0, 1.6 Hz), 6.58 (d, 1H, J = 8.0 Hz), 4.75 (s, 2H), 3.30-3.25 (m, 2H), 2.94-2.89 (m, 2H), 2.77 (d, 6H, J = 4.8 Hz), 2.51 (s, 3H) | |

| Example | Structure | ¹H NMR (ppm) | MS (ESI) m/z (MH⁺) |
|---|---|---|---|
| 138 | 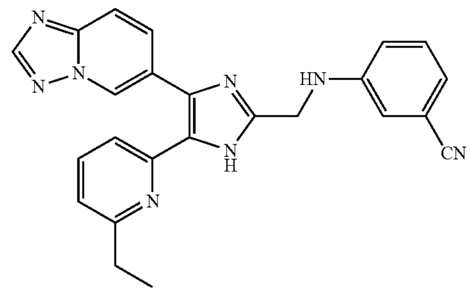 | (400 MHz, CDCl₃) δ 10.40 (br s, 1H), 8.94 (s, 1H), 8.38 (s, 1H), 7.83 (dd, 1H, J = 9.2, 1.2 Hz), 7.80 (dd, 1H, J = 9.2, 0.8 Hz), 7.49 (d, 1H, J = 7.8 Hz), 7.30-7.27 (m, 1H), 7.24 (d, 1H, J = 8.0 Hz), 7.06 (dt, 1H, overlapped, J = 7.6, 1.2 Hz), 7.05 (d, 1H, overlapped, J = 7.6 Hz), 6.94-6.93 (m, 2H), 4.72 (t, 1H, J = 5.2 Hz), 4.54 (d, 2H, J = 5.2 Hz), 2.82 (q, 2H, J = 7.6 Hz), 1.31 (t, 3H, J = 7.6 Hz) | 421.21 |
| 139 | 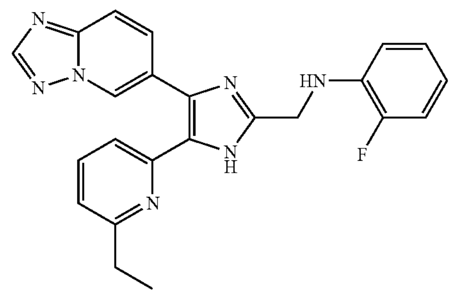 | (400 MHz, CDCl₃) δ 10.37 (br s, 1H), 8.96 (s, 1H), 8.38 (s, 1H), 7.84 (dd, 1H, J = 9.2, 1.2 Hz), 7.79 (dd, 1H, J = 9.2, 0.8 Hz), 7.48 (t, 1H, J = 7.8 Hz), 7.22 (d, 1H, J = 8.0 Hz), 7.06-7.00 (m, 3H), 6.80 (td, 1H, J = 8.0, 1.2 Hz), 6.76-6.70 (m, 1H), 4.62 (br s, 1H, overlapped), 4.60 (s, 2H), 2.80 (q, 2H, J = 7.6 Hz), 1.29 (t, 3H, J = 7.6 Hz) | 414.20 |

Practice Example 5

Preparation of N-((4-([1,2,4]triazolo[1,5-a]pyridin-6-yl)-5-(6-methylpyridin-2-yl)-1H-imidazol-2-yl)methyl)-2-fluoro-N-methylaniline (Example 140)

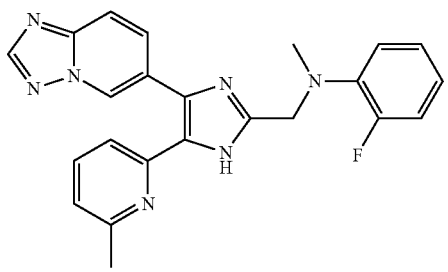

To a stirred solution of 1-((1,2,4)triazolo(1,5-a)pyridin-6-yl)-2-(6-methylpyridin-2-yl)ethane-1,2-dione (0.20 g, 0.75 mmol) in a mixture of tert-butyl methyl ether (10 mL) and MeOH (8 mL) were added 2((2-fluorophenyl)(methyl)amino)acetaldehyde (190 mg, 1.13 mmol) and NH₄OAc (0.15 g, 1.88 mmol), and the mixture was stirred at room temperature for 2 h. The pH of the mixture was adjusted to 8 with saturated aqueous NaHCO₃ solution. After removal of the solvent, the reaction mixture was extracted with CHCl₃ (2×100 mL), and the CHCl₃ solution was washed with water (20 mL) and brine (20 mL), dried over anhydrous Na₂SO₄, filtered, and evaporated to dryness under reduced pressure. The residue was purified by MPLC on silica gel using a mixture of MeOH and CH₂Cl₂ (1:19 (v/v)) as eluent to give the titled compound (90 mg, 32%) as a pale yellow solid. ¹H NMR (400 MHz, CDCl₃) δ 8.97 (br s, 1H), 8.37 (s, 1H), 7.82 (dd, 1H, J=9.2, 1.6 Hz), 7.78 (dd, 1H, J=9.2, 1.2 Hz), 7.49 (t, 1H, J=7.8 Hz), 7.25 (br d, 1 H, J=7.6 Hz), 7.14-7.06 (m, 3H), 7.04 (d, 1H, J=7.6 Hz), 7.00-6.94 (m, 1H), 4.44 (s, 2H), 2.91 (s, 3H), 2.58 (s, 3H); MS (ESI) m/z 414.20 (MH⁺).

Practice Example 6

Preparation of 3-((4-([1,2,4]triazolo[1,5-a]pyridin-6-yl)-5-(6-methylpyridin-2-yl)-1H-imidazol-2-yl)methyl)benzonitrile (Example 145)

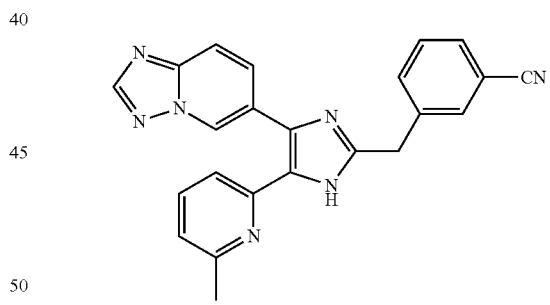

To a stirred solution of 1-((1,2,4)triazolo(1,5-a)pyridin-6-yl)-2-(6-methylpyridin-2-yl)ethane-1,2-dione (4.00 g, 15.02 mmol) in a mixture of tert-butyl methyl ether (30 mL) and MeOH (30 mL) were added 3-(fomylmethyl)benzonitrile (prepared according to the method described in WO 02/096875 A1) (6.54 g, 45.07 mmol) and NH₄OAc (11.58 g, 150.24 mmol), and the mixture was stirred at room temperature for 90 min. The pH of the mixture was adjusted to 8 with saturated aqueous NaHCO₃ solution. After removal of solvent, the mixture was extracted with EtOAc (2×150 mL), and the EtOAc solution was washed with water (50 mL) and brine (50 mL), dried over anhydrous Na₂SO₄, filtered, and evaporated to dryness under reduced pressure. The residue was purified by MPLC on silica gel using a mixture of MeOH and CH₂Cl₂ (1:19 (v/v)) as eluent to give the titled compound (1.92 g, 33%) as a yellow solid. $^1$H NMR (400 MHz, DMSO-$d_6$) δ 12.70 (br s, 1H), 9.53 (br s, 1H), 8.49 (s, 1H), 7.96 (dd, 1H, J=9.2, 1.8 Hz), 7.84 (d, 1H, J=2.0 Hz), 7.82 (d, 1H, J=9.2 Hz), 7.74-7.71 (m, 2H), 7.69 (t, 1H, overlapped, J=7.6 Hz), 7.56 (t, 1H, J=7.8 Hz), 7.47 (br s, 1H), 7.15 (d, 1H, J=7.6 Hz), 4.18 (s, 2H), 2.47 (s, 3H); MS (ESI) m/z 392.18 (MH$^+$).

Practice Example 7

Preparation of 3-((4-([1,2,4]triazolo[1,5-a]pyridin-6-yl)-5-(6-methylpyridin-2-yl)-1H-imidazol-2-yl)methyl)benzamide (Example 147)

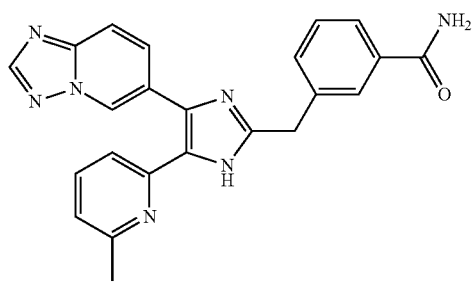

To a stirred solution of 3-((4-([1,2,4]triazolo[1,5-a]pyridin-6-yl)-5-(6-methylpyridin-2-yl)-1H-imidazol-2-yl)methyl)benzonitrile (41 mg, 0.10 mmol) in EtOH (2 mL) were added 28% $H_2O_2$ (13.9 mL, 0.11 mmol) and 1N NaOH (0.39 mL, 0.39 mmol) at room temperature. The mixture was heated to at 60° C. for 1 h and then, to it, was added 1 N HCl at 0° C. to adjust pH 7-8. After removal of the solvent, the residue was extracted with $CH_2Cl_2$ (2×15 mL). The $CH_2Cl_2$ solution was washed with water (5 mL) and brine (5 mL), dried over anhydrous $Na_2SO_4$, filtered, and evaporated to dryness under reduced pressure. The residue was purified by MPLC on silica gel using a mixture of MeOH and $CH_2Cl_2$ (1:9 (v/v)) as eluent to give the titled compound (15 mg, 35%) as a yellow solid. $^1$H NMR (400 MHz, CDCl$_3$) δ 8.93 (br s, 1H), 8.32 (s, 1H), 7.77 (s, 1H), 7.76 (dd, 1H, overlapped, J=9.2, 1.6 Hz), 7.69 (d, 1H, J=9.2 Hz), 7.56 (d, 1H, J=8.0 Hz), 7.44 (t, 1H, J=7.6 Hz), 7.39 (d, 1H, J=7.6 Hz), 7.26 (t, 1H, J=8.0 Hz), 7.21 (d, 1H, J=7.6 Hz), 6.98 (d, 1H, J=7.6 Hz), 6.60 (br s, 1H), 6.27 (br s, 1H), 4.15 (s, 2H), 2.44 (s, 3 H); MS (ESI) m/z 410.19 (MH$^+$).

The compounds listed in the following Table 2 were prepared in an analogous manner to those described in the Practice Examples 5-7 above. The mass spectroscopy data of these compounds are included in the Table 2.

TABLE 2

| Example | Structure | $^1$H NMR (ppm) | MS (ESI) m/z (MH$^+$) |
|---|---|---|---|
| 140 | 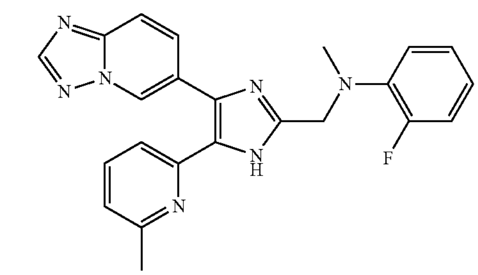 | (400 MHz, CDCl$_3$) δ 8.97 (br s, 1 H), 8.37 (s, 1 H), 7.82 (dd, 1 H, J = 9.2, 1.6 Hz), 7.78 (dd, 1 H, J = 9.2, 1.2 Hz), 7.49 (t, 1 H, J = 7.8 Hz), 7.25 (br d, 1 H, J = 7.6 Hz), 7.14-7.06 (m, 3 H), 7.04 (d, 1 H, J = 7.6 Hz), 7.00-6.94 (m, 1 H), 4.44 (s, 2 H), 2.91 (s, 3 H), 2.58 (s, 3 H) | 414.20 |
| 141 | 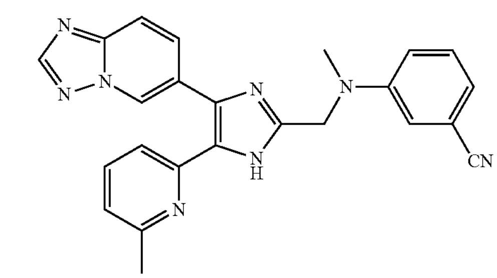 | (400 MHz, CDCl$_3$) δ 8.93 (s, 1 H), 8.37 (s, 1 H), 7.80-7.78 (m, 2 H), 7.48 (t, 1 H, J = 7.6 Hz), 7.35-7.30 (m, 1 H), 7.24 (br d, 1 H, J = 8.0 Hz), 7.08-7.05 (m, 3 H), 7.02 (d, 1 H, J = 7.6 Hz), 4.67 (s, 2 H), 3.14 (s, 3 H), 2.50 (s, 3 H) | 421.20 |
| 142 | 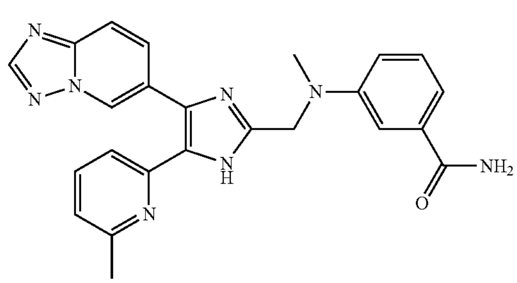 | (400 MHz, CDCl$_3$/CD$_3$OD) δ 8.86 (dd, 1 H, J = 1.6, 1.2 Hz), 8.18 (s, 1 H), 7.62 (dd, 1 H, J = 9.2, 1.6 Hz), 7.57 (dd, 1 H, J = 9.2, 1.2 Hz), 7.43 (t, 1 H, J = 8.0 Hz), 7.24 (dd, 1 H, J = 2.4, 1.6 Hz), 7.14 (t, 1 H, overlapped, J = 8.0 Hz), 7.13 (d, 1 H, overlapped, J = 8.0 Hz), 7.04 (ddd, 1 H, J = 8.0, 1.2, 0.8 Hz), 6.97 (d, 1 H, J = 7.6 Hz), 6.83 (ddd, 1 H, 1 = 8.0, 2.4, 0.8 Hz), 4.54 (s, 2 H), 2.99 (s, 3 H), 2.38 (s, 3 H) | 439.22 |

TABLE 2-continued

| Example | Structure | ¹H NMR (ppm) | MS (ESI) m/z (MH⁺) |
|---|---|---|---|
| 143 | 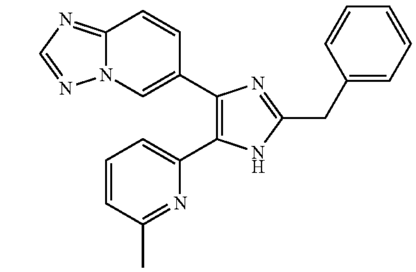 | (400 MHz, CDCl₃) δ 8.94 (br s, 1 H), 8.36 (s, 1 H), 7.81 (dd, 1 H, J = 9.2, 1.6 Hz), 7.77 (dd, 1 H, J = 9.2, 0.8 Hz), 7.44 (t, 1 H, J = 7.8 Hz), 7.40-7.28 (m, 5 H), 7.20 (br d, 1 H, J = 8.0 Hz), 6.99 (d, 1 H, J = 7.6 Hz), 4.21 (s, 2 H), 2.51 (s, 3 H) | 367.18 |
| 144 | 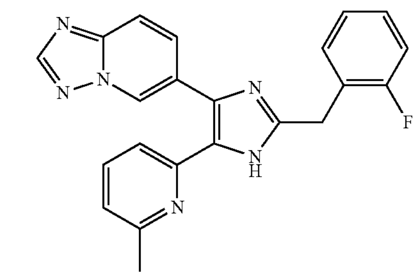 | (400 MHz, CDCl₃) δ 8.93 (t, 1 H, J = 1.2 Hz), 8.37 (s, 1 H), 7.80 (dd, 1 H, overlapped, J = 9.2, 1.6 Hz), 7.77 (dd, 1 H, overlapped, J = 9.2, 0.8 Hz), 7.46 (t, 1 H, J = 7.8 Hz), 7.39 (td, 1 H, J = 7.6, 1.6 Hz), 7.31-7.25 (m, 1 H), 7.21 (br d, 1 H, J = 8.0 Hz), 7.14 (td, 1 H, overlapped, J = 7.6, 1.2 Hz), 7.10 (dd, 1 H, J = 8.4, 1.2 Hz), 7.02 (br d, 1 H, J = 7.6 Hz), 4.24 (s, 2 H), 2.55 (s, 3 H) | 385.17 |
| 145 | 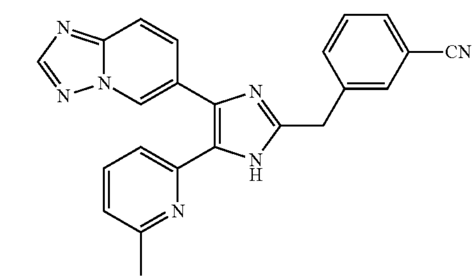 | (400 MHz, DMSO-d₆) δ 12.70 (br s, 1 H), 9.53 (br s, 1 H), 8.49 (s, 1 H), 7.96 (dd, 1 H, J = 9.2, 1.8 Hz), 7.84 (d, 1 H, J = 2.0 Hz), 7.82 (d, 1 H, J = 9.2 Hz), 7.74-7.71 (m, 2 H), 7.69 (t, 1 H, overlapped, J = 7.6 Hz), 7.56 (t, 1 H, J = 7.8 Hz), 7.47 (br s, 1 H), 7.15 (d, 1 H, J = 7.6 Hz), 4.18 (s, 2 H), 2.47 (s, 3 H) | 392.18 |
| 146 | 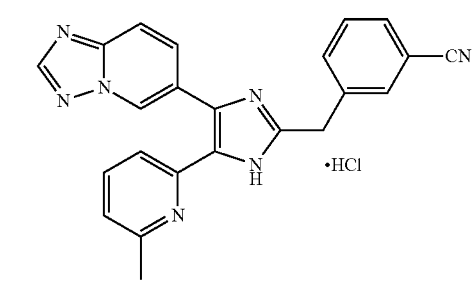 | (400 MHz, DMSO-d₆) δ 9.51 (dd, 1 H, J = 1.6, 0.8 Hz), 8.65 (s, 1 H), 8.08 (br s, 1 H), 7.97 (dd, 1 H, overlapped, J = 9.2, 0.8 Hz), 7.95 (br d, overlapped, 1 H, J = 8.0 Hz), 7.87 (dd, 1 H, J = 9.2, 1.6 Hz), 7.85-7.79 (m, 2 H), 7.63 (dd, 1 H, overlapped, J = 7.6, 1.2 Hz), 7.61 (t, 1 H, overlapped, J = 7.6 Hz), 7.36 (d, 1 H, J = 7.6 Hz), 4.55 (s, 2 H), 2.50 (s, 3 H) | |
| 147 | 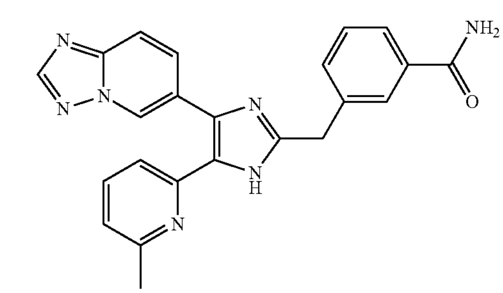 | (400 MHz, CDCl₃) δ 8.93 (br s, 1 H), 8.32 (s, 1 H), 7.77 (s, 1 H), 7.76 (dd, 1 H, overlapped, J = 9.2, 1.6 Hz), 7.69 (d, 1 H, J = 9.2 Hz), 7.56 (d, 1 H, J = 8.0 Hz), 7.44 (t, 1 H, J = 7.6 Hz), 7.39 (d, 1 H, J = 7.6 Hz), 7.26 (t, 1 H, J = 8.0 Hz), 7.21 (d, 1 H, J = 7.6 Hz), 6.98 (d, 1 H, J = 7.6 Hz), 6.60 (br s, 1 H), 6.27 (br s, 1 H), 4.15 (s, 2 H), 2.44 (s, 3 H) | 410.19 |

TABLE 2-continued

| Example | Structure | ¹H NMR (ppm) | MS (ESI) m/z (MH⁺) |
|---|---|---|---|
| 148 | 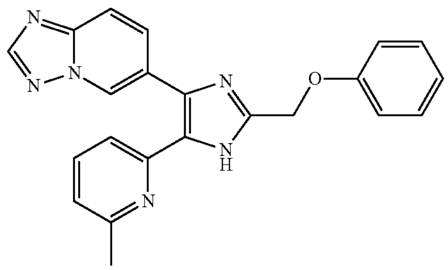 | (400 MHz, CDCl₃) δ 8.94 (s, 1 H), 8.37 (s, 1 H), 7.77-7.72 (m, 2 H), 7.51 (t, 1 H, J = 7.6 Hz), 7.32-7.25 (m, 3 H), 7.06 (d, 1 H, J = 7.6 Hz), 7.00 (t, 1 H, overlapped, J = 7.6 Hz), 6.97 (d, 2 H, overlapped, J = 8.0 Hz), 5.22 (s, 2 H), 2.54 (s, 3 H) | 383.17 |
| 149 | 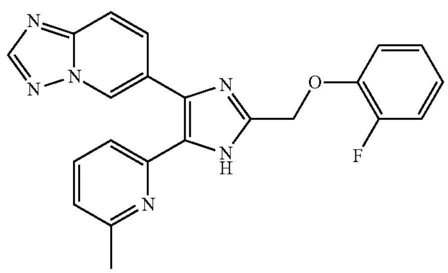 | (400 MHz, CDCl₃) δ 8.95 (t, 1 H, J = 1.2 Hz), 8.38 (s, 1 H), 7.80 (dd, 1 H, J = 9.2, 0.8 Hz), 7.77 (dd, 1 H, J = 9.2, 1.2 Hz), 7.56 (t, 1 H, J = 8.0 Hz), 7.31 (d, 1 H, J = 7.6 Hz), 7.19 (td, 1 H, J = 8.0, 1.6 Hz), 7.14-7.06 (m, 3 H), 7.01-6.95 (m, 1 H), 5.34 (s, 2 H), 2.64 (s, 3 H) | 401.17 |
| 150 | 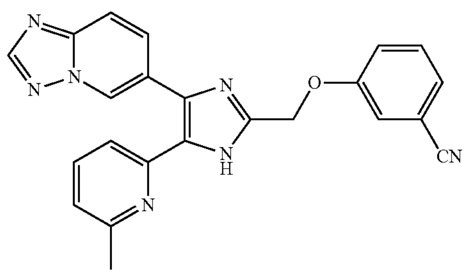 | (400 MHz, CDCl₃/CD₃OD) δ 8.94 (dd, 1 H, J = 1.6, 1.2 Hz), 8.32 (s, 1 H), 7.78 (dd, 1 H, J = 9.2, 1.6 Hz), 7.73 (dd, 1 H, J = 9.2, 1.2 Hz), 7.52 (t, 1 H, J = 7.8 Hz), 7.42-7.37 (m, 1 H), 7.31-7.26 (m, 3 H), 7.25 (br d, 1 H, overlapped, J = 8.0 Hz), 7.07 (d, 1 H, J = 7.6 Hz), 5.23 (s, 2 H), 2.55 (s, 3 H) | 408.17 |
| 151 | 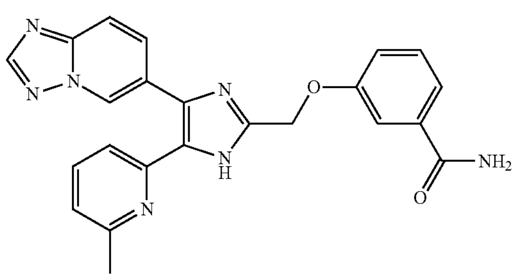 | (400 MHz, CDCl₃/CD₃OD) δ 8.94 (t, 1 H, J = 1.6 Hz), 8.31 (s, 1 H), 7.76 (dd, 1 H, J = 9.2, 1.6 Hz), 7.70 (dd, 1 H, J = 9.2, 0.8 Hz), 7.51-7.47 (m, 2 H), 7.42 (ddd, 1 H, J = 8.0, 2.4, 1.2 Hz), 7.31 (t, 1 H, J =8.0 Hz), 7.23 (d, 1 H, J = 7.6 Hz), 7.12 (ddd, 1 H, J = 8.0, 2.4, 0.8 Hz), 7.04 (d, 1 H, J = 7.6 Hz), 5.22(s, 2 H), 2.51 (s, 3 H) | 426.18 |
| 152 | 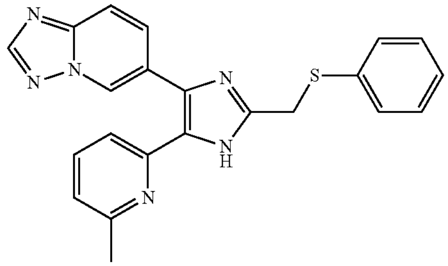 | (400 MHz, CDCl₃) δ 8.89 (t, 1 H, J = 1.4 Hz), 8.35 (s, 1 H), 7.76-7.19 (m, 2 H), 7.45 (t, 1 H, J = 7.8 Hz), 7.39-7.36 (m, 2 H), 7.30-7.26 (m, 2 H), 7.23-7.19 (m, 2 H), 7.01 (d, 1 H, J = 7.6 Hz), 4.26 (s, 2 H), 2.49 (s, 3 H) | 399.15 |

TABLE 2-continued

| Example | Structure | $^1$H NMR (ppm) | MS (ESI) m/z (MH$^+$) |
|---|---|---|---|
| 153 | 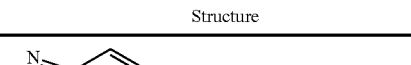 | (400 MHz, CDCl$_3$) δ 8.86 (br s, 1 H), 8.37 (s, 1 H), 7.78 (dd, 1 H, J = 9.2, 0.8 Hz), 7.72 (dd, 1 H, J = 9.2, 1.6 Hz), 7.54-7.48 (m, 2 H), 7.31-7.27 (m, 1 H), 7.25 (br d, 1 H, J = 8.0 Hz), 7.13-7.08 (m, 2 H), 7.06 (d, 1 H, J = 8.0 Hz), 4.30 (s, 2 H), 2.64 (s, 3 H) | 417.15 |

Biological Data

The biological activity of the compounds of the invention may be assessed using the following assays:

Cell-Free Assay for Evaluating Inhibition of ALK5 Kinase Phosphorylation of Smad3

The His-tagged, constitutively active ALK5 (T204D) and Smad3 full protein were expressed in insect cells using the Invitrogen BacNBlue baculovirus expression system. Expressed proteins were purified with Qiagen Ni-NTA resin column. The purified smad3 protein 200 ng was mixed with 100 μl of 0.1 M sodium bicarbonate coating buffer and coated into Flash-Plates by pipetting. Plates were covered and incubated at 4° C. for 16 h. Then, the plates were washed 3 times with 200 μL of coating buffer and allowed to block in 1% BSA in PBS at room temperature for 1 h. The purified ALK5 protein 100 ng was mixed with 100 μL of reaction buffer containing 20 mM Tris-HCl (pH 7.4), 5 mM MgCl$_2$, 1 mM CaCl$_2$, 1 mM DTT, 1 μM ATP and 2 μCi γ-$^{32}$P-ATP, and 1 μL of each test compound of formula (I) prepared in 100% DMSO solution at different concentrations. The assay was then initiated with the addition of ALK5 reaction mixture into Smad3-coated Flash-Plates, followed by incubation at 30° C. for 3 h. After incubation, the assay buffer was removed and washed 3 times with 200 μL of 10 mM sodium pyrophosphate solution. Then, the Flash-Plates were air-dried and counted on a Packard TopCount.

Compounds of formula (I) typically exhibited IC$_{50}$ values of less than 1 μM; some exhibited IC$_{50}$ values of less than 0.1 μM; and some even exhibited IC$_{50}$ values less than 10 nM.

Cell-Free Assay for Evaluating Inhibition of ALK4 Kinase Phosphorylation of Smad3 Inhibition of the ALK4 kinase phosphorylation of Smad3 by test compounds of formula (I) can be determined in a similar manner to that described above for ALK5 inhibition except that a similarly His-tagged ALK4 is used in place of the His-tagged, constitutively active ALK5.

Compounds of formula (I) typically exhibited IC$_{50}$ values of less than 1 μM; some exhibited IC$_{50}$ values of less than 0.1 μM.

Assay for Evaluating Cellular Inhibition of TGF-β Signaling

4T103Tp-Luc stable cells or HaCaT-3TP-Lux stable cells that have p3TP-Lux (neo) expression plasmid were seeded and treated with TGF-β1 in 0.2% FBS (2 ng/mL) in the presence or absence of each test compounds of formula (I) at approximately 60-70% confluence for 20 h. Cell lysates were used to measure luciferase activity. Data were normalized by measuring concentration of total protein.

Compounds of formula (I) typically exhibited IC$_{50}$ values of less than 1 μM; some exhibited IC$_{50}$ values of less than 0.1 μM; and some even exhibited IC$_{50}$ values less than 10 nM.

Evaluation of Anti-metastatic Activity of Example 60 in Vivo

Tumor-bearing MMTV/c-Neu mice were treated either saline (vehicle) or example 60 (40 mg/kg, in 100 μl, saline) by intraperitoneal injection every other day for 3 weeks. The tumor size was measured using calipers, and the tumor volumes were calculated by using the following equation:

Tumor volume=(0.5236)×(width)$^2$×(length)

After sacrifice, mammary tumor and lung tissues were analyzed by hematoxylin and eosin (H & E) staining. In the Balb/c xenograft model, 4T1 cells (1×10$^4$ in 100 μL, PBS) were transplanted into the left thoracic mammary fat pads of 10-weeks-old female Balb/c mice, and mice were randomized into two group (n=6 per groups). Ten days after transplantation, tumor-bearing Balb/c mice were administered either saline (vehicle) or example 60 (40 mg/kg, in 100 μL saline) by intraperitoneal injection every other day for 2.5 weeks. The tumor size was measured using calipers, and metastastic nodules on the left lobe surface of lungs were visualized by india ink injection into the trachea and counted.

What is claimed is:

1. A compound of the formula (I):

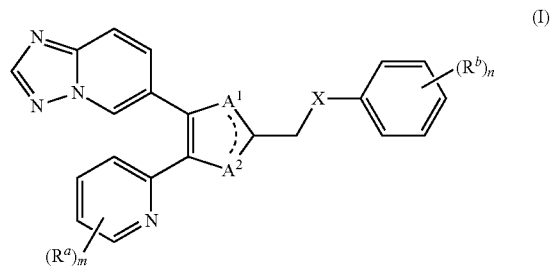

(I)

wherein:
each R$^a$ is independently H, halo, C$_{1-6}$alkyl, C$_{1-6}$haloalkyl, C$_{3-6}$cycloalkyl, OH, —O—C$_{1-6}$alkyl, —O—C$_{1-6}$haloalkyl, —O—C$_{3-6}$cycloalkyl, NH$_2$, —NH—C$_{1-6}$alkyl, —NH—C$_{1-6}$haloalkyl, —NH—C$_{3-6}$cycloalkyl, —S—C$_{1-6}$alkyl, —S—C$_{1-6}$haloalkyl, —S—C$_{3-6}$cycloalkyl, CN, or NO$_2$;
m is 0, 1, 2, 3, or 4;
one of A$^1$ and A$^2$ is N and the other is NR$^1$, wherein R$^1$ is H, OH, C$_{1-6}$alkyl, C$_{1-6}$ haloalkyl, or C$_{3-6}$cycloalkyl;
X is —NR$^2$—, —O—, or —S—, and R$^2$ is H or C$_{1-3}$alkyl;
each R$^b$ is independently H, halo, C$_{1-6}$alkyl, C$_{1-6}$haloalkyl, C$_{3-6}$cycloalkyl, C$_{2-6}$alkenyl, C$_{2-6}$alkynyl, —(CH$_2$)$_q$—OR$^3$, —(CH$_2$)$_q$—NR$^3$R$^4$, —(CH$_2$)$_q$—SR$^3$, —(CH$_2$)$_q$—NO$_2$, —(CH$_2$)$_q$—CONHOH, —(CH$_2$)$_q$—CN, —(CH$_2$)$_q$—COR$^3$, —(CH$_2$)$_q$—CO$_2$R$^3$, —(CH$_2$)$_q$—CONR$^3$R$^4$, —(CH$_2$)$_q$-tetrazole, —(CH$_2$)$_q$—CH═CH—CN, —(CH$_2$)$_q$—CH═CH—CO$_2$R$^3$, —(CH$_2$)$_q$—CH═CH—CONR$^3$R$^4$, —(CH$_2$)$_q$—CH═CH-tetrazole, —(CH$_2$)$_q$—NHCOR$^3$, —(CH$_2$)$_q$—NHCO$_2$R$^3$, —(CH$_2$)$_q$—CONHSO$_2$R$^3$, —(CH$_2$)$_q$—NHSO$_2$R$^3$, —(CH$_2$)$_q$—C≡C—CN, —(CH$_2$)$_q$—C≡C—CO$_2$R$^3$, —(CH$_2$)$_q$—C≡C—CONR$^3$R$^4$, —(CH$_2$)$_q$—C≡C-tetrazole, —(CH$_2$)$_q$—SOR$^5$, —(CH$_2$)$_q$—SO$_2$R$^5$, or —(CH$_2$)$_r$—(OR$^3$)$_2$, wherein R$^3$ and R$^4$ are independently H, C$_{1-6}$alkyl, C$_{1-6}$haloalkyl, or C$_{3-6}$cycloalkyl; or taken together with the nitrogen atom to which they are attached form a mono-cyclic ring such as imidazole, pyrrolidine, piperidine, morpholine, piperazine and homopiperazine; R$^5$ is C$_{1-6}$alkyl, C$_{1-6}$haloalkyl, or C$_{3-6}$cycloalkyl; q is 0, 1, 2, 3, or 4; and r is 1, 2, 3, or 4;

n is 0, 1, 2, 3, 4, or 5; or a pharmaceutically acceptable salt thereof.

2. The compound of claim 1, which is selected from the group consisting of:

N-((4-([1,2,4]triazolo[1,5-a]pyridin-6-yl)-5-(6-methylpyridin-2-yl)-1H-imidazol-2-yl)methyl)aniline;

N-((4-([1,2,4]triazolo[1,5-a]pyridin-6-yl)-5-(6-methylpyridin-2-yl)-1H-imidazol-2-yl)methyl)-2-fluoroaniline;

N-((4-([1,2,4]triazolo[1,5-a]pyridin-6-yl)-5-(6-methylpyridin-2-yl)-1H-imidazol-2-yl)methyl)-3-fluoro aniline;

N-((4-([1,2,4]triazolo[1,5-a]pyridin-6-yl)-5-(6-methylpyridin-2-yl)-1H-imidazol-2-yl)methyl)-4-fluoroaniline;

N-((4-([1,2,4]triazolo[1,5-a]pyridin-6-yl)-5-(6-methylpyridin-2-yl)-1H-imidazol-2-yl)methyl)-2,3-difluoroaniline;

N-((4-([1,2,4]triazolo[1,5-a]pyridin-6-yl)-5-(6-methylpyridin-2-yl)-1H-imidazol-2-yl)methyl)-3,4-difluoroaniline;

N-((4-([1,2,4]triazolo[1,5-a]pyridin-6-yl)-5-(6-methylpyridin-2-yl)-1H-imidazol-2-yl)methyl)-3,5-difluoroaniline;

N-((4-([1,2,4]triazolo[1,5-a]pyridin-6-yl)-5-(6-methylpyridin-2-yl)-1H-imidazol-2-yl)methyl)-2-chloroaniline;

N-((4-([1,2,4]triazolo[1,5-a]pyridin-6-yl)-5-(6-methylpyridin-2-yl)-1H-imidazol-2-yl)methyl)-3-chloroaniline;

N-((4-([1,2,4]triazolo[1,5-a]pyridin-6-yl)-5-(6-methylpyridin-2-yl)-1H-imidazol-2-yl)methyl)-4-chloroaniline;

N-((4-([1,2,4]triazolo[1,5-a]pyridin-6-yl)-5-(6-methylpyridin-2-yl)-1H-imidazol-2-yl)methyl)-2,3-dichloroaniline;

N-((4-([1,2,4]triazolo[1,5-a]pyridin-6-yl)-5-(6-methylpyridin-2-yl)-1H-imidazol-2-yl)methyl)-3,4-dichloroaniline;

N-((4-([1,2,4]triazolo[1,5-a]pyridin-6-yl)-5-(6-methylpyridin-2-yl)-1H-imidazol-2-yl)methyl)-3,5-dichloroaniline;

N-((4-([1,2,4]triazolo[1,5-a]pyridin-6-yl)-5-(6-methylpyridin-2-yl)-1H-imidazol-2-yl)methyl)-2-bromoaniline;

N-((4-([1,2,4]triazolo[1,5-a]pyridin-6-yl)-5-(6-methylpyridin-2-yl)-1H-imidazol-2-yl)methyl)-3-bromoaniline;

N-((4-([1,2,4]triazolo[1,5-a]pyridin-6-yl)-5-(6-methylpyridin-2-yl)-1H-imidazol-2-yl)methyl)-4-bromoaniline;

N-((4-([1,2,4]triazolo[1,5-a]pyridin-6-yl)-5-(6-methylpyridin-2-yl)-1H-imidazol-2-yl)methyl)-2-methylaniline;

N-((4-([1,2,4]triazolo[1,5-a]pyridin-6-yl)-5-(6-methylpyridin-2-yl)-1H-imidazol-2-yl)methyl)-3-methylaniline;

N-((4-([1,2,4]triazolo[1,5-a]pyridin-6-yl)-5-(6-methylpyridin-2-yl)-1H-imidazol-2-yl)methyl)-4-methylaniline;

N-((4-([1,2,4]triazolo[1,5-a]pyridin-6-yl)-5-(6-methylpyridin-2-yl)-1H-imidazol-2-yl)methyl)-2,3-dimethylaniline;

N-((4-([1,2,4]triazolo[1,5-a]pyridin-6-yl)-5-(6-methylpyridin-2-yl)-1H-imidazol-2-yl)methyl)-3,4-dimethylaniline;

N-((4-([1,2,4]triazolo[1,5-a]pyridin-6-yl)-5-(6-methylpyridin-2-yl)-1H-imidazol-2-yl)methyl)-3,5-dimethylaniline;

N-((4-([1,2,4]triazolo[1,5-a]pyridin-6-yl)-5-(6-methylpyridin-2-yl)-1H-imidazol-2-yl)methyl)-2-ethylaniline;

N-((4-([1,2,4]triazolo[1,5-a]pyridin-6-yl)-5-(6-methylpyridin-2-yl)-1H-imidazol-2-yl)methyl)-3-ethylaniline;

N-((4-([1,2,4]triazolo[1,5-a]pyridin-6-yl)-5-(6-methylpyridin-2-yl)-1H-imidazol-2-yl)methyl)-2-isopropylaniline;

N-((4-([1,2,4]triazolo[1,5-a]pyridin-6-yl)-5-(6-methylpyridin-2-yl)-1H-imidazol-2-yl)methyl)-3-isopropylaniline;

N-((4-([1,2,4]triazolo[1,5-a]pyridin-6-yl)-5-(6-methylpyridin-2-yl)-1H-imidazol-2-yl)methyl)-4-isopropylaniline;

N-((4-([1,2,4]triazolo[1,5-a]pyridin-6-yl)-5-(6-methylpyridin-2-yl)-1H-imidazol-2-yl)methyl)-2-vinylaniline;

N-((4-([1,2,4]triazolo[1,5-a]pyridin-6-yl)-5-(6-methylpyridin-2-yl)-1H-imidazol-2-yl)methyl)-3-vinylaniline;

N-((4-([1,2,4]triazolo[1,5-a]pyridin-6-yl)-5-(6-methylpyridin-2-yl)-1H-imidazol-2-yl)methyl)-4-vinylaniline;

N-((4-([1,2,4]triazolo[1,5-a]pyridin-6-yl)-5-(6-methylpyridin-2-yl)-1H-imidazol-2-yl)methyl)-3-ethynylaniline;

N-((4-([1,2,4]triazolo[1,5-a]pyridin-6-yl)-5-(6-methylpyridin-2-yl)-1H-imidazol-2-yl)methyl)-2-methoxyaniline;

N-((4-([1,2,4]triazolo[1,5-a]pyridin-6-yl)-5-(6-methylpyridin-2-yl)-1H-imidazol-2-yl)methyl)-3-methoxyaniline;

N-((4-([1,2,4]triazolo[1,5-a]pyridin-6-yl)-5-(6-methylpyridin-2-yl)-1H-imidazol-2-yl)methyl)-4-methoxyaniline;

N-((4-([1,2,4]triazolo[1,5-a]pyridin-6-yl)-5-(6-methylpyridin-2-yl)-1H-imidazol-2-yl)methyl)-2,3-dimethoxyaniline;

N-((4-([1,2,4]triazolo[1,5-a]pyridin-6-yl)-5-(6-methylpyridin-2-yl)-1H-imidazol-2-yl)methyl)-3,4-dimethoxyaniline;

N-((4-([1,2,4]triazolo[1,5-a]pyridin-6-yl)-5-(6-methylpyridin-2-yl)-1H-imidazol-2-yl)methyl)-3,5-dimethoxyaniline;

N-((4-([1,2,4]triazolo[1,5-a]pyridin-6-yl)-5-(6-methylpyridin-2-yl)-1H-imidazol-2-yl)methyl)-2-(methoxymethyl)aniline;

N-((4-([1,2,4]triazolo[1,5-a]pyridin-6-yl)-5-(6-methylpyridin-2-yl)-1H-imidazol-2-yl)methyl)-3-(methoxymethyl)aniline;

N-((4-([1,2,4]triazolo[1,5-a]pyridin-6-yl)-5-(6-methylpyridin-2-yl)-1H-imidazol-2-yl)methyl)-4-(methoxymethyl)aniline;

N-((4-([1,2,4]triazolo[1,5-a]pyridin-6-yl)-5-(6-methylpyridin-2-yl)-1H-imidazol-2-yl)methyl)-2-(trifluoromethoxy)aniline;

N-((4-([1,2,4]triazolo[1,5-a]pyridin-6-yl)-5-(6-methylpyridin-2-yl)-1H-imidazol-2-yl)methyl)-3-(trifluoromethoxy)aniline;

N-((4-([1,2,4]triazolo[1,5-a]pyridin-6-yl)-5-(6-methylpyridin-2-yl)-1H-imidazol-2-yl)methyl)-4-(trifluoromethoxy)aniline;
N-((4-([1,2,4]triazolo[1,5-a]pyridin-6-yl)-5-(6-methylpyridin-2-yl)-1H-imidazol-2-yl)methyl)-2-(methylthio)aniline;
N-((4-([1,2,4]triazolo[1,5-a]pyridin-6-yl)-5-(6-methylpyridin-2-yl)-1H-imidazol-2-yl)methyl)-3-(methylthio)aniline;
N-((4-([1,2,4]triazolo[1,5-a]pyridin-6-yl)-5-(6-methylpyridin-2-yl)-1H-imidazol-2-yl)methyl)-4-(methylthio)aniline;
2-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)benzonitrile;
4-((4-([1,2,4]triazolo[1,5-a]pyridin-6-yl)-5-(6-methylpyridin-2-yl)-1H-imidazol-2-yl)methylamino)benzonitrile;
3-((4-([1,2,4]triazolo[1,5-a]pyridin-6-yl)-5-(6-methylpyridin-2-yl)-1H-imidazol-2-yl)methylamino)phthalonitrile;
2-((4-([1,2,4]triazolo[1,5-a]pyridin-6-yl)-5-(6-methylpyridin-2-yl)-1H-imidazol-2-n yl)methylamino)benzamide;
3-((4-([1,2,4]triazolo[1,5-a]pyridin-6-yl)-5-(6-methylpyridin-2-yl)-1H-imidazol-2-yl)methylamino)benzamide;
4-((4-([1,2,4]triazolo[1,5-a]pyridin-6-yl)-5-(6-methylpyridin-2-yl)-1H-imidazol-2-yl)methylamino)benzamide;
2-(3-((4-([1,2,4]triazolo[1,5-a]pyridin-6-yl)-5-(6-methylpyridin-2-yl)-1H-imidazol-2-yl)methylamino)phenyl)acetonitrile;
2-(4-((4-([1,2,4]triazolo[1,5-a]pyridin-6-yl)-5-(6-methylpyridin-2-yl)-1H-imidazol-2-yl)methylamino)phenyl)acetonitrile;
1-(3-((4-([1,2,4]triazolo[1,5-a]pyridin-6-yl)-5-(6-methylpyridin-2-yl)-1H-imidazol-2-yl)methylamino)phenyl)ethanone;
1-(4-((4-([1,2,4]triazolo[1,5-a]pyridin-6-yl)-5-(6-methylpyridin-2-yl)-1H-imidazol-2-yl)methylamino)phenyl)ethanone;
Methyl 3-((4-([1,2,4]triazolo[1,5-a]pyridin-6-yl)-5-(6-methylpyridin-2-yl)-1H-imidazol-2-yl)methylamino)benzoate;
Methyl 4-((4-([1,2,4]triazolo[1,5-a]pyridin-6-yl)-5-(6-methylpyridin-2-yl)-1H-imidazol-2-yl)methylamino)benzoate;
N-(2-((4-([1,2,4]triazolo[1,5-a]pyridin-6-yl)-5-(6-methylpyridin-2-yl)-1H-imidazol-2-yl)methylamino)phenyl)acetamide;
N-(3-((4-([1,2,4]triazolo[1,5-a]pyridin-6-yl)-5-(6-methylpyridin-2-yl)-1H-imidazol-2-yl)methylamino)phenyl)acetamide;
N-(4-((4-([1,2,4]triazolo[1,5-a]pyridin-6-yl)-5-(6-methylpyridin-2-yl)-1H-imidazol-2-yl)methylamino)phenyl)acetamide;
N-(2-((4-([1,2,4]triazolo[1,5-a]pyridin-6-yl)-5-(6-methylpyridin-2-yl)-1H-imidazol-2-yl)methylamino)phenyl)methanesulfonamide;
N-(3-((4-([1,2,4]triazolo[1,5-a]pyridin-6-yl)-5-(6-methylpyridin-2-yl)-1H-imidazol-2-yl)methylamino)phenyl)methanesulfonamide;
N-(4-((4-([1,2,4]triazolo[1,5-a]pyridin-6-yl)-5-(6-methylpyridin-2-yl)-1H-imidazol-2-yl)methylamino)phenyl)methanesulfonamide;
$N^1$-((4-([1,2,4]triazolo[1,5-a]pyridin-6-yl)-5-(6-methylpyridin-2-yl)-1H-imidazol-2-yl)methyl)-$N^2$,$N^2$-dimethylbenzene-1,2-diamine;
$N^1$-((4-([1,2,4]triazolo[1,5-a]pyridin-6-yl)-5-(6-methylpyridin-2-yl)-1H-imidazol-2-yl)methyl)-$N^3$,$N^3$-dimethylbenzene-1,3-diamine;
N-((4-([1,2,4]triazolo[1,5-a]pyridin-6-yl)-5-(6-methylpyridin-2-yl)-1H-imidazol-2-yl)methyl)-2-(pyrrolidin-1-yl)aniline;
N-((4-([1,2,4]triazolo[1,5-a]pyridin-6-yl)-5-(6-methylpyridin-2-yl)-1H-imidazol-2-yl)methyl)-2-morpholinoaniline;
N-((4-([1,2,4]triazolo[1,5-a]pyridin-6-yl)-5-(6-methylpyridin-2-yl)-1H-imidazol-2-yl)methyl)-3-morpholinoaniline;
$N^3$-((4-([1,2,4]triazolo[1,5-a]pyridin-6-yl)-5-(6-methylpyridin-2-yl)-1H-imidazol-2-yl)methyl)-4-fluoro-$N^1$,$N^1$-dimethylbenzene-1,3-diamine;
3-((4-([1,2,4]triazolo[1,5-a]pyridin-6-yl)-5-(6-methylpyridin-2-yl)-1H-imidazol-2-yl)methylamino)-5-(dimethylamino)benzonitrile;
3-((4-([1,2,4]triazolo[1,5-a]pyridin-6-yl)-5-(6-methylpyridin-2-yl)-1H-imidazol-2-yl)methylamino)-4-(dimethylamino)benzonitrile;
N-((4-([1,2,4]triazolo[1,5-a]pyridin-6-yl)-5-(6-methylpyridin-2-yl)-1H-imidazol-2-yl)methyl)-2-((dimethylamino)methyl)aniline;
N-((4-([1,2,4]triazolo[1,5-a]pyridin-6-yl)-5-(6-methylpyridin-2-yl)-1H-imidazol-2-yl)methyl)-3-((dimethylamino)methyl)aniline;
N-((4-([1,2,4]triazolo[1,5-a]pyridin-6-yl)-5-(6-methylpyridin-2-yl)-1H-imidazol-2-yl)methyl)-2-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-(morpholinomethyl)aniline;
N-((4-([1,2,4]triazolo[1,5-a]pyridin-6-yl)-5-(6-methylpyridin-2-yl)-1H-imidazol-2-yl)methyl)-3-(morpholinomethyl)aniline;
N-((4-([1,2,4]triazolo[1,5-a]pyridin-6-yl)-5-(6-methylpyridin-2-yl)-1H-imidazol-2-yl)methyl)-5-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-3-((dimethylamino)methyl)-2-fluoroaniline;
N-((4-([1,2,4]triazolo[1,5-a]pyridin-6-yl)-5-(6-methylpyridin-2-yl)-1H-imidazol-2-yl)methyl)-2-fluoro-3-(pyrrolidin-1-ylmethyl)aniline;
N-((4-([1,2,4]triazolo[1,5-a]pyridin-6-yl)-5-(6-methylpyridin-2-yl)-1H-imidazol-2-yl)methyl)-2-fluoro-3-(morpholinomethyl)aniline;
3-((4-([1,2,4]triazolo[1,5-a]pyridin-6-yl)-5-(6-methylpyridin-2-yl)-1H-imidazol-2-yl)methylamino)-4-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-2-((dimethylamino)methyl)benzonitrile;
3-((4-([1,2,4]triazolo[1,5-a]pyridin-6-yl)-5-(6-methylpyridin-2-yl)-1H-imidazol-2-yl)methylamino)-5-((dimethylamino)methyl)benzonitrile;

3-((4-([1,2,4]triazolo[1,5-a]pyridin-6-yl)-5-(6-methylpyridin-2-yl)-1H-imidazol-2-yl)methylamino)-4-(pyrrolidin-1-ylmethyl)benzonitrile;

3-((4-([1,2,4]triazolo[1,5-a]pyridin-6-yl)-5-(6-methylpyridin-2-yl)-1H-imidazol-2-yl)methylamino)-2-(pyrrolidin-1-ylmethyl)benzonitrile;

3-((4-([1,2,4]triazolo[1,5-a]pyridin-6-yl)-5-(6-methylpyridin-2-yl)-1H-imidazol-2-yl)methylamino)-5-(pyrrolidin-1-ylmethyl)benzonitrile;

3-((4-([1,2,4]triazolo[1,5-a]pyridin-6-yl)-5-(6-methylpyridin-2-yl)-1H-imidazol-2-yl)methylamino)-4-(morpholinomethyl)benzonitrile;

3-((4-([1,2,4]triazolo[1,5-a]pyridin-6-yl)-5-(6-methylpyridin-2-yl)-1H-imidazol-2-yl)methylamino)-2-(morpholinomethyl)benzonitrile;

3-((4-([1,2,4]triazolo[1,5-a]pyridin-6-yl)-5-(6-methylpyridin-2-yl)-1H-imidazol-2-yl)methylamino)-5-(morpholinomethyl)benzonitrile;

N-((4-([1,2,4]triazolo[1,5-a]pyridin-6-yl)-5-(6-methylpyridin-2-yl)-1H-imidazol-2-yl)methyl)-2-(2-(dimethylamino)ethylaniline;

N-((4-([1,2,4]triazolo[1,5-a]pyridin-6-yl)-5-(6-methylpyridin-2-yl)-1H-imidazol-2-yl)methyl)-3-(2-(dimethylamino)ethylaniline;

3-((4-([1,2,4]triazolo[1,5-a]pyridin-6-yl)-5-(6-ethylpyridin-2-yl)-1H-imidazol-2-yl)methylamino)benzonitrile;

N-((4-([1,2,4]triazolo[1,5-a]pyridin-6-yl)-5-(6-ethylpyridin-2-yl)-1H-imidazol-2-yl)methyl)-2-fluoroaniline;

N-((4-([1,2,4]triazolo[1,5-a]pyridin-6-yl)-5-(6-methylpyridin-2-yl)-1H-imidazol-2-yl)methyl)-2-fluoro-N-methylaniline;

3-((4-([1,2,4]triazolo[1,5-a]pyridin-6-yl)-5-(6-methylpyridin-2-yl)-1H-imidazol-2-yl)methyl)(methyl)amino)benzonitrile;

3-((4-([1,2,4]triazolo[1,5-a]pyridin-6-yl)-5-(6-methylpyridin-2-yl)-1H-imidazol-2-n yl)methyl)(methyl)amino)benzamide;

6-(5-(6-methylpyridin-2-yl)-2-(phenoxymethyl)-1H-imidazol-4-yl)-[1,2,4]triazolo[1,5-a]pyridine;

6-(2-((2-fluorophenoxy)methyl)-5-(6-methylpyridin-2-yl)-1H-imidazol-4-yl)-[1,2,4]triazolo[1,5-a]pyridine;

3-((4-([1,2,4]triazolo[1,5-a]pyridin-6-yl)-5-(6-methylpyridin-2-yl)-1H-imidazol-2-yl)methoxy)benzonitrile;

3-((4-([1,2,4]triazolo[1,5-a]pyridin-6-yl)-5-(6-methylpyridin-2-yl)-1H-imidazol-2-yl)methoxy)benzamide;

6-(5-(6-methylpyridin-2-yl)-2-(phenylthiomethyl)-1H-imidazol-4-yl)-[1,2,4]triazolo[1,5-a]pyridine; and 6-(2-((2-fluorophenylthio)methyl)-5-(6-methylpyridin-2-yl)-1H-imidazol-4-yl)-[1,2,4]triazolo[1,5-a]pyridine, or a pharmaceutically acceptable salt thereof.

3. A pharmaceutical composition comprising one or more compounds of claim 1, or a pharmaceutically acceptable salt thereof, and a pharmaceutically acceptable diluent or carrier.

\* \* \* \* \*